(12) United States Patent
Jeanguenat et al.

(10) Patent No.: US 6,479,550 B1
(45) Date of Patent: Nov. 12, 2002

(54) α-SULFENIMINO ACID DERIVATIVES

(75) Inventors: André Jeanguenat, Basel (CH); Martin Zeller, Baden (CH); Hugo Ziegler, Witterswil (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 0 days.

(21) Appl. No.: 09/906,374

(22) Filed: Jul. 16, 2001

Related U.S. Application Data

(63) Continuation of application No. PCT/EP00/00247, filed on Jan. 13, 2000.

(30) Foreign Application Priority Data

Jan. 15, 1999 (GB) ............................................. 9900963

(51) Int. Cl.$^7$ ......................... A61K 31/16; A61K 31/24; A61K 31/27; A61K 31/38; A61K 31/275
(52) U.S. Cl. ....................... 514/608; 514/275; 514/357; 514/365; 514/406; 514/438; 514/471; 514/524; 514/539; 544/335; 546/338; 548/203; 548/275.1; 549/72; 549/491; 558/422; 560/18; 564/102
(58) Field of Search ................................ 514/608, 275, 514/357, 365, 406, 438, 471, 524, 539; 564/102; 544/335; 546/338; 548/203, 275.1; 549/72, 491; 558/422; 560/18

(56) References Cited

U.S. PATENT DOCUMENTS 4,040,811 A * 8/1977 Boger et al. ................... 70/78

FOREIGN PATENT DOCUMENTS

| EP | 0 460 575 A1 | 12/1991 |
|----|--------------|---------|
| EP | 0 463 488 A1 | 1/1992 |
| JP | 63 115 875 | 5/1988 |
| WO | WO 96/23763 | 8/1996 |

OTHER PUBLICATIONS

S. Tori et al: Chem. Lett., No. 10, 1984, pp. 1823–1826.
R. Sudo et al: Bull. Chem. Soc. Japan, vol. 42, No. 5, 1969, pp. 1380–1382.
E.M. Gordon et al: J. Org. Chem., vol. 44, No. 8, 1979, pp. 1218–1221.

* cited by examiner

*Primary Examiner*—Peter O'Sullivan
(74) *Attorney, Agent, or Firm*—William A. Teoli, Jr.

(57) ABSTRACT

α-Sulfenimino acid derivatives of formula I

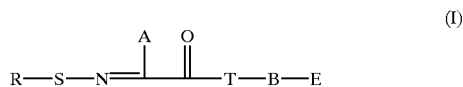

(I)

including the optical isomers thereof and mixtures of such isomers, wherein

A is cycloalkyl, cycloalkenyl, aryl or heteroaryl, each optionally substituted,

B is a direct bond or optionally substituted alkylene,

E is hydrogen or optionally substituted aryl,

R is hydrogen, alkyl, alkenyl, alkynyl, cycloalkyl, cycloalkylalkyl, aryl or arylalkyl, each optionally substituted, and T is NH or oxygen, have been found to be useful for controlling or preventing the infestation of plants by phytopathogenic microorganisms, especially fungi.

The invention relates the novel compounds and also to the preparation thereof and to the use of the compounds for plant protection, and to compositions suitable for applying the novel compounds in agricultural techniques.

9 Claims, No Drawings

α-SULFENIMINO ACID DERIVATIVES

This application is a continuation of PCT/EP00/00247 Jan. 13, 2000.

The present invention relates to novel α-sulfenimino acid derivatives of formula I below. It relates to the preparation of those substances and to agrochemical compositions comprising at least one of those compounds as active ingredient. The invention relates also to the preparation of the said compositions and to the use of the compounds or of the compositions in controlling or preventing the infestation of plants by phytopathogenic microorganisms, especially fungi.

The invention relates to α-sulfenimino acid derivatives of the general formula I

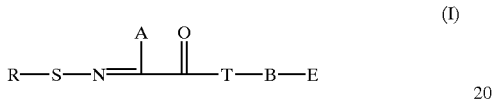

including the optical isomers thereof and mixtures of such isomers, wherein

A is cycloalkyl, cycloalkenyl, aryl or heteroaryl, each optionally substituted,

B is a direct bond or optionally substituted alkylene,

E is hydrogen or optionally substituted aryl,

R is hydrogen, alkyl, alkenyl, alkynyl, cycloalkyl, cycloalkylalkyl, aryl or arylalkyl, each optionally substituted, and T is NH or oxygen.

In the above definition aryl includes aromatic hydrocarbon rings like phenyl, naphthyl, anthracenyl, phenanthrenyl, with phenyl being preferred. Heteroaryl stands for aromatic ring systems comprising mono-, bi- or tricyclic systems wherein at least one oxygen, nitrogen or sulfur atom is present as a ring member. Examples are furyl, thienyl, pyrrolyl, imidazolyl, pyrazolyl, thiazolyl, isothiazolyl, oxazolyl, isoxazolyl, oxadiazolyl, thiadiazolyl, triazolyl, tetrazolyl, pyridyl, pyridazinyl, pyrimidinyl, pyrazinyl, triazinyl, tetrazinyl, indolyl, benzothiophenyl, benzofuranyl, benzimidazolyl, indazolyl, benzotriazolyl, benzothiazolyl, benzoxazolyl, quinolinyl, isoquinolinyl, phthalazinyl, quinoxalinyl, quinazolinyl, cinnolinyl and naphthyridinyl.

The above alkyl, alkenyl, alkynyl, cycloalkyl, aryl and heteroaryl groups may carry one or more identical or different substituents. Normally not more than three substituents in each of these groups are present at the same time.

Preferred subgroups of the compounds of formula I are those wherein

A is phenyl, naphthyl, cycloalkyl, cycloalkenyl or mono- or bicyclic heteroaryl comprising five- or six-membered rings containing 1 to 4 identical or different heteroatoms selected from oxygen, nitrogen or sulfur, wherein each of the cycles is optionally mono- or poly-substituted by substituents selected from the group comprising $C_{1-8}$-alkyl, $C_{2-8}$-alkenyl, $C_{2-8}$-alkynyl, $C_{3-8}$-cycloalkyl, $C_{3-8}$-cycloalkyl-$C_{1-6}$-alkyl, $C_{1-8}$-alkoxy, $C_{3-8}$-alkenyloxy, $C_{3-8}$-alkyn-yloxy, $C_{3-8}$-cycloalkyloxy, $C_{1-8}$-alkylthio, $C_{1-8}$-alkylsulfonyl, $C_{1-8}$-alkanoyl, $C_{1-8}$-alkanoyloxy, $C_{1-8}$-alkoxycarbonyl, $C_{3-8}$-alkenyloxycarbonyl, $C_{3-8}$-alkynyloxycarbonyl, $C_{1-8}$-dialkylamino, $C_{1-8}$-alkylamino, $C_{1-8}$-hydroximinoalkyl and $C_{1-8}$-alkoximinoalkyl, wherein each of the alkyl, alkenyl, alkynyl moieties are straight-chain or branched and may in turn be optionally halogenated; halogen; nitro; cyano; hydroxy; amino; formyl; carboxyl; carbamoyl and thiocarbamoyl; or from the group comprising aryl, aryloxy, arylthio, aryl-$C_{1-4}$-alkyl, aryl-$C_{1-4}$-alkyloxy, aryl-$C_{1-4}$-alkylthio, heterocyclyl, heterocyclyloxy, heterocyclylthio, heterocyclyl-$C_{1-4}$-alkyl, heterocyclyl-$C_{1-4}$-alkoxy and heterocyclyl-$C_{1-4}$-alkylthio, wherein each of the groups may be substituted with halogen, cyano, $C_{1-4}$-alkyl, $C_{1-4}$-alkoxy or $C_{1-4}$-alkylthio, wherein heterocyclyl comprises mono- or bicyclic five- or six-membered non-aromatic and aromatic rings containing 1 to 4 identical or different heteroatoms selected from oxygen, nitrogen or sulfur; or from the group comprising aryloxyalkyl, aryloxyheteroaryloxy, heteroaryloxyalkyl, arylalkyliminoxyalkyl, aryloxyiminoalkyl, arylalkyloxyiminoalkyl, aryloxyiminoalkyleniminoxyalkyl and aryl-alkyloxy-iminoalkyleniminoxyalkyl wherein each alkyl or alkylene may be straight-chain or branched and each alkyl, alkylene, aryl or heteroaryl may in turn be substituted with halogen, cyano, $C_{1-4}$-alkyl, $C_{1-4}$-haloalkyl, $C_{1-4}$-alkoxy, $C_{1-4}$-haloalkoxy, $C_{1-4}$-alkylthio or phenyl or phenoxy wherein the phenyl moieties are optionally substituted with halogen, cyano, $C_{1-4}$-alkyl, $C_{1-4}$-alkoxy or $C_{1-4}$-alkylthio; or A is phenyl, naphthyl, furyl, thienyl, imidazolyl, thiazolyl, oxazolyl, pyridyl, pyrimidinyl, benzothiophenyl, benzthiazolyl, chinolinyl, pyrazolyl, indolyl, benzimidazolyl or pyrrolyl, each optionally-substituted by 1 to 3 substituents selected from the group comprising $C_{1-8}$-alkyl, $C_{2-8}$-alkenyl, $C_{3-8}$-cycloalkyl, $C_{1-8}$-alkoxy, $C_{1-8}$-alkylthio, $C_{1-8}$-alkoxycarbonyl, $C_{1-8}$-haloalkyl, $C_{1-8}$haloalkoxy, $C_{1-8}$-haloalkylthio, halogen, nitro and cyano; or from the group comprising aryl, aryloxy, arylthio, aryl-$C_{1-4}$-alkyl, aryl-$C_{1-4}$-alkyloxy, aryl-$C_{1-4}$-alkylthio, heterocyclyl, heterocyclyloxy, heterocyclylthio, heterocyclyl-$C_{1-4}$-alkyl, heterocyclyl$C_{1-4}$-alkoxy and heterocyclyl-$C_{1-4}$-alkylthio, wherein each of the groups may be substituted with halogen, cyano, $C_{1-4}$-alkyl, $C_{1-4}$-alkoxy or $C_{1-4}$-alkylthio, wherein heterocyclyl is furyl, thienyl, imidazolyl, thiazolyl, oxazolyl, pyridyl, pyrimidinyl, benzothiophenyl, benzthiazolyl, chinolinyl, pyrazolyl, indolyl, benzimidazolyl or pyrrolyl; or from the group comprising phenoxy-$C_{1-4}$-alkyl, phenoxyheteroaryloxy, phenyl-$C_{1-4}$-alkyliminoxy-$C_{1-4}$-alkyl and phenyl-alkoxyimino-$C_{2-4}$-alkyleniminoxy-$C_{1-4}$-alkyl wherein each alkyl or alkylene may be straight-chain or branched and each alkyl, alkylene, phenyl or phenoxy in turn be substituted with halogen, cyano, $C_{1-4}$-alkyl, $C_{1-4}$-haloalkyl, $C_{1-4}$-alkoxy, $C_{1-4}$-haloalkoxy, $C_{1-4}$-alkylthio or phenyl or phenoxy wherein the phenyl moieties are optionally substituted with halogen, cyano, $C_{1-4}$-alkyl, $C_{1-4}$-haloalkyl, $C_{1-4}$-alkoxy, $C_{1-4}$-haloalkoxy or $C_{1-4}$-alkylthio; or A is phenyl, naphthyl, furyl, thienyl, imidazolyl, thiazolyl, oxazolyl, pyridyl, pyrimidinyl, pyrazolyl, indolyl, benzimidazolyl or pyrrolyl, each optionally-substituted by 1 to 3 substituents selected from the group comprising $C_{1-8}$-alkyl, $C_{2-8}$-alkenyl, $C_{3-8}$-cycloalkyl, $C_{1-8}$-alkoxy, $C_{1-8}$-alkylthio, $C_{1-8}$-alkoxycarbonyl, $C_{1-8}$-haloalkyl, $C_{1-8}$-haloalkoxy, $C_{1-8}$-haloalkylthio, halogen, nitro and cyano; or from the group comprising aryl, aryloxy, arylthio, heterocyclyl, heterocyclyloxy and heterocyclylthio, wherein each of the groups may be substituted with halogen, cyano, $C_{1-4}$-alkyl, $C_{1-4}$-alkoxy or $C_{1-4}$-alkylthio, wherein heterocyclyl is furyl, thienyl, imidazolyl, thiazolyl, oxazolyl, pyridyl, pyrimidinyl, pyrazolyl, indolyl or pyrrolyl; or from a group comprising phenoxy-$C_{1-4}$-alkyl, phenyl-$C_{1-4}$-alkyliminoxy-$C_{1-4}$-alkyl and phenyl-alkoxyimino-$C_{2-4}$-alkyleniminoxy-$C_{1-4}$-alkyl wherein each alkyl or alkylene may be straight-chain or branched and each phenyl or phenoxy may in turn be substituted with halogen, cyano, $C_{1-4}$-alkyl, $C_{1-4}$-haloalkyl, $C_{1-4}$-alkoxy, $C_{1-4}$-haloalkoxy or $C_{1-4}$-alkylthio; or A is phenyl, naphthyl, furyl, thienyl, imidazolyl, thiazolyl, oxazolyl, pyridyl, pyrimidinyl, pyrazolyl or pyrrolyl, each optionally-substituted by 1 to 3 substituents selected from the group comprising $C_{1-4}$-alkyl, $C_{2-6}$-alkenyl, $C_{3-6}$-cycloalkyl, $C_{1-4}$-alkoxy, $C_{1-4}$-alkylthio, $C_{1-4}$-alkoxycarbonyl, $C_{1-4}$-haloalkyl, $C_{1-4}$-haloalkoxy, $C_{1-4}$-haloalkylthio, halogen, nitro and cyano; or from the group comprising aryl, aryloxy, arylthio, heterocyclyl, heterocyclyloxy and heterocyclylthio, wherein each of the groups may be substituted with halogen, cyano, $C_{1-4}$-alkyl, $C_{1-4}$-alkoxy or $C_{1-4}$-alkylthio, wherein heterocyclyl is furyl, thienyl, imidazolyl, thiazolyl, oxazolyl, pyridyl, pyrimidinyl, pyrazolyl, indolyl or pyrrolyl; or B is a direct bond or $C_{1-4}$-alkylene which is optionally substituted with substituents selected from the group comprising halogen, linear or branched $C_{1-6}$-alkyl, $C_{2-6}$-alkenyl or $C_{2-6}$-alkynyl and $C_{5-7}$-cycloalkyl, each in turn optionally substituted with 1–4 halogen atoms; or B is a direct bond or $C_{1-4}$-alkylene which is optionally substituted with substituents selected from the group comprising F, Cl, Br, linear or branched $C_{1-4}$-alkyl, $C_{2-4}$-alkenyl or, $C_{2-4}$-alkynyl and $C_{5-7}$-cycloalkyl, each in turn optionally substituted with 1–4 halogen atoms; or B is a direct bond or $C_{1-4}$-alkylene which is optionally substituted with substituents selected from the group comprising F, Cl, Br, linear or branched $C_{1-2}$-alkyl, $C_{2-3}$-alkenyl or, $C_{2-3}$-alkynyl and $C_{5-7}$-cycloalkyl, each in turn optionally substituted with 1–4 halogen atoms; or B is a direct bond, methylene, 1,1-ethylene, 1,2-ethylene, 1,1-propylene, 1,2-propylene, 1,3-propylene or 2,2-propylene; or E is hydrogen or phenyl optionally mono- or poly-substituted with substituents selected from the group comprising $C_{1-8}$-alkyl, $C_{2-8}$-alkenyl, $C_{2-8}$-alkynyl, $C_{3-8}$-cycloalkyl, $C_{3-8}$-cycloalkyl-$C_{1-6}$-alkyl, $C_{1-8}$-alkoxy, $C_{3-8}$-alkenyloxy, $C_{3-8}$-alkynyloxy, $C_{3-8}$-cycloalkyloxy, $C_{6-10}$-aryloxy, $C_{6-10}$-aryl-$C_{1-6}$-alkyloxy, $C_{6-10}$-aryl-$C_{3-6}$-alkenyloxy, $C_{6-10}$-aryl-$C_{3-6}$-alkynyloxy, $C_{3-8}$cycloalkyl-$C_{3-6}$alkynyloxy, $C_{1-8}$-alkanoyloxy, $C_{1-8}$-alkylthio, $C_{1-8}$-alkylsulfonyl, $C_{1-8}$-alkanoyl, $C_{1-8}$-alkoxycarbonyl, $C_{3-8}$-alkinyloxycarbonyl and $C_{3-8}$-alkinyloxycarbonyl wherein in each of the preceding groups the alkyl, alkenyl, alkynyl or cycloalkyl part may be partially or fully halogenated and wherein the aryl groups may be optionally mono- or poly-substituted with substituents selected from the group comprising $C_{1-8}$-alkyl, $C_{2-8}$-alkenyl, $C_{3-8}$-cycloalkyl, $C_{1-8}$-alkoxy, $C_{1-8}$-alkylthio, $C_{1-8}$-alkoxycarbonyl, $C_{1-8}$-haloalkyl, $C_{1-8}$-haloalkoxy, $C_{1-8}$-haloalkylthio, halogen, nitro and cyano; halogen, nitro, cyano, hydroxy, amino, di-$C_{1-8}$-alkylamino and $C_{1-8}$-alkylamino; or E is hydrogen or phenyl optionally mono- to tri-substituted with substituents selected from the group comprising $C_{1-8}$-alkyl, $C_{1-8}$-alkoxy, $C_{3-8}$-alkenyloxy, $C_{3-8}$-alkynyloxy, phenyl-$C_{1-6}$-alkyloxy, phenyl-$C_{3-6}$-alkenyloxy, phenyl-$C_{3-6}$-alkynyloxy, $C_{1-8}$-alkylthio, $C_{3-8}$cycloalkyl-$C_{3-6}$-alkynyloxy, $C_{1-8}$-alkoxycarbonyl, $C_{1-8}$-haloalkoxy, $C_{3-8}$-haloalkenyloxy, halogen and cyano, wherein the phenyl groups may be optionally mono- to tri-substituted with substituents selected from the group comprising $C_{1-4}$-alkyl, $C_{1-4}$-alkoxy, $C_{1-4}$-alkylthio, $C_{1-4}$-haloalkyl, $C_{1-4}$-haloalkoxy, $C_{1-4}$-haloalkylthio, halogen and cyano; or E is hydrogen or phenyl optionally di- to tri-substituted with substituents selected from the group comprising $C_{1-8}$-alkyl, $C_{1-8}$-alkoxy, $C_{3-8}$-alkenyloxy, $C_{3-8}$-alkynyloxy, phenyl-$C_{1-6}$-alkyloxy, phenyl-$C_{3-6}$-alkenyloxy, phenyl-$C_{3-6}$-alkynyloxy, $C_{1-8}$-alkylthio, $C_{3-8}$cycloalkyl-$C_{3-6}$-alkynyloxy, $C_{1-8}$-alkoxycarbonyl, $C_{1-8}$-haloalkoxy, $C_{3-8}$-haloalkenyloxy, halogen and cyano, wherein the phenyl groups may be optionally mono- to tri-substituted with substituents selected from the group comprising $C_{1-4}$-alkyl, $C_{1-4}$-alkoxy, $C_{1-4}$-alkylthio, $C_{1-4}$-haloalkyl, $C_{1-4}$-haloalkoxy, $C_{1-4}$-haloalkylthio, halogen and cyano; or E is hydrogen or a group

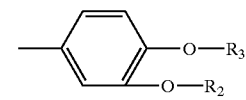

wherein $R_2$ is $C_{1-4}$-alkyl, and $R_3$ is $C_{1-8}$-alkyl, $C_{3-8}$-alkenyl, $C_{3-8}$-alkynyl, phenyl-$C_{1-6}$-alkyl, phenyl-$C_{3-6}$-alkenyl, phenyl-$C_{3-6}$-alkynyl, $C_{3-8}$cycloalkyl-$C_{3-6}$-alkynyl, $C_{1-8}$-halogenalkyl or $C_{3-8}$-halogenalkenyl wherein in each of the preceding radicals the phenyl groups may be optionally substituted with 1 to 3 substituents selected from the group comprising $C_{1-4}$-alkyl, $C_{1-4}$-alkoxy, $C_{1-4}$-alkylthio, $C_{1-4}$-haloalkyl, $C_{1-4}$-haloalkoxy, $C_{1-4}$-haloalkylthio, halogen and cyano; or R is hydrogen or $C_{1-10}$-alkyl, $C_{2-10}$-alkenyl, $C_{2-10}$-alkynyl, $C_{3-8}$-cycloalkyl, $C_{3-8}$-cycloalkyl-$C_{1-6}$-alkyl, $C_{6-10}$-aryl or $C_{6-10}$-aryl-$C_{1-6}$-alkyl, wherein each of the preceding groups may be optionally mono- or poly-substituted with substituents selected from the group comprising $C_{1-8}$-alkyl, $C_{2-8}$-alkenyl, $C_{2-8}$-alkynyl, $C_{3-6}$-cycloalkyl, $C_{3-8}$-cycloalkyl-$C_{1-6}$-alkyl, $C_{1-8}$-alkoxy, $C_{3-8}$-alkenyloxy, $C_{3-8}$-alkynyloxy, $C_{1-8}$-alkylthio, $C_{1-8}$-alkylsulfonyl, $C_{1-8}$-alkanoyl, $C_{1-8}$-alkoxycarbonyl, $C_{3-8}$-alkenyloxycarbonyl and $C_{3-8}$-alkynyloxycarbonyl wherein each of the alkyl, alkenyl, alkynyl or cycloalkyl parts of the preceding substituents may be partially or fully halogenated; halogen, nitro and cyano; or R is $C_{1-10}$-alkyl, $C_{2-10}$-alkenyl or $C_{3-8}$-cycloalkyl, wherein each of the preceding groups may be optionally mono- or poly-substituted with substituents selected from the group comprising $C_{1-8}$-alkyl, $C_{1-8}$-alkoxy, $C_{1-8}$-alkylthio, $C_{1-8}$-alkanoyl, $C_{1-8}$-alkoxycarbonyl, $C_{1-8}$-haloalkyl, $C_{1-8}$-haloalkoxy, $C_{1-8}$-haloalkylthio, halogen, nitro and cyano; or R is $C_{1-6}$-alkyl, $C_{2-6}$-alkenyl or $C_{5-6}$-cycloalkyl, wherein each of the preceding groups may be optionally mono- or poly-substituted with substituents selected from the group comprising $C_{1-4}$-alkyl, $C_{1-4}$-alkoxy, $C_{1-4}$-alkoxycarbonyl, $C_{1-4}$-haloalkyl, halogen and cyano; or R is straight-chain or branched $C_{1-4}$-alkyl, $C_{2-6}$-alkenyl or $C_{5-6}$-cycloalkyl, wherein each of the preceding groups may be optionally mono- or poly-substituted with F, Cl or Br.

Examples of substituents of cycloalkyl, cycloalkenyl, aryl or heteroaryl groups are: alkyl, alkenyl, alkynyl, cycloalkyl, cycloalkyl-alkyl, phenyl and phenyl-alkyl, it being possible in turn for all of the preceding groups to carry one or more identical or different halogen atoms; alkoxy; alkenyloxy; alkynyloxy; alkoxyalkyl; haloalkoxy, alkylthio; haloalkylthio; alkylsulfonyl; formyl; alkanoyl; hydroxy; halogen; cyano; nitro; amino; alkylamino; dialkylamino; carboxy; alkoxycarbonyl; alkenyloxycarbonyl; alkynyloxycarbonyl.

In the above definitions "halogen" includes fluorine, chlorine, bromine and iodine.

The alkyl, alkenyl and alkynyl radicals may be straight-chain or branched. This applies also to the alkyl, alkenyl or alkynyl parts of other alkyl-, alkenyl- or alkynyl-containing groups.

Depending upon the number of carbon atoms mentioned, alkyl on its own or as part of another substituent is to be understood as being, for example, methyl, ethyl, propyl, butyl, pentyl, hexyl, heptyl, octyl, nonyl, decyl, undecyl, dodecyl and the isomers thereof, for example isopropyl, isobutyl, tert-butyl or sec-butyl, isopentyl or tert-pentyl.

Cycloalkyl is, depending upon the number of carbon atoms mentioned, cyclopropyl, cyclobutyl, cyclopentyl, cyclohexyl, cycloheptyl or cyclooctyl. Cycloalkenyl preferably includes cyclopentenyl, cyclohexenyl and cycloheptenyl; the double bond being in any possible position of the ring including the binding position.

The alkylene bridge under the definition of B may be straight chain or branched. Preferred embodiments are 1,2-ethylene and 1,2-propylene.

Depending upon the number of carbon atoms mentioned, alkenyl as a group or as a structural element of other groups is to be understood as being, for example, ethenyl, allyl, 1-propenyl, buten-2-yl, buten-3-yl, penten-1-yl, penten-3-yl, hexen-1-yl, 4-methyl-3-pentenyl or 4-methyl-3-hexenyl.

Alkynyl as a group or as a structural element of other groups is, for example, ethynyl, propyn-1-yl, propyn-2-yl, butyn-1-yl, butyn-2-yl, 1-methyl-2-butynyl, hexyn-1-yl, 1-ethyl-butynyl or octyn-1-yl.

A haloalkyl group may contain one or more (identical or different) halogen atoms, and for example may stand for $CHCl_2$, $CH_2F$, $CCl_3$, $CH_2Cl$, $CHF_2$, $CF_3$, $CH_2CH_2Br$, $C_2Cl_5$, $CH_2Br$, $CHClBr$, $CF_3CH_2$, etc.

The presence of at least one asymmetric carbon atom and/or at least one asymmetric oxidized sulfur atom in the compounds of formula I means that the compounds may occur in optically isomeric forms. As a result of the presence of a possible aliphatic C=C and C=N double bond, geometric isomerism may also occur. Formula I is intended to include all those possible isomeric forms and mixtures thereof.

Further preferred subgroups of the compounds of formula I are those wherein

A is phenyl, naphthyl, cycloalkyl, cycloalkenyl or mono- or bicyclic heteroaryl comprising five- or six-membered rings containing 1 to 4 identical or different heteroatoms selected from oxygen, nitrogen or sulfur, wherein each of the cycles is optionally mono- or poly-substituted by substituents selected from the group comprising $C_{1-8}$-alkyl, $C_{2-8}$-alkenyl, $C_{2-8}$-alkynyl, $C_{3-8}$-cycloalkyl, $C_{3-8}$-cycloalkyl-$C_{1-6}$-alkyl, $C_{1-8}$-alkoxy, $C_{3-8}$-alkenyloxy, $C_{3-8}$-alkynyloxy, $C_{3-8}$-cycloalkyloxy, $C_{1-8}$-alkylthio, $C_{1-8}$-alkylsulfonyl, $C_{1-8}$-alkanoyl, $C_{1-8}$-alkanoyloxy, $C_{1-8}$-alkoxycarbonyl, $C_{3-8}$-alkenyloxycarbonyl, $C_{3-8}$-alkynyloxycarbonyl, $C_{1-8}$-dialkylamino, $C_{1-8}$-alkylamino, $C_{1-8}$-hydroximinoalkyl and $C_{1-8}$-alkoximinoalkyl, wherein each of the alkyl, alkenyl, alkynyl moieties are straight-chain or branched and may in turn be optionally halogenated; halogen; nitro; cyano; hydroxy; amino; formyl; carboxyl; carbamoyl and thiocarbamoyl; or from the group comprising aryl, aryloxy, arylthio, aryl-$C_{1-4}$-alkyl, aryl-$C_{1-4}$-alkyloxy, aryl-$C_{1-4}$-alkylthio, heterocyclyl, heterocyclyloxy, heterocyclylthio, heterocyclyl-$C_{1-4}$-alkyl, heterocyclyl-$C_{1-4}$-alkoxy and heterocyclyl-$C_{1-4}$-alkylthio, wherein each of the groups may be substituted with halogen, cyano, $C_{1-4}$-alkyl, $C_{1-4}$-alkoxy or $C_{1-4}$-alkylthio, wherein heterocyclyl comprises mono- or bicyclic five- or six-membered non-aromatic and aromatic rings containing 1 to 4 identical or different heteroatoms selected from oxygen, nitrogen or sulfur; or from the group comprising aryloxyalkyl, heteroaryloxyalkyl, arylalkyliminoxyalkyl, aryloxyiminoalkyl, arylalkyloxyiminoalkyl, aryloxyiminoalkyleniminoxyalkyl and aryl-alkyloxyiminoalkylen-iminoxyalkyl wherein each alkyl or alkylene may be straight-chain or branched and each aryl or heteroaryl may in turn be substituted with halogen, cyano, $C_{1-4}$-alkyl, $C_{1-4}$-alkoxy or $C_{1-4}$-alkylthio; and B is a direct bond or $C_{1-4}$-alkylene which is optionally substituted with substituents selected from the group comprising halogen, linear or branched $C_{1-6}$-alkyl, $C_{2-6}$-alkenyl or $C_{2-6}$-alkynyl and $C_{5-7}$-cycloalkyl, each in turn optionally substituted with 1–4 halogen atoms; and E is hydrogen or phenyl optionally mono- or poly-substituted with substituents selected from the group comprising $C_{1-8}$-alkyl, $C_{2-8}$-alkenyl, $C_{2-8}$-alkynyl, $C_{3-8}$-cycloalkyl, $C_{3-8}$-cycloalkyl-$C_{1-6}$alkyl, $C_{1-8}$-alkoxy, $C_{3-8}$-alkenyloxy, $C_{3-8}$-alkynyloxy, $C_{3-8}$-cycloalkyloxy, $C_{6-10}$-aryloxy, $C_{6-10}$-aryl-$C_{1-6}$-alkyloxy, $C_{6-10}$-aryl-$C_{3-6}$-alkenyloxy, $C_{6-10}$-aryl-$C_{3-6}$-alkynyloxy, $C_{1-8}$-alkanoyloxy, $C_{3-8}$cycloalkyl-$C_{3-6}$-alkynyloxy, $C_{1-8}$-alkylthio, $C_{1-8}$-alkylsulfonyl, $C_{1-8}$-alkanoyl, $C_{1-8}$-alkoxycarbonyl, $C_{3-8}$-alkinyloxycarbonyl and $C_{3-8}$-alkinyloxycarbonyl wherein in each of the preceding groups the alkyl, alkenyl, alkynyl or cycloalkyl part may be partially or fully halogenated and wherein the aryl groups may be optionally mono- or poly-substituted with substituents selected from the group comprising $C_{1-8}$-alkyl, $C_{2-8}$-alkenyl, $C_{3-8}$-cycloalkyl, $C_{1-8}$-alkoxy, $C_{1-8}$-alkylthio, $C_{1-8}$-alkoxycarbonyl, $C_{1-8}$-haloalkyl, $C_{1-8}$-haloalkoxy, $C_{1-8}$-haloalkylthio, halogen, nitro and cyano; halogen, nitro, cyano, hydroxy, amino, di-$C_{1-8}$-alkylamino and $C_{1-8}$-alkylamino; and R is hydrogen or $C_{1-10}$-alkyl, $C_{2-10}$-alkenyl, $C_{2-10}$-alkynyl, $C_{3-8}$-cycloalkyl, $C_{3-8}$-cycloalkyl-$C_{1-6}$-alkyl, $C_{6-10}$-aryl or $C_{6-10}$-aryl-$C_{1-6}$-alkyl, wherein each of the preceding groups may be optionally mono- or poly-substituted with substituents selected from the group comprising $C_{1-8}$-alkyl, $C_{2-8}$-alkenyl, $C_{2-8}$-alkynyl, $C_{3-8}$-cycloalkyl, $C_{3-8}$-cycloalkyl-$C_{1-6}$-alkyl, $C_{1-8}$-alkoxy, $C_{3-8}$-alkenyloxy, $C_{3-8}$-alkynyloxy, $C_{1-8}$-alkylthio, $C_{1-8}$-alkylsulfonyl, $C_{1-8}$-alkanoyl, $C_{1-8}$-alkoxycarbonyl, $C_{3-8}$-alkenyloxycarbonyl and $C_{3-8}$-alkynyloxycarbonyl wherein each of the alkyl, alkenyl, alkynyl or cycloalkyl parts of the preceding substituents may be partially or fully halogenated; halogen, nitro and cyano; or A is phenyl, naphthyl, furyl, thienyl, imidazolyl, thiazolyl, oxazolyl, pyridyl, pyrimidinyl, benzothiophenyl, benzthiazolyl, chinolinyl, pyrazolyl, indolyl, benzimidazolyl or pyrrolyl, each optionally-substituted by 1 to 3 substituents selected from the group comprising $C_{1-8}$-alkyl, $C_{2-8}$-alkenyl, $C_{3-8}$-cycloalkyl, $C_{1-8}$-alkoxy, $C_{1-8}$-alkylthio, $C_{1-8}$-alkoxycarbonyl, $C_{1-8}$-haloalkyl, $C_{1-8}$-haloalkoxy, $C_{1-8}$-haloalkylthio, halogen, nitro and cyano; or from the group comprising aryl, aryloxy, arylthio, aryl-$C_{1-4}$-alkyl, aryl-$C_{1-4}$-alkyloxy, aryl-$C_{1-4}$-alkylthio, heterocyclyl, heterocyclyloxy, heterocyclylthio, heterocyclyl-$C_{1-4}$-alkyl, heterocyclyl-$C_{1-4}$-alkoxy and heterocyclyl-$C_{1-4}$-alkylthio, wherein each of the groups may be substituted with halogen, cyano, $C_{1-4}$-alkyl, $C_{1-4}$-alkoxy or $C_{1-4}$-alkylthio, wherein heterocyclyl is furyl, thienyl, imidazolyl, thiazolyl, oxazolyl, pyridyl, pyrimidinyl, benzothiophenyl, benzthiazolyl, chinolinyl, pyrazolyl, indolyl, benzimidazolyl or pyrrolyl; or from the group comprising phenoxy-$C_{1-4}$-alkyl, phenyl-$C_{1-4}$-alkyliminoxy-$C_{1-4}$-alkyl and phenyl-alkoxyimino-$C_{2-4}$-alkyleniminoxy-$C_{1-4}$-alkyl wherein each alkyl or alkylene may be straight-chain or branched and each phenyl or phenoxy may in turn be substituted with halogen, cyano, $C_{1-4}$-alkyl, $C_{1-4}$-alkoxy or $C_{1-4}$-alkylthio; and B is a direct bond or $C_{1-4}$-alkylene which is optionally substituted with substituents selected from the group comprising F, Cl, Br, linear or branched $C_{1-4}$-alkyl, $C_{2-4}$-alkenyl or, $C_{2-4}$-alkynyl and $C_{5-7}$-cycloalkyl, each in turn optionally substituted with 1–4 halogen atoms; and E is hydrogen or phenyl optionally mono- to tri-substituted with substituents selected from the group comprising $C_{1-8}$-alkyl, $C_{1-8}$-alkoxy, $C_{3-8}$-alkenyloxy, $C_{3-8}$-alkynyloxy, phenyl-$C_{1-6}$-alkyloxy, phenyl-$C_{3-6}$-alkenyloxy, phenyl-$C_{3-6}$-alkynyloxy, $C_{3-8}$cycloalkyl-$C_{3-6}$-alkynyloxy, $C_{1-8}$-alkylthio, $C_{1-8}$-alkoxycarbonyl, $C_{1-8}$-haloalkoxy, $C_{3-8}$-haloalkenyloxy, halogen and cyano, wherein the phenyl groups may be optionally mono- to tri-substituted with substituents selected from the group comprising $C_{1-4}$-alkyl, $C_{1-4}$-alkoxy, $C_{1-4}$-alkylthio, $C_{1-4}$-haloalkyl, $C_{1-4}$-haloalkoxy, $C_{1-4}$-haloalkylthio, halogen and cyano; and R is $C_{1-10}$-alkyl, $C_{2-10}$-alkenyl or $C_{3-8}$-cycloalkyl, wherein each of the preceding groups may be optionally mono- or poly-substituted with substituents selected from the group comprising $C_{1-8}$-alkyl, $C_{1-8}$-alkoxy, $C_{1-8}$-alkylthio, $C_{1-8}$-alkanoyl, $C_{1-8}$-alkoxycarbonyl, $C_{1-8}$-haloalkyl, $C_{1-8}$-haloalkoxy, $C_{1-8}$-haloalkylthio, halogen, nitro and cyano; or A is phenyl, naphthyl, furyl, thienyl, imidazolyl, thiazolyl, oxazolyl, pyridyl, pyrimidinyl, pyrazolyl, indolyl, benzimidazolyl or pyrrolyl, each optionally-substituted by 1 to 3 substituents selected from the group comprising $C_{1-8}$-alkyl, $C_{2-8}$-alkenyl, $C_{3-8}$-cycloalkyl, $C_{1-8}$-alkoxy, $C_{1-8}$-alkylthio, $C_{1-8}$-alkoxycarbonyl, $C_{1-8}$-haloalkyl, $C_{1-8}$-haloalkoxy, $C_{1-8}$-haloalkylthio, halogen, nitro and cyano; or from the group comprising aryl, aryloxy, arylthio, heterocyclyl, heterocyclyloxy and heterocyclylthio, wherein each of the groups may be substituted with halogen, cyano, $C_{1-4}$-alkyl, $C_{1-4}$-alkoxy or $C_{1-4}$-alkylthio, wherein heterocyclyl is furyl, thienyl, imidazolyl, thiazolyl, oxazolyl, pyridyl, pyrimidinyl, pyrazolyl, indolyl or pyrrolyl; or from a group comprising phenoxy-$C_{1-4}$-alkyl, phenyl-$C_{1-4}$-alkyliminoxy-$C_{1-4}$-alkyl and phenyl-alkoxyimino-$C_{2-4}$-alkyleniminoxy-$C_{1-4}$-alkyl wherein each alkyl or alkylene may be straight-chain or branched and each phenyl or phenoxy may in turn be substituted with halogen, cyano, $C_{1-4}$-alkyl, $C_{1-4}$-alkoxy or $C_{1-4}$-alkylthio; and B is a direct bond or $C_{1-4}$-alkylene which is optionally substituted with substituents selected from the group comprising F, Cl, Br, linear or branched $C_{1-2}$-alkyl, $C_{2-3}$-alkenyl or, $C_{2-3}$-alkynyl and $C_{5-7}$-cycloalkyl, each in turn optionally substituted with 1–4 halogen atoms; and E is hydrogen or phenyl optionally di- to tri-substituted with substituents selected from the group comprising $C_{1-8}$-alkyl, $C_{1-8}$-alkoxy, $C_{3-8}$-alkenyloxy, $C_{3-8}$-alkynyloxy, phenyl-$C_{1-6}$-alkyloxy, phenyl-$C_{3-6}$-alkenyloxy, phenyl-$C_{3-6}$-alkynyloxy, $C_{3-8}$cycloalkyl-$C_{3-6}$-alkynyloxy, $C_{1-8}$-alkylthio, $C_{1-8}$-alkoxycarbonyl, $C_{1-8}$-haloalkoxy, $C_{3-8}$-haloalkenyloxy, halogen and cyano, wherein the phenyl groups may be optionally mono- to tri-substituted with substituents selected from the group comprising $C_{1-4}$-alkyl, $C_{1-4}$-alkoxy, $C_{1-4}$-alkylthio, $C_{1-4}$-haloalkyl, $C_{1-4}$-haloalkoxy, $C_{1-4}$-haloalkylthio, halogen and cyano; and R is $C_{1-6}$-alkyl, $C_{2-6}$-alkenyl or $C_{5-6}$-cycloalkyl, wherein each of the preceding groups may be optionally mono- or poly-substituted with substituents selected from the group comprising $C_{1-4}$-alkyl, $C_{1-4}$-alkoxy, $C_{1-4}$-alkoxycarbonyl, $C_{1-4}$-haloalkyl, halogen and cyano; or A is phenyl, naphthyl, furyl, thienyl, imidazolyl, thiazolyl, oxazolyl, pyridyl, pyrimidinyl, pyrazolyl or pyrrolyl, each optionally-substituted by 1 to 3 substituents selected from the group comprising $C_{1-4}$-alkyl, $C_{2-6}$-alkenyl, $C_{3-6}$-cycloalkyl, $C_{1-4}$-alkoxy, $C_{1-4}$-alkylthio, $C_{1-4}$-alkoxycarbonyl, $C_{1-4}$-haloalkyl, $C_{1-4}$-haloalkoxy, $C_{1-4}$-haloalkylthio, halogen, nitro and cyano; or from the group comprising aryl, aryloxy, arylthio, heterocyclyl, heterocyclyloxy and heterocyclylthio, wherein each of the groups may be substituted with halogen, cyano, $C_{1-4}$-alkyl, $C_{1-4}$-alkoxy or $C_{1-4}$-alkylthio, wherein heterocyclyl is furyl, thienyl, imidazolyl, thiazolyl, oxazolyl, pyridyl, pyrimidinyl, pyrazolyl, indolyl or pyrrolyl; and B is a direct bond, methylene, 1,1-ethylene, 1,2-ethylene, 1,1-propylene, 1,2-propylene, 1,3-propylene or 2,2-propylene; and E is hydrogen or a group

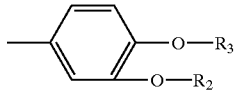

wherein $R_2$ is $C_{1-4}$-alkyl, and $R_3$ is $C_{1-8}$-alkyl, $C_{3-8}$-alkenyl, $C_{3-8}$-alkynyl, phenyl-$C_{1-6}$-alkyl, phenyl-$C_{3-6}$-alkenyl, phenyl-$C_{3-6}$-alkynyl, $C_{3-8}$cycloalkyl-$C_{3-6}$-alkynyl, $C_{1-8}$-halogenalkyl or $C_{3-8}$-halogenalkenyl wherein in each of the preceding radicals the phenyl groups may be optionally substituted with 1 to 3 substituents selected from the group comprising $C_{1-4}$-alkyl, $C_{1-4}$-alkoxy, $C_{1-4}$-alkylthio, $C_{1-4}$-haloalkyl, $C_{1-4}$-haloalkoxy, $C_{1-4}$-haloalkylthio, halogen and cyano; and R is straight-chain or branched $C_{1-4}$-alkyl, $C_{2-6}$-alkenyl or $C_{5-6}$-cycloalkyl, wherein each of the preceding groups may be optionally mono- or poly-substituted with F, Cl or Br; and T is NH; or A is phenyl, naphthyl, cycloalkyl, cycloalkenyl or mono- or bicyclic heteroaryl comprising five- or six-membered rings containing 1 to 4 identical or different heteroatoms selected from oxygen, nitrogen or sulfur, wherein each of the cycles is optionally substituted by substituents selected from the group comprising aryloxyalkyl, heteroaryloxyalkyl, aryloxy-heteroaryloxy, arylalkyliminoxyalkyl, aryloxyiminoalkyl, arylalkyloxyiminoalkyl, aryloxy-iminoalkyleniminoxyalkyl and aryl-alkyloxyiminoalkyleniminoxyalkyl wherein each alkyl or alkylene may be straight-chain or branched and each alkyl, alkylene, aryl or heteroaryl may in turn be substituted with halogen, cyano, $C_{1-4}$-alkyl, $C_{1-4}$haloalkyl, $C_{1-4}$-alkoxy, $C_{1-4}$-haloalkoxy, or $C_{1-4}$-alkylthio; and B is a direct bond or $C_{1-4}$-alkylene; and E is hydrogen; and R is hydrogen or $C_{1-10}$-alkyl; or A is phenyl, thienyl, imidazolyl, pyridyl, pyrimidinyl, pyrazolyl or pyrrolyl, each optionally-substituted by a substituent selected from the group comprising phenoxy-$C_{1-4}$-alkyl, phenyl-$C_{1-4}$-alkyliminoxy-$C_{1-4}$-alkyl and phenyl-alkoxyimino-$C_{2-4}$-alkyleniminoxy-$C_{1-4}$-alkyl wherein each alkyl or alkylene may be straight-chain or branched and each phenyl or phenoxy may in turn be substituted with halogen, cyano, $C_{1-4}$-alkyl, $C_{1-4}$-alkoxy or $C_{1-4}$-alkylthio; and B is $C_{1-4}$-alkylene; and E is hydrogen; and R is straight-chain or branched $C_{1-4}$-alkyl; or A is phenyl substituted by phenoxy-$C_{1-4}$-alkyl, phenyl-$C_{1-4}$-alkyliminoxy-$C_{1-4}$-alkyl or phenyl-alkoxyimino-$C_{2-4}$-alkyleniminoxy-$C_{1-4}$-alkyl wherein each alkyl or alkylene may be straight-chain or branched and each phenyl or phenoxy may in turn be substituted with halogen, cyano, $C_{1-4}$-alkyl, $C_{1-4}$-alkoxy or $C_{1-4}$-alkylthio; and B is methylene; and E is hydrogen; and R is methyl or ethyl.

Preferred individual compounds are:

2-(3,4-dichloro-phenyl)-N-[2-(4-ethoxy-3-methoxy-phenyl)-ethyl]-2-methylthioimino-acetamide, 2-(3,4-dichloro-phenyl)-N-[2-(3-methoxy-4-prop-2-ynyloxy-phenyl)-ethyl]-2-methylthioimino-acetamide, 2-(3,4-dichloro-phenyl)-N-[2-(3-methoxy-4-pent-2-ynyloxy-phenyl)-ethyl]-2-methylthioimino-acetamide, N-[2-(4-allyloxy-3-methoxy-phenyl)-ethyl]-2-(3,4-dichloro-phenyl)-2-methylthioimino-acetamide, N-[2-(3-methoxy-4-prop-ynyloxy-phenyl)-ethyl]-2-methylthioimino-2-(4-tolyl)-acetamide, 2-(4-bromo-phenyl)-N-[2-(3-methoxy-4-prop-2-ynyloxy-phenyl)-ethyl]-2-methylthioimino-acetamide, 2-(4-chloro-phenyl)-N-[2-(3-methoxy-4-prop-2-ynyloxy-phenyl)-ethyl]-2-methylthioimino-acetamide, N-[2-(3-methoxy-4-prop-ynyloxy-phenyl)-ethyl]-2-naphthalen-2-yl-2-methylthioimino-2-acetamide, 2-(4-fluoro-phenyl)-N-[2-(3-methoxy-4-prop-2-ynyloxy-phenyl)-ethyl]-2-methylthioimino-acetamide, 2-(4-methoxy-phenyl)-N-[2-(3-methoxy-4-prop-2-ynyloxy-phenyl)-ethyl]-2-methylthioimino-acetamide, N-[2-(3-methoxy-4-prop-ynyloxy-phenyl)-ethyl]-2-(3,4-dichloro-phenyl)-2-ethylthioimino-2-(4-tolyl)-acetamide, N-methyl-2-methylthioimino-2-{2-[1-(trifluoromethyl-phenyl)-ethylideneaminooxymethyl]-phenyl}-acetamide, 2-methylthioimino-2-{2-[1-(trifluoromethyl-phenyl)-ethylideneaminooxymethyl]-phenyl}-acetic acid methyl ester, 2-{2-[1-(4-chloro-phenyl)-ethylideneaminooxymethyl]-phenyl}-N-methyl-2-methylthioimino-acetamide, 2-{2-[1-(4-chloro-phenyl)-ethylideneaminooxymethyl]-phenyl}-2-methylthioimino-acetic acid methyl ester, 2-[4-(4-methyl-phenyl)-phenyl]-N-[2-(3,4-di-methoxy-phenyl)-ethyl]-2-methylthioimino-acetamide, 2-[4-(3,4-dichloro-phenyl)-phenyl]-N-[2-(3,4-di-methoxy-phenyl)-ethyl]-2-methylthioimino-acetamide, 2-[4-(4-chloro-phenyl)-phenyl]-N-[2-(3,4-di-methoxy-phenyl)-ethyl]-2-methylthioimino-acetamide, 2-[4-(4-trifluoromethyl-phenyl)-phenyl]-N-[2-(3,4-di-methoxy-phenyl)-ethyl]-2-methylthioimino-acetamide, 2-[4-(4-trifluoromethoxy-phenyl)-phenyl]-N-[2-(3,4-di-methoxy-phenyl)-ethyl]-2-methylthio-imino-acetamide, 2-[4-(4-tert.-butyl-phenyl)-phenyl]-N-[2-(3,4-di-methoxy-phenyl)-ethyl]-2-methylthioimino-acetamide and, 2-(4-biphenylyl)-N-[2-(3,4-di-methoxy-phenyl)-ethyl]-2-methylthioimino-acetamide.

The α-sulfenimino acid derivatives of formula I may be obtained according to one of the following processes:

a)

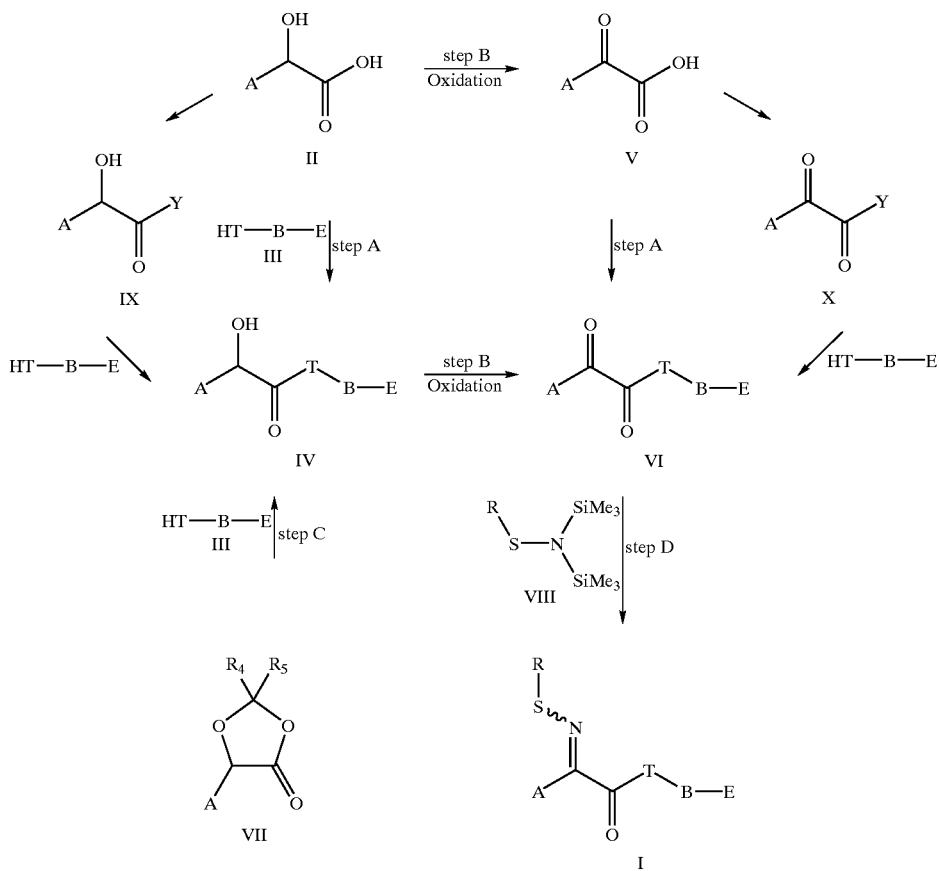

Step A: A α-hydroxy acid of formula II or a α-keto-acid of the formula V wherein A is as defined for formula I, is reacted at a temperature between +150° C. and +250° C. in the presence of an excess of an alcohol or amine of formula III, wherein B, E and T are as defined for formula I, and in the presence of an acidic catalyst as p-toluenesulfonic acid.

The reaction conditions correspond to those known for esterifications and amidations, e.g. as described in WO 94/29267. Alternatively, the acids compounds of formulae II or V may be transformed to amides of formulae IV or VI in the presence of activating reagents as e.g. described below for the process b) of Step D.

Step B: The α-hydroxy acid of formula II or the α-hydroxy acid derivative of formula IV where A, E, B and T are as defined for formula I, is oxidized by reaction with an organic oxidizing agent (e.g. an alkyl hydroperoxyde, a DMSO-based reagent as described by T. T. Tidwell, *Org. React.*, 1990, 39, 297–572, a hypervalent iodine reagent, a dioxirane, a nitroxyl radical, or an inorganic oxidizing agent (e.g. peroxides, hypochlorites, transition metal oxide of e.g. Cr, Mn, Ru, Re, Os, sodium percarbonate, sodium perborate, silver carbonate).

The oxidation reaction is preferably conducted in an inert solvent, such as THF, $CH_2Cl_2$, water or a ketone, for example acetone, or in a mixtures thereof, in the absence or in the presence of an acid or in the presence or in the absence of a base, at temperatures between −80° C. +150° C.

Step C: A dioxolanone of the formula VII wherein A is as defined for formula I and $R_4$ and $R_5$ independently of each are hydrogen, $C_1$–$C_8$-alkyl or $C_1$–$C_8$-haloalkyl or $R_4$ and $R_5$ together with the carbon atom to which they are attached may form a 5-, 6- or 7-membered saturated, partially unsaturated or unsaturated isocyclic ring is reacted with an alcohol or amine of formula III, wherein B, E and T are as defined for formula I.

The reaction conditions are in analogy to known procedures (e.g. A. Khalaj, E. Nahid, *Synthesis*, 1985, 1153). The reaction is carried out in an inert solvent, e.g. toluene, xylene, THF, chlorobenzene hexane or heptane, at temperature between 0° C. and +200° C.

Step D: An α-keto acid derivative of formula VI, wherein A, B, E and T are as defined for formula I, is treated with a N,N-bis(silyl)sulfenamide of the formula VIII, where R is as defined for formula I, (c.f. T. Morimoto, Y. Nezu, K. Achiwa, M. Sekiya, *J. Chem. Soc. Chem. Commun.* 1985, 1584) in an inert solvent as THF, ether, glyme, at temperature between −40 and +150° C. in the presence of a catalyst, e.g. fluoride source as tert.-butylammonium fluoride, HF, KF or $LiBF_4$ and/or in the presence or in the absence of an acid, a Lewis acid or a base.

In alternative routes of conducting the above scheme a) the α-hydroxy acid of formula II and of the α-keto acid of formula V may first be converted into the activated forms of the acids, e.g. into lower esters or acid halides of formulae IX and X wherein Y is alkoxy, benzyloxy, phenoxy, F, Cl, or Br, by reacting II or V with lower alcohols (typically methanol, ethanol, propanol, isopropanol, butanol, sec-butanol, tert-butanol, phenol, benzylalcohol) or with a halogenating agent to form acid halides (fluorides, chlorides or bromides).

The reaction conditions for the formation of the activated derivatives IX and X are as commonly known for esterification or halogenation steps.

b)

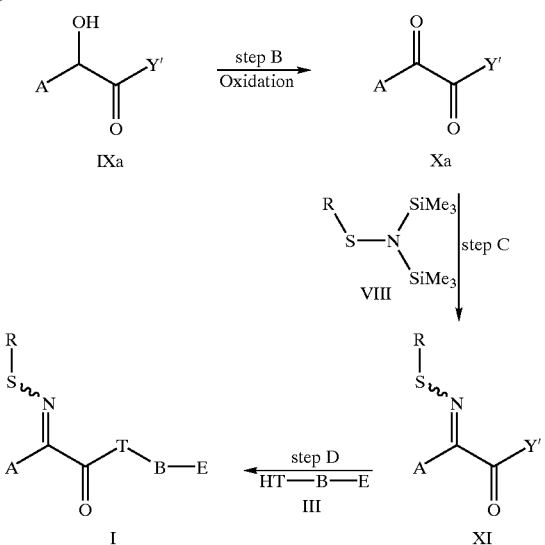

Step B: procedure is the same as in step B of process a). Y' is as defined for Y for formulae IX or X in Scheme a) or is OH.
Step C: procedure is the same as in step D of process a). Y' is as defined for Y for formulae IX or X in Scheme a) or is OH.
Step D: compounds of formula XI' (A and R are as defined for formula I and Y' is as defined for Y for formulae IX or X in scheme a) or is OH ) are treated with an alcohol or an amine of formula III, wherein B, E and T are as in formula I, in an inert solvent or without solvent in the presence or in the absence of an acid scavenger (e.g. a base as Na-alcoholate, K-alcoholate, triethylamine, diethyl-isopropylamine) at temperatures between −20° C. and +200° C., preferably at reflux temperature in alcohols.
Step D may become of special importance in those cases wherein the radical —T—B—E is sensitive to the thioiminolation reagent of formula VIII. Also compounds of the subformula Ia wherein T is NH are advantageously made from the activated compounds of formula XI by the procedure of step D.

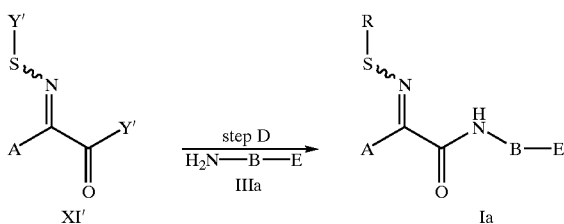

Where Y' is OH this step may further be facilitated by converting the acid function into an activated carboxyl group like an acid halide (halide=fluoride, chloride, bromide), like symmetrical or mixed anhydrides, such as mixed anhydrides with O-alkylcarbonates, like activated esters, such as p-nitrophenylesters or N-hydroxysucinimidesters, as well as in situ produced activated forms with condensating agents, such as dicyclohexylcarbodiimid, carbonyldiimidazol, benzotriazol-1-yloxy-tris(dimethylamino)phosphonium hexafluorophosphate, O-benzotriazol-1-yl N,N,N',N'-bis(pentamethylene)uronium hexafluorophosphate, O-benzotriazol-1-yl N,N,N',N'-bis(tetramethylene)uronium hexafluorophosphate, O-benzotriazol-1-yl N,N,N',N'-tetramethyluronium hexafluorophosphate or benzotriazol-1-yloxy-tripyrrolidinophosphonium hexafluorophosphate. The mixed anhydrides can be prepared by reaction of compounds of formula XI' wherein Y' is OH with chloroformic acid esters like chloroformic acid alkylesters, such as ethyl chloroformate or isobutyl chloroformate, optionally in the presence of an organic or inorganic base like a tertiary amine, such as triethylamine, N,N-diisopropyl-ethylamine, pyridine, n-methyl-piperidine or N-methyl-morpholin. The reaction is performed in a solvent like aromatic, non-aromatic or halogenated hydrocarbons, such as chlorohydrocarbons e.g. dichloromethane or toluene; ketones e.g. acetone; esters e.g. ethyl acetate; amides e.g. N,N-dimethylformamide; nitriles e.g. acetonitrile; or ethers e.g. diethylether, tert-butyl-methylether, dioxane or tetrahydrofurane. It is also possible to use mixtures of these solvents. The reaction may be performed optionally in the presence of an organic or inorganic base like NaH, KH, a tertiary amine, such as triethylamine, N,N-diisopropyl-ethylamine, pyridine, n-methyl-piperidine or N-methyl-morpholin at temperatures ranging from −80° C. to +150° C., preferably at temperatures ranging from −40° C. to +40° C.

c)

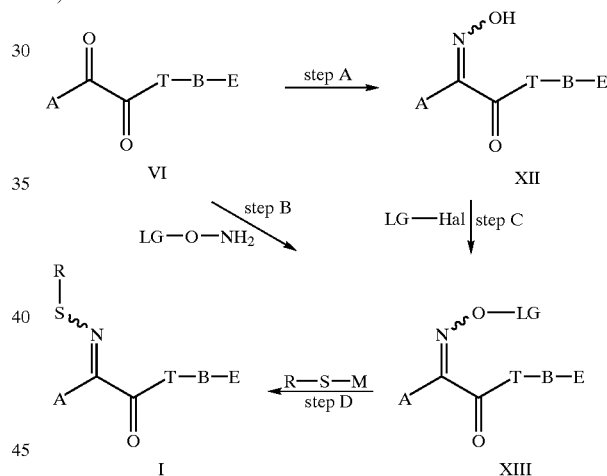

Step A: A compound of formula VI wherein A, B, E and T are as defined for in formula I is transformed to a compound of formula XII under standard oximation conditions as described in J. March, *Advanced Organic Chemistry*, 4th ed., Wiley, 1992.
Step B A compound of formula VI wherein A, B, E and T are as defined for in formula I is reacted with LG—O—NH$_2$, where LG is a leaving group, typically tosyl or mesyl, under classical oximation conditions as described by e.g. J. March, *Advanced Organic Chemistry*, 4th ed., Wiley, 1992 to give a compound of formula XIII wherein A, B, E and T are as defined for formula I.
Step C: An oxime of the formula XII wherein A, B, E and T are as defined for in formula I is reacted with LG-Hal, where Hal is a halogen, typically F, Cl, Br, or OH and LG a leaving group as defined above. The reaction conditions are as for the esterification or amidation process used in step D of process b).
Step D: A compound of formula XIII, wherein A, B, E and T are as defined for in formula I and LG is as defined above is reacted with a compound of the formula R—S—M wherein R is as defined for formula I and M is a alkaline metal cation such as Li, Na or K in an inert solvent (e.g. THF, DMF, glyme, diglyme) and in the presence of a base (e.g. tertiary amines like triethylamine or ethyldipropylamine, or alcoholates) at a temperature between +20° C. and +150° C. to give the compound of formula I.

Compounds of formula Xi are partly encompassed in formula I. Those compounds wherein Y is an alcoholic moiety are encompassed within formula I and exhibit favourable biological activities. Those compounds of formula XI' wherein Y' is halogen or OH serve as intermediates in the synthesis.

For compounds of formula I wherein T is NH also the following synthesis passway is suitable:

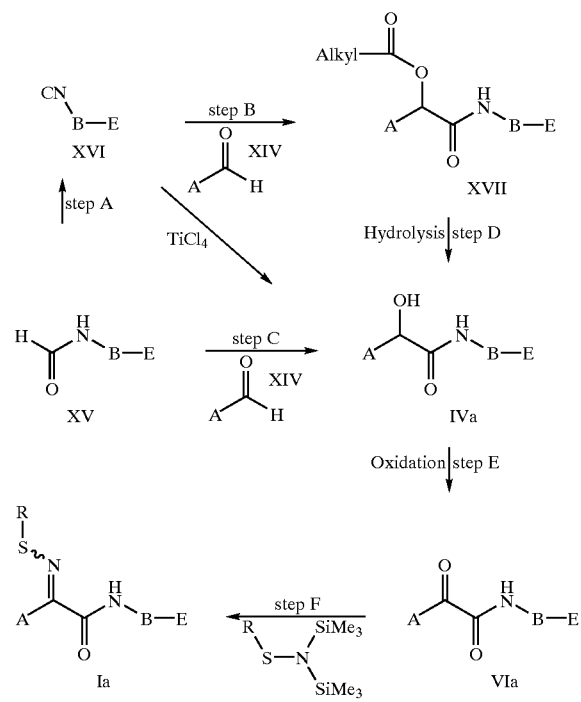

Step A: A N-formylamine of the formula XV wherein B and E are as defined for in formula I is dehydrated to an isocyanide of formula XVI under known conditions, as described e.g. in D. Seebach, G. Adam, T. Gees, M. Schiess, W. Weigang, *Chem. Ber.* 1988, 121, 507.

Step D B: An isocyanide of formula XVI wherein B and E are as defined for formula I, is reacted with an aldehyde of formula XIV, wherein A is as in formula I in the presence of a carboxylic acid (typically acetic acid) to give a O-acyl-α-hydroxy amide of formula XVII wherein A, B and E are as defined for in formula I and Alkyl is lower alkyl, preferably methyl.

The reaction conditions for this so-called "three-component-Passerini-Reaction are described in J. March, *Advanced Organic Chemistry*, 4th ed., Wiley, 1992, p. 980.

Alternatively an isocyanide of formula XVI wherein B and E are as defined for formula I is reacted with an aldehyde of formula XIV in the presence of titanium tetrachloride to give directly the α-hydroxy amide of the formula IVa wherein A, B and E are as defined for in formula I. The principle reaction conditions are similar to those described in *Chem. Ber.* 1988, 121, 507; and O. Ort et al. *Pesticide Sci.* 1997, 50, 331.

Step C: A N-formylamine of formula XV wherein B and E are as defined for formula I is treated with a phosgene equivalent (e.g. triphosgene) and a base (e.g. triethylamine) and in a second step without isolation of the isocyanide intermediate is further treated with titanium tetrachloride and an aldehyde of formula XIV wherein A is as in formula I. Reaction conditions for such reaction are as the conditions in WO 96/17840. In the resulting α-hydroxy amide of the formula IVa the radicals A, B and E are as in formula I.

Step D: An O-acyl-α-hydroxy amide of formula XVII is saponified to a an α-hydroxy amide of formula IVa under classical conditions for hydrolysis (c.f. to e.g. J. March, *Advanced Organic Chemistry*, 4th ed., Wiley, 1992).

Step E: same conditions as in step B of process a).

Step F: same conditions as in step D of process a).

The compounds of formula I are oils or solids at room temperature and are distinguished by valuable microbicidal properties. They can be used in the agricultural sector or related fields preventively and curatively in the control of plant-destructive microorganisms. The compounds of formula I according to the invention are distinguished at low rates of concentration not only by outstanding microbicidal, especially fungicidal, activity but also by being especially well tolerated by plants.

Surprisingly, it has now been found that the compounds of formula I have for practical purposes a very advantageous biocidal spectrum in the control of phytopathogenic microorganisms, especially fungi. They possess very advantageous curative and preventive properties and are used in the protection of numerous crop plants. With the compounds of formula I it is possible to inhibit or destroy phytopathogenic microorganisms that occur on various crops of useful plants or on parts of such plants (fruit, blossom, leaves, stems, tubers, roots), while parts of the plants which grow later also remain protected, for example, against phytopathogenic fungi.

The novel compounds of formula I prove to be effective against specific genera of the fungus class Fungi imperfecti (e.g. Cercospora), Basidiomycetes (e.g. Puccinia) and Ascomycetes (e.g. Erysiphe and Venturia) and especially against Oomycetes (e.g. Plasmopara, Peronospora, Pythium and Phytophthora). They therefore represent in plant protection a valuable addition to the compositions for controlling phytopathogenic fungi. The compounds of formula I can also be used as dressings for protecting seed (fruit, tubers, grains) and plant cuttings from fungal infections and against phytopathogenic fungi that occur in the soil.

The invention relates also to compositions comprising compounds of formula I as active ingredient, especially plant-protecting compositions, and to the use thereof in the agricultural sector or related fields.

In addition, the present invention includes the preparation of those compositions, wherein the active ingredient is homogeneously mixed with one or more of the substances or groups of substances described herein. Also included is a method of treating plants which is distinguished by the application of the novel compounds of formula I or of the novel compositions.

Target crops to be protected within the scope of this invention comprise, for example, the following species of plants: cereals (wheat, barley, rye, oats, rice, maize, sorghum and related species); beet (sugar beet and fodder beet); pomes, stone fruit and soft fruit (apples, pears, plums, peaches, almonds, cherries, strawberries, raspberries and blackberries); leguminous plants (beans, lentils, peas, soybeans); oil plants (rape, mustard, poppy, olives, sunflowers, coconut, castor oil plants, cocoa beans, groundnuts); cucurbitaceae (marrows, cucumbers, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocado, cinnamon, camphor) and plants such as tobacco, nuts, coffee, sugar cane, tea, pepper, vines, hops, bananas and natural rubber plants, and also ornamentals.

The compounds of formula I are normally used in the form of compositions and can be applied to the area or plant to be treated simultaneously or in succession with other active ingredients. Those other active ingredients may be fertilisers, micronutrient donors or other preparations that influence plant growth. It is also possible to use selective herbicides or insecticides, fungicides, bactericides, nematicides, molluscicides or mixtures of several of those preparations, if desired together with further carriers, surfactants or other application-promoting adjuvants customarily employed in formulation technology.

The compounds of formula I can be mixed with other fungicides, resulting in some cases in unexpected synergistic activities.

Mixing components which are particularly preferred are azoles such as azaconazole, bitertanol, propiconazole, difenoconazole, diniconazole, cyproconazole, epoxiconazole, fluquinconazole, flusilazole, flutriafol, hexaconazole, imazalil, imibenconazole, ipconazole, tebuconazole, tetraconazole, fenbuconazole, metconazole, myclobutanil, perfurazoate, penconazole, bromuconazole, pyrifenox, prochloraz, triadimefon, triadimenol, triflumizole or triticonazole; pyrimidinyl carbinoles such as ancymidol, fenarimol or nuarimol; 2-amino-pyrimidine such as bupirimate, dimethirimol or ethirimol; morpholines such as dodemorph, fenpropidin, fenpropimorph, spiroxamin or tridemorph; anilinopyrimidines such as cyprodinil, pyrimethanil or mepanipyrim; pyrroles such as fenpiclonil or fludioxonil; phenylamides such as benalaxyl, furalaxyl, metalaxyl, R-metalaxyl, ofurace or oxadixyl; benzimidazoles such as benomyl, carbendazim, debacarb, fuberidazole or thiabendazole; dicarboximides such as chlozolinate, dichlozoline, iprodine, myclozoline, procymidone or vinclozolin; carboxamides such as carboxin, fenfuram, flutolanil, mepronil, oxycarboxin or thifluzamide; guanidines such as guazatine, dodine or iminoctadine; strobilurines such as azoxystrobin, kresoxim-methyl, metominostrobin, SSF-129, methyl 2-[(2-trifluoromethyl)-pyrid-6-yloxymethyl]-3-methoxyacrylate or 2-[α{[(α-methyl-3-trifluoromethyl-benzyl)imino]-oxy}-o-tolyl]-glyoxylic acid-methylester-O-methyloxime (trifloxystrobin); dithiocarbamates such as ferbam, mancozeb, maneb, metiram, propineb, thiram, zineb or ziram; N-halomethylthio-dicarboximides such as captafol, captan, dichlofluanid, fluoromide, folpet or tolyfluanid; copper compounds such as Bordeaux mixture, copper hydroxide, copper oxychloride, copper sulfate, cuprous oxide, mancopper or oxine-copper; nitrophenol derivatives such as dinocap or nitrothal-isopropyl; organo phosphorous derivatives such as edifenphos, iprobenphos, isoprothiolane, phosdiphen, pyrazophos or toclofos-methyl; and other compounds of diverse structures such as acibenzolar-S-methyl, anilazine, blasticidin-S, chinomethionat, chloroneb, chlorothalonil, cymoxanil, dichlone, diclomezine, dicloran, diethofencarb, dimethomorph, dithianon, etridiazole, famoxadone, fenamidone, fentin, ferimzone, fluazinam, flusulfamide, fenhexamid, fosetyl-aluminium, hymexazol, kasugamycin, methasulfocarb, pencycuron, phthalide, polyoxins, probenazole, propamocarb, pyroquilon, quinoxyfen, quintozene, sulfur, triazoxide, tricyclazole, triforine, validamycin, (S)-5-methyl-2-methylthio-5-phenyl-3-phenyl-amino-3,5-dihydroimidazol-4-one (RPA 407213), 3,5-dichloro-N-(3-chloro-1-ethyl-1-methyl-2-oxopropyl)-4-methylbenzamide (RH-7281), N-allyl-4,5-dimethyl-2-trimethylsilylthiophene-3-carboxamide (MON 65500), 4-chloro-4-cyano-N,N-dimethyl-5-p-tolylimidazole-1-sulfonamide (IKF-916), N-(1-cyano-1,2-dimethylpropyl)-2-(2,4-dichlorophenoxy)-propionamide (AC 382042), or iprovalicarb (SZX 722).

Suitable carriers and surfactants may be solid or liquid and correspond to the substances ordinarily employed in formulation technology, such as e.g. natural or regenerated mineral substances, solvents, dispersants, wetting agents, tackifiers, thickeners, binders or fertilisers. Such carriers and additives are described, for example, in WO 95/30651.

A preferred method of applying a compound of formula I, or an agrochemical composition comprising at least one of those compounds, is application to the foliage (foliar application), the frequency and the rate of application depending upon the risk of infestation by the pathogen in question. The compounds of formula I may also be applied to seed grains (coating) either by impregnating the grains with a liquid formulation of the active ingredient or by coating them with a solid formulation.

The compounds of formula I are used in unmodified form or, preferably, together with the adjuvants conventionally employed in formulation technology, and are for that purpose advantageously formulated in known manner e.g. into emulsifiable concentrates, coatable pastes, directly sprayable or dilutable solutions, dilute emulsions, wettable powders, soluble powders, dusts, granules, and by encapsulation in e.g. polymer substances. As with the nature of the compositions, the methods of application, such as spraying, atomising, dusting, scattering, coating or pouring, are chosen in accordance with the intended objectives and the prevailing circumstances.

Advantageous rates of application are normally from 1 g to 2 kg of active ingredient (a.i.) per hectare (ha), preferably from 10 g to 1 kg a.i./ha, especially from 25 g to 750 g a.i./ha. When used as seed dressings, rates of from 0.001 g to 1.0 g of active ingredient per kg of seed are advantageously used.

The formulations, i.e. the compositions, preparations or mixtures comprising the compound(s) (active ingredient(s)) of formula I and, where appropriate, a solid or liquid adjuvant, are prepared in known manner, e.g. by homogeneously mixing and/or grinding the active ingredient with extenders, e.g. solvents, solid carriers and, where appropriate, surface-active compounds (surfactants).

Further surfactants customarily used in formulation technology will be known to the person skilled in the art or can be found in the relevant technical literature.

The agrochemical compositions usually comprise 0.01 to 99% by weight, preferably 0.1 to 95% by weight, of a compound of formula I, 99.99 to 1% by weight, preferably 99.9 to 5% by weight, of a solid or liquid adjuvant, and 0 to 25% by weight, preferably 0.1 to 25% by weight, of a surfactant.

Whereas commercial products will preferably be formulated as concentrates, the end user will normally employ dilute formulations.

The compositions may also comprise further ingredients, such as stabilisers, antifoams, viscosity regulators, binders and tackifiers, as well as fertilisers or other active ingredients for obtaining special effects.

The Examples which follow illustrate the invention described above, without limiting the scope thereof in any way. Temperatures are given in degrees Celsius.

PREPARATION EXAMPLES FOR COMPOUNDS OF FORMULA I

Example 1

2-(3,4-Dichloro-phenyl)-2-methylthioimino-N-[2-(3-methoxy-4-pent-2-ynyloxy-phenyl)-ethyl]-acetamide

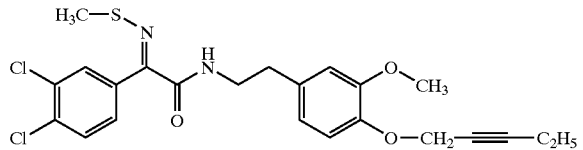

a) N-[2-(4-Hydroxy-3-methoxy-phenyl)-ethyl]-formamide

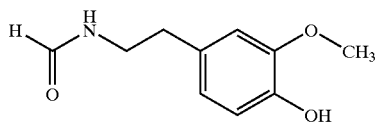

50 g (256 mmol) trans-2-methoxy-4-(2-nitrovinyl)phenol are hydrogenated in 1.5 l EtOH and 63.1 g HCl 37% with 30 g Pd/C (10%) at normal pressure and from −18° C. to +35 20° C. The solution is filtrated on Cellite and recrystallised from EtOH/ether. 41.6 g (80%) product is isolated.

65.6 g (323 mmol) of the same product is dissolved in 1050 ml MeOH and treated with 48 ml (347 mmol) triethylamine and 1650 ml ethyl formiate. The clear solution is refluxed for 22 hours. After evaporation, flash-chromatography of the residue and crystallisation in ether, 42.6 g (68%) N-[2-(4-hydroxy-3-methoxy-phenyl)-ethyl]-formamide is isolated. $^1$H-NMR (300 MHz, CDCl$_3$): 2.79 (m, 2 H, CH$_2$CH$_2$), 3.45 and 3.56 (2 q, (17:83), 2 H, CH$_2$CH$_2$), 3.89 (s, 3 H, OCH$_3$), 5.55–5.68 (m, 2 H, NH, OH), 6.69 and 6.86, 2 m, 3 H, arom.), 8.15 (s, 1 H, CHO).

b) N-[2-(3-Methoxy-4-pent-2-ynyloxy-phenyl)-ethyl]-formamide

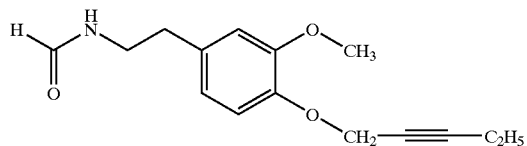

41 ml NaOMe 30% in methanol are added to a solution of 31.5 g (180 mmol) N-[2-(4-hydroxy-3-methoxy-phenyl)-ethyl]-formamide in 880 ml methanol. 48.1 g (184 mmol) toluene-4-sulfonic acid pent-2-ynyl ester are added and the mixture is refluxed for 4 hours. After evaporation the residue is taken up in ethyl acetate and washed with water. After evaporation the residue is submitted to flash-chromatography and crystallisation in ether to give 27.8 g (61%) of the N-[2-(3-methoxy-4-pent-2-ynyloxy-phenyl)-ethyl]-formamide. $^1$H-NMR (300 MHz, CDCl$_3$): 1.14 (t, 3 H, CH$_2$CH$_3$), 2.22 (m, 2 H, CH$_2$CH$_3$), 2.81 (t, 2 H, CH$_2$CH$_2$), 3.48 and 3.57 (2 q (17:83), 2 H, CH$_2$CH$_2$), 3.88 (s, 3 H, OCH$_3$), 4.70 (m, 2 H, OCH$_2$), 5.58 (b, 1 H, NH), 6.73 (m, 2 H, arom.), 6.98 (m, 1 H, arom.), 8.14 (s, 1 H, CHO).

c) 2-(3,4-Dichloro-phenyl)-2-hydroxy-N-[2-(3-methoxy-4-pent-2-ynyloxy-phenyl)-ethyl]-acetamide

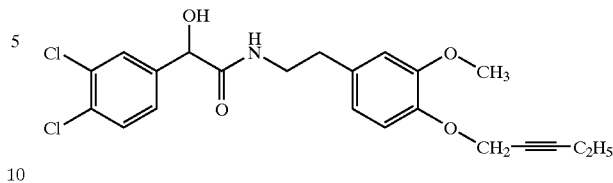

3.4 g (13.0 mmol) N-[2-(3-methoxy-4-pent-2-ynyloxy-phenyl)-ethyl]-formamide and 4.3 ml (32 mmol) triethylamine are dissolved in 13 ml CH$_2$Cl$_2$. 1.4 g (4.7 mmol) bis(trichloromethyl) carbonate (triphosgene) in 9 ml CH$_2$Cl$_2$ is added at +5° C. The mixture is stirred 4 hours at +5° C. and then cooled to −78° C. A solution of 1.43 ml (13.0 mmol) TiCl$_4$ in 20 ml CH$_2$Cl$_2$ is added and the mixture is stirred for 2 hours at −40° C. 2.5 g (12.9 mmol) 3,4-dichloro-benzaldehyde in 7 ml CH$_2$Cl$_2$ is added dropwise and the mixture stirred for 17 hours at +20° C. The mixture is hydrolysed with 7 ml HCl 5N, stirred 30 minutes at +20° C. and washed with water. After evaporation the residue is submitted to flash-chromatography (ethyl acetate 6, hexanes 4) to give 2.7 g (48%) of the 2-(3,4-dichloro-phenyl)-2-hydroxy-N-[2-(3-methoxy-4-pent-2-ynyloxy-phenyl)-ethyl]-acetamide. $^1$H-NMR (300 MHz, CDCl$_3$): 1.15 (t, 3 H, CH$_2$CH$_3$), 2.22 (m, 2 H, CH$_2$CH$_3$), 2.75 (t, 2 H, CH$_2$CH$_2$), 3.51 (m, 2 H, CH$_2$CH$_2$), 3.69 (d, 2 H, OH), 3.83 (s, 3 H, OCH$_3$), 4.74 (m, 2 H, OCH2), 4.96 (d, 1 H, CHOH), 6.27 (t, 1 H, NH), 6.58 (m, 1 H), 6.68 (m, 1 H), 6.92 (d, 1 H), 7.19 (d, 1 H), 7.42 (d, 1 H) and 7.49 (m, 1 H, CH arom.).

d) 2-(3,4-Dichloro-phenyl)-N-[2-(3-methoxy-4-pent-2-ynyloxy-phenyl)-ethyl]-2-oxo-acetamide

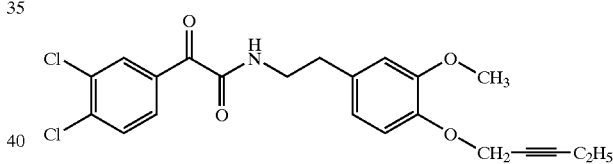

To a solution of 0.8 ml oxalyl chloride (9.0 mmol) in 8 ml methylenchloride at −63° C is added in 15 minutes a solution of 0.84 ml DMSO (12.0 mmol) in 4 ml CH$_2$Cl$_2$. A solution of 2.6 g (6.0 mmol) of 2-(3,4-dichloro-phenyl)-2-hydroxy-N-[2-(3-methoxy-4-pent-2-ynyloxy-phenyl)-ethyl]-acetamide in 30 ml CH$_2$Cl$_2$ is added in 10 minutes. After 10 minutes at −65° C. a solution of 3.2 ml (24.0 mmol) triethylamine in 8 ml CH$_2$Cl$_2$ is added in 15 minutes. After 15 more minutes at that temperature the mixture is hydrolysed with 6.0 ml water and warmed up to +20° C. The solution is washed with solutions of KHSO$_4$ (20%), saturated NaHCO$_3$ and saturated NaCl. After evaporation the residue is submitted to flash-chromatography (ethyl acetate 25, hexanes 75) to give 2.0 g (77%) of the 2-(3,4-dichloro-phenyl)-N-[2-(3-methoxy-4-pent-2-ynyloxy-phenyl)-ethyl]-2-oxo-acetamide. $^1$H-NMR (300 MHz, CDCl$_3$): 1.15 (t, 3 H, CH$_2$CH$_3$), 2.22 (m, 2 H, CH$_2$CH$_3$), 2.87 (t, 2 H, CH$_2$CH$_2$), 3.64 (t, 2 H, CH$_2$CH$_2$), 3.88 (s, 3 H, OCH$_3$), 4.72 (m, 2 H, OCH2), 6.77 (m, 2 H, CH arom.), 6.99 (d, 1 H, CH arom.), 7.16 (t, 1 H, NH), 7.57 (d, 8.22, m) and 8.49 (m, 3 H, CH arom.).

e) To a solution of 1.7 g (3.9 mmol) 2-(3,4-dichloro-phenyl)-N-[2-(3-methoxy-4-pent-2-ynyloxy-phenyl)-ethyl]-2-oxo-acetamide in 32 ml THF, 3.0 g (14.0 mmol) N,N-bis(trimethyl-silyl) methanesulfonamide and 0.1 g (0.32 mmol)

tetrabutylammonium bromide (TBAF) are added. The mixture is heated at +70° C. for 7 hours. After cooling, the mixture is diluted with ethyl acetate and washed twice with water. After evaporation of the organic phase the residue is purified by flash-chromatography (ethyl acetate 25, hexanes 75) to give 1.31 g (70%) of the 2-(3,4-dichloro-phenyl)-2-methylthioimino-N-[2-(3-methoxy-4-pent-2-ynyloxy-phenyl)-ethyl]-acetamide. $^1$H-NMR (300 MHz, CDCl$_3$): 1.15 (t, 3 H, CH$_2$CH$_3$), 2.22 (m, 2 H, CH$_2$CH$_3$), 2.73 (s, 3 H, SCH$_3$), 2.83 (t, 2 H, CH$_2$CH$_2$) 3.59 (t, 2 H, CH$_2$CH$_2$) 3.89 (s, 3 H, OCH$_3$) 4.73 (m, 2 H, OCH2) 6.78 (m, 2 H, CH arom.), 7.02 (m, 1 H, CH arom.), 7.12 (t, 1 H, NH), 7.30 and 7.58 (m, 3 H, CH arom.).

Example 2

2-{2-[1-(4-Chloro-phenyl)-ethylideneaminooxymethyl]-phenyl}-methylthioimino-acetic Acid Methyl Ester

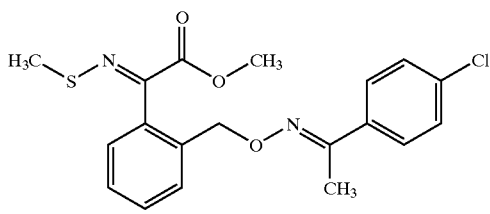

a) 2-{2-[1-(4-Chloro-phenyl)-ethylideneaminooxymethyl]-phenyl}-tosyloxyimino-acetic Acid Methyl Ester

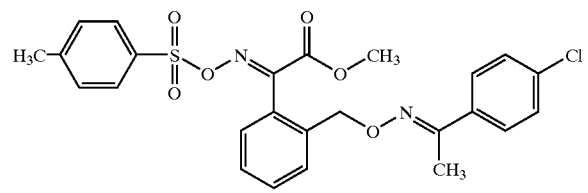

To a suspension of 0.96 g sodium hydride (as a 60% dispersion in mineral oil) in 25 ml dimethylformamide 5.78 g (16 mmol) 2-{2-[1-(4-chloro-phenyl)-ethylideneaminooxymethyl]-phenyl}-hydroxyimino-acetic acid methyl ester followed by 3.6 g (19 mmol) p-toluenesulfonyl chloride are added. The mixture is stirred at room temperature during 3 hours and then hydrolysed with ice-water. After extraction with ethyl acetate the organic phase is washed with water and evaporated. The residue is purified by silicagel chromatography (ethyl acetate 1, hexanes 4) yielding 6.2 g (72%) of the 2-{2-[1-(4-chloro-phenyl)-ethylidene-aminooxymethyl]-phenyl}-tosyloxyimino-acetic acid methyl ester. Melting point 124–126° C.
b) To a solution of 2 ml triethylamine in 15 ml chloroform saturated with methanethiol are added 5.15 g (10 mmol) 2-{2-[1-(4-chloro-phenyl)-ethylideneaminooxymethyl]-phenyl}-tosyloxyimino-acetic acid methyl ester. The mixture was stirred at room temperature for 48 hours. After evaporation the residue is purified by silicagel chromatography (ethyl acetate 1, hexanes 5) to give—after elution of 2-[1-(4-chloro-phenyl)-ethylideneaminooxymethyl]-benzonitrile as by-product—1.0 g (28%) of the 2-{2-[1-(4-chloro-phenyl)-ethylideneamino-oxymethyl]-phenyl}-methylthioimino-acetic acid methyl ester. Melting point of 112–113° C.

Example 3

2-{2-[1-(4-Chloro-phenyl)-ethylideneaminooxymethyl]-phenyl}-2-methylthioimino-N-methyl-acetamide

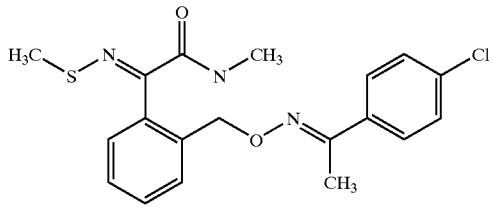

0.5 g (1.28 mmol) 2-{2-[1-(4-Chloro-phenyl)-ethylideneaminooxymethyl]-phenyl}-methylthioimino-acetic acid methyl ester in 5 ml ethanol containing 33% methylamine are stirred 5.15 at room temperature for 2 hours. After evaporation the residue is crystallized from diethylether to give 435 mg (87%) of the 2-{2-[1-(4-Chloro-phenyl)-ethylideneamino-oxymethyl]-phenyl}-2-methylthioimino-N-methyl-acetamide. Melting point of 118–119° C.

Analogously to the above Examples the following compounds of Tables 1 to 41 may be prepared. In the tables Ph means phenyl.

The geometry of the sulfenimine group of the compounds may be E, Z or a mixture of both.

TABLE 01

Compounds of formula Ia

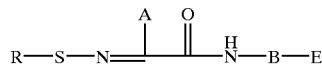

(Ia)

where R is methyl and wherein the combination of A, B and E corresponds to one line in Table A.

Table 02:

Compounds of formula Ia where R is ethyl and wherein the combination of A, B and E corresponds to one line in Table A.

Table 03:

Compounds of formula Ia where R is propyl and wherein the combination of A, B and E corresponds to one line in Table A.

Table 04:

Compounds of formula Ia where R is isopropyl and wherein the combination of A, B and E corresponds to one line in Table A.

Table 05:

Compounds of formula Ia where R is n-butyl and wherein the combination of A, B and E corresponds to one line in Table A.

Table 06:
Compounds of formula Ia where R is tert-butyl and wherein the combination of A, B and E corresponds to one line in Table A.

Table 07:
Compounds of formula Ia where R is 3-chloropropyl and wherein the combination of A, B and E corresponds to one line in Table A.

Table 08:
Compounds of the formula Ia where R is 2-methyl-2-propyl and wherein the combination of A, B and E corresponds to one line in Table A.

Table 09:
Compounds of formula Ia where R is allyl and wherein the combination of A, B and E corresponds to one line in Table A.

Table 10:
Compounds of formula Ia where R is $CF_3$ and wherein the combination of A, B and E corresponds to one line in Table A.

TABLE 11

Compounds of formula Ib

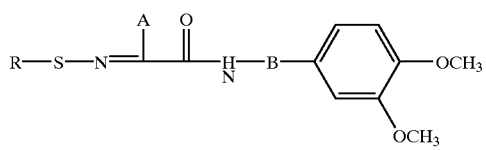

(Ib)

wherein the combination of R, A and B corresponds to one line in Table B.

TABLE 12

Compounds of the formula Ic

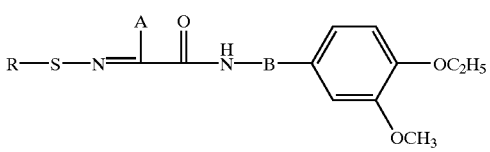

(Ic)

wherein the combination of R, A and B corresponds to one line in Table B.

TABLE 13

Compounds of the formula Id

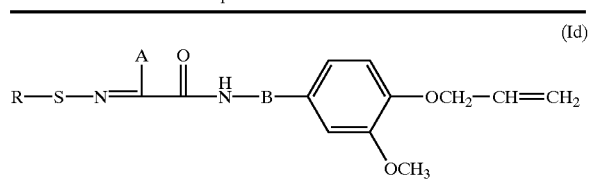

(Id)

wherein the combination of R, A and B corresponds to one line in Table B.

TABLE 14

Compounds of the formula Ie

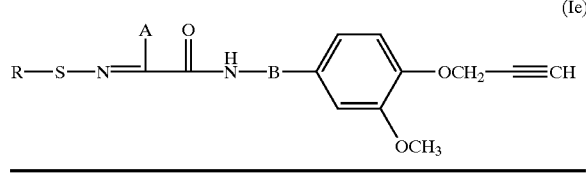

(Ie)

wherein the combination of R, A and B corresponds to one line in Table B.

TABLE 15

Compounds of the formula If

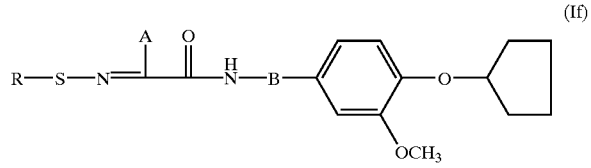

(If)

wherein the combination of R, A and B corresponds to one line in Table B.

TABLE 16

Compounds of the formula Ig

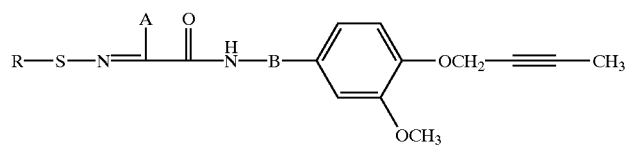

(Ig)

wherein the combination of R, A and B corresponds to one line in Table B.

TABLE 17

Compounds of the formula Ih

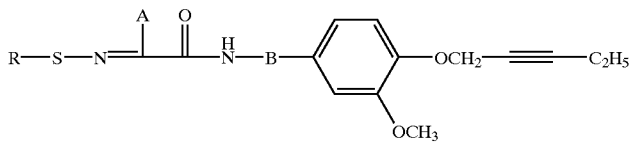
(Ih)

wherein the combination of R, A and B corresponds to one line in Table B.

TABLE 18

Compounds of the formula Ii

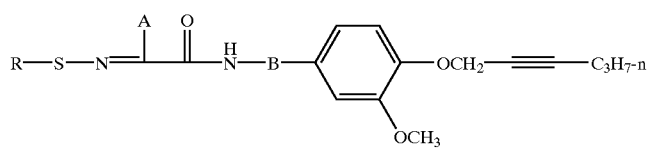
(Ii)

wherein the combination of R, A and B corresponds to one line in Table B.

TABLE 19

Compounds of the formula Ij

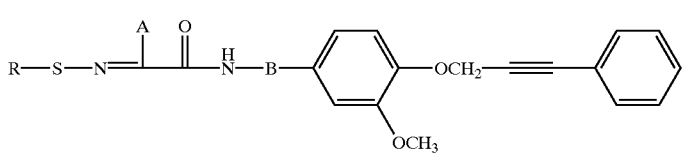
(Ij)

wherein the combination of R, A and B corresponds to one line in Table B.

TABLE 20

Compounds of the formula Ik

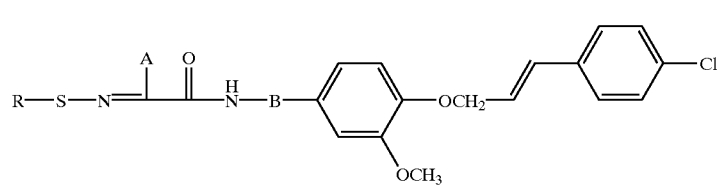
(Ik)

wherein the combination of R, A and B corresponds to one line in Table B.

TABLE 21

Compounds of the formula Il

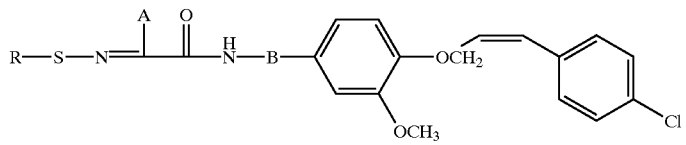
(Il)

wherein the combination of R, A and B corresponds to one line in Table B.

TABLE 22

Compounds of the formula Im

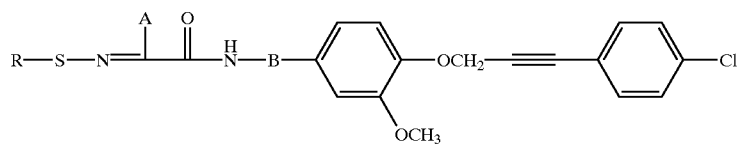
(Im)

wherein the combination of R, A and B corresponds to one line in Table B.

TABLE 23

Compounds of the formula In

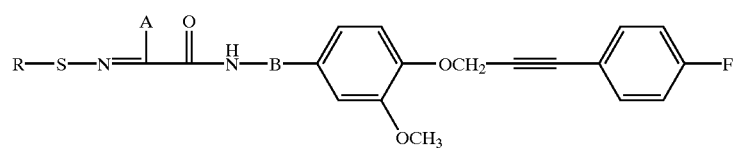
(In)

wherein the combination of R, A and B corresponds to one line in Table B.

TABLE 24

Compounds of the formula Io

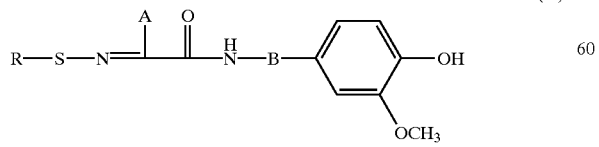
(Io)

wherein the combination of R, A and B corresponds to one line in Table B.

TABLE 25

Compounds of the formula Ip

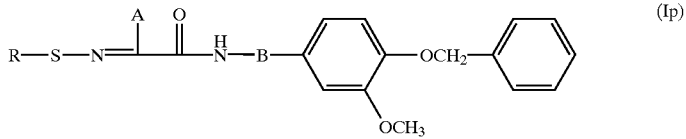

wherein the combination of R, A and B corresponds to one line in Table B.

TABLE 26

Compounds of the formula Iq

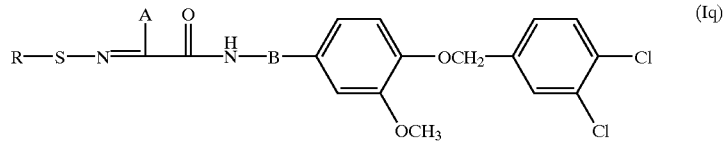

wherein the combination of R, A and B corresponds to one line in Table B.

TABLE 27

Compounds of the formula Ir

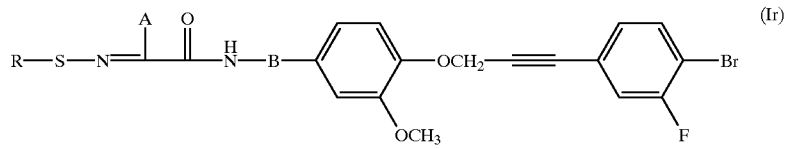

wherein the combination of R, A and B corresponds to one line in Table B.

TABLE 28

Compounds of the formula Is

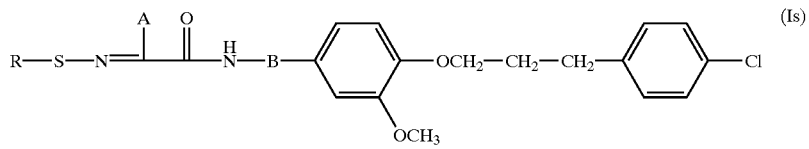

wherein the combination of R, A and B corresponds to one line in Table B.

TABLE 29

Compounds of the formula It $$R-S-N=\overset{A}{\underset{}{C}}-\overset{O}{\underset{}{C}}-\overset{H}{\underset{}{N}}-B-\text{(aryl)}-OCH_2-CH_2-O-\text{(aryl)}-Cl \quad (It)$$

(with OCH$_3$ substituent on first aryl)

wherein the combination of R, A and B corresponds to one line in Table B.

TABLE 30

Compounds of the formula Iu $$H_3C-S-N=\overset{}{\underset{}{C}}-\overset{O}{\underset{}{C}}-\overset{H}{\underset{}{N}}-CH_3 \quad (Iu)$$

(with W-Z substituted phenyl)

wherein the combination of W and Z corresponds to one line in Table C.

TABLE 31

Compounds of the formula Iv $$H_3C-S-N=\overset{}{\underset{}{C}}-\overset{O}{\underset{}{C}}-O-CH_3 \quad (Iv)$$

(with W-Z substituted phenyl)

wherein the combination of W and Z corresponds to one line in Table C.

TABLE 32

Compounds of the formula XIa $$R-S-N=\overset{A}{\underset{}{C}}-\overset{O}{\underset{}{C}}-\overset{H}{\underset{}{N}}-B-E \quad (XIa)$$

where -B-E is O-methyl and wherein the combination of A and R corresponds to one line in Table D.

Table 33:
  Compounds of formula XIa where -B-E is O-ethyl and wherein the combination of A and R corresponds to one line in Table D.

Table 34:
  Compounds of formula XIa where Y is O-n-propyl and wherein the combination of A and R corresponds to one line in Table D.

Table 35:
  Compounds of formula XIa where -B-E is O-iso-propyl and wherein the combination of A and By R corresponds to one line in Table D.

Table 36:
  Compounds of formula XIa where -B-E is O-n-butyl and wherein the combination of A and R corresponds to one line in Table D.

Table 37:
  Compounds of formula XIa where -B-E is O-sec-butyl and wherein the combination of A and R corresponds to one line in Table D.

Table 38:
  Compounds of formula XIa where -B-E is O-tert-butyl and wherein the combination of A and R corresponds to one line in Table D.

Table 39:
  Compounds of formula XIa where -B-E is O-phenyl and wherein the combination of A and R corresponds to one line in Table D.

Table 40:
  Compounds of formula XIa where -B-E is O-benzyl and wherein the combination of A and R corresponds to one line in Table D.

TABLE A

|     | A  | B         | E                                |
|-----|----|-----------|----------------------------------|
| 001 | Ph | CH$_2$    | Ph                               |
| 002 | Ph | CH$_2$    | 4-Cl—Ph                          |
| 003 | Ph | CH$_2$    | 3,4-di—Cl—Ph                     |
| 004 | Ph | CH$_2$    | 2,4-di—Cl—Ph                     |
| 005 | Ph | CH$_2$    | 4-Br—Ph                          |
| 006 | Ph | CH$_2$    | 4-CH$_3$—Ph                      |
| 007 | Ph | CH$_2$    | 4-C$_2$H$_5$—Ph                  |
| 008 | Ph | CH$_2$    | 4-OCH$_3$—Ph                     |
| 009 | Ph | CH$_2$    | 4-CF$_3$—Ph                      |
| 010 | Ph | CH$_2$    | 4-cycl-C$_5$H$_{11}$—Ph          |
| 011 | Ph | CH$_2$    | 3-OCH$_3$-4-OPh—Ph               |
| 012 | Ph | CH$_2$    | 3-OCH$_3$-4-SCH$_3$—Ph           |
| 013 | Ph | CH$_2$    | 4-CH$_3$OOC—Ph                   |
| 014 | Ph | CH$_2$    | 3-NO$_2$—Ph                      |
| 015 | Ph | CH$_2$    | 4-CN—Ph                          |
| 016 | Ph | CH$_2$    | 4-(CH$_3$)$_2$N—Ph               |
| 017 | Ph | CH(CH$_3$) | Ph                              |
| 018 | Ph | CH(CH$_3$) | 4-Cl—Ph                         |
| 019 | Ph | CH(CH$_3$) | 3,4-di—Cl—Ph                    |
| 020 | Ph | CH(CH$_3$) | 2,4-di—Cl—Ph                    |
| 021 | Ph | CH(CH$_3$) | 4-Br—Ph                         |
| 022 | Ph | CH(CH$_3$) | 4-CH$_3$—Ph                     |
| 023 | Ph | CH(CH$_3$) | 4-C$_2$H$_5$—Ph                 |
| 024 | Ph | CH(CH$_3$) | 4-OCH$_3$—Ph                    |
| 025 | Ph | CH(CH$_3$) | 4-CF$_3$—Ph                     |
| 026 | Ph | CH(CH$_3$) | 4-cycl-C$_5$H$_{11}$—Ph         |
| 027 | Ph | CH(CH$_3$) | 3-OCH$_3$-4-OPh—Ph              |
| 028 | Ph | CH(CH$_3$) | 3-OCH$_3$-4-SCH$_3$—Ph          |
| 029 | Ph | CH(CH$_3$) | 4-CH$_3$OOC—Ph                  |
| 030 | Ph | CH(CH$_3$) | 3-NO$_2$—Ph                     |
| 031 | Ph | CH(CH$_3$) | 4-Cl—Ph                         |
| 032 | Ph | CH(CH$_3$) | 4-(CH$_3$)$_2$N—Ph              |
| 033 | Ph | CH$_2$—CH$_2$ | Ph                           |
| 034 | Ph | CH$_2$—CH$_2$ | 4-Cl—Ph                      |
| 035 | Ph | CH$_2$—CH$_2$ | 3,4-di—Cl—Ph                 |
| 036 | Ph | CH$_2$—CH$_2$ | 2,4-di—Cl—Ph                 |

TABLE A-continued

| | A | B | E |
|---|---|---|---|
| 037 | Ph | CH$_2$—CH$_2$ | 4-Br—Ph |
| 038 | Ph | CH$_2$—CH$_2$ | 4-CH$_3$—Ph |
| 039 | Ph | CH$_2$—CH$_2$ | 4-C$_2$H$_5$—Ph |
| 040 | Ph | CH$_2$—CH$_2$ | 4-OCH$_3$—Ph |
| 041 | Ph | CH$_2$—CH$_2$ | 4-CF$_3$—Ph |
| 042 | Ph | CH$_2$—CH$_2$ | 4-cycl-C$_5$H$_{11}$—Ph |
| 043 | Ph | CH$_2$—CH$_2$ | 3-OCH$_3$-4-OPh—Ph |
| 044 | Ph | CH$_2$—CH$_2$ | 3-OCH$_3$-4-SCH$_3$—Ph |
| 045 | Ph | CH$_2$—CH$_2$ | 4-CH$_3$OOC—Ph |
| 046 | Ph | CH$_2$—CH$_2$ | 3-NO$_2$—Ph |
| 047 | Ph | CH$_2$—CH$_2$ | 4-CN—Ph |
| 048 | Ph | CH$_2$—CH$_2$ | 4-(CH$_3$)$_2$N—Ph |
| 049 | Ph | CH(CH$_3$)—CH$_2$ | Ph |
| 050 | Ph | CH(CH$_3$)—CH$_2$ | 4-Cl—Ph |
| 051 | Ph | CH(CH$_3$)—CH$_2$ | 3,4-di-Cl—Ph |
| 052 | Ph | CH(CH$_3$)—CH$_2$ | 2,4-di-Cl—Ph |
| 053 | Ph | CH(CH$_3$)—CH$_2$ | 4-Br—Ph |
| 054 | Ph | CH(CH$_3$)—CH$_2$ | 4-CH$_3$—Ph |
| 055 | Ph | CH(CH$_3$)—CH$_2$ | 4-C$_2$H$_5$—Ph |
| 056 | Ph | CH(CH$_3$)—CH$_2$ | 4-OCH$_3$—Ph |
| 057 | Ph | CH(CH$_3$)—CH$_2$ | 4-CF$_3$—Ph |
| 058 | Ph | CH(CH$_3$)—CH$_2$ | 4 cycl-C$_5$H$_{11}$—Ph |
| 059 | Ph | CH(CH$_3$)—CH$_2$ | 3-OCH$_3$-4-OPh—Ph |
| 060 | Ph | CH(CH$_3$)—CH$_2$ | 3-OCH$_3$-4-SCH$_3$—Ph |
| 061 | Ph | CH(CH$_3$)—CH$_2$ | 4-CH$_3$OOC—Ph |
| 062 | Ph | CH(CH$_3$)—CH$_2$ | 3-NO$_2$—Ph |
| 063 | Ph | CH(CH$_3$)—CH$_2$ | 4-CN—Ph |
| 064 | Ph | CH(CH$_3$)—CH$_2$ | 4-(CH$_3$)$_2$N—Ph |
| 065 | 4-Cl—Ph | CH$_2$ | Ph |
| 066 | 4-Cl—Ph | CH$_2$ | 4-Cl—Ph |
| 067 | 4-Cl—Ph | CH$_2$ | 3,4-di—Cl—Ph |
| 068 | 4-Cl—Ph | CH$_2$ | 2,4-di—Cl—Ph |
| 069 | 4-Cl—Ph | CH$_2$ | 4-Br—Ph |
| 070 | 4-Cl—Ph | CH$_2$ | 4-CH$_3$—Ph |
| 071 | 4-Cl—Ph | CH$_2$ | 4-C$_2$H$_5$—Ph |
| 072 | 4-Cl—Ph | CH$_2$ | 4-OCH$_3$—Ph |
| 073 | 4-Cl—Ph | CH$_2$ | 4-CF$_3$—Ph |
| 074 | 4-Cl—Ph | CH$_2$ | 4-cycl-C$_5$H$_{11}$—Ph |
| 075 | 4-Cl—Ph | CH$_2$ | 3-OCH$_3$-4-OPh—Ph |
| 076 | 4-Cl—Ph | CH$_2$ | 3-OCH$_3$-4-SCH$_3$—Ph |
| 077 | 4-Cl—Ph | CH$_2$ | 4-CH$_3$OOC—Ph |
| 078 | 4-Cl—Ph | CH$_2$ | 3-NO$_2$—Ph |
| 079 | 4-Cl—Ph | CH$_2$ | 4-CN—Ph |
| 080 | 4-Cl—Ph | CH$_2$ | 4-(CH$_3$)$_2$N—Ph |
| 081 | 4-Cl—Ph | CH(CH$_3$) | Ph |
| 082 | 4-Cl—Ph | CH(CH$_3$) | 4-Cl—Ph |
| 083 | 4-Cl—Ph | CH(CH$_3$) | 3,4-di—Cl—Ph |
| 084 | 4-Cl—Ph | CH(CH$_3$) | 2,4-di—Cl—Ph |
| 085 | 4-Cl—Ph | CH(CH$_3$) | 4-Br—Ph |
| 086 | 4-Cl—Ph | CH(CH$_3$) | 4-CH$_3$—Ph |
| 087 | 4-Cl—Ph | CH(CH$_3$) | 4-C$_2$H$_5$—Ph |
| 088 | 4-Cl—Ph | CH(CH$_3$) | 4-OCH$_3$—Ph |
| 089 | 4-Cl—Ph | CH(CH$_3$) | 4-CF$_3$—Ph |
| 090 | 4-Cl—Ph | CH(CH$_3$) | 4-cycl-C$_5$H$_{11}$—Ph |
| 091 | 4-Cl—Ph | CH(CH$_3$) | 3-OCH$_3$-4-OPh—Ph |
| 092 | 4-Cl—Ph | CH(CH$_3$) | 3-OCH$_3$-4-SCH$_3$—Ph |
| 093 | 4-Cl—Ph | CH(CH$_3$) | 4-CH$_3$OOC—Ph |
| 094 | 4-Cl—Ph | CH(CH$_3$) | 3-NO$_2$—Ph |
| 095 | 4-Cl—Ph | CH(CH$_3$) | 4-CN—Ph |
| 096 | 4-Cl—Ph | CH(CH$_3$) | 4-(CH$_3$)$_2$N—Ph |
| 097 | 4-Cl—Ph | CH$_2$—CH$_2$ | Ph |
| 098 | 4-Cl—Ph | CH$_2$—CH$_2$ | 4-Cl—Ph |
| 099 | 4-Cl—Ph | CH$_2$—CH$_2$ | 3,4-di—Cl—Ph |
| 100 | 4-Cl—Ph | CH$_2$—CH$_2$ | 2,4-di—Cl—Ph |
| 101 | 4-Cl—Ph | CH$_2$—CH$_2$ | 4-Br—Ph |
| 102 | 4-Cl—Ph | CH$_2$—CH$_2$ | 4-CH$_3$—Ph |
| 103 | 4-Cl—Ph | CH$_2$—CH$_2$ | 4-C$_2$H$_5$—Ph |
| 104 | 4-Cl—Ph | CH$_2$—CH$_2$ | 4-OCH$_3$—Ph |
| 105 | 4-Cl—Ph | CH$_2$—CH$_2$ | 4-CF$_3$—Ph |
| 106 | 4-Cl—Ph | CH$_2$—CH$_2$ | 4-cycl-C$_5$H$_{11}$—Ph |
| 107 | 4-Cl—Ph | CH$_2$—CH$_2$ | 3-OCH$_3$-4-OPh—Ph |
| 108 | 4-Cl—Ph | CH$_2$—CH$_2$ | 3-OCH$_3$-4-SCH$_3$—Ph |
| 109 | 4-Cl—Ph | CH$_2$—CH$_2$ | 4-CH$_3$OOC—Ph |
| 110 | 4-Cl—Ph | CH$_2$—CH$_2$ | 3-NO$_2$—Ph |
| 111 | 4-Cl—Ph | CH$_2$—CH$_2$ | 4-CN—Ph |
| 112 | 4-Cl—Ph | CH$_2$—CH$_2$ | 4-(CH$_3$)$_2$N—Ph |
| 113 | 4-Cl—Ph | CH(CH$_3$)—CH$_2$ | Ph |
| 114 | 4-Cl—Ph | CH(CH$_3$)—CH$_2$ | 4-Cl—Ph |
| 115 | 4-Cl—Ph | CH(CH$_3$)—CH$_2$ | 3,4-di—Cl—Ph |
| 116 | 4-Cl—Ph | CH(CH$_3$)—CH$_2$ | 2,4-di—Cl—Ph |
| 117 | 4-Cl—Ph | CH(CH$_3$)—CH$_2$ | 4-Br—Ph |
| 118 | 4-Cl—Ph | CH(CH$_3$)—CH$_2$ | 4-CH$_3$—Ph |
| 119 | 4-Cl—Ph | CH(CH$_3$)—CH$_2$ | 4-C$_2$H$_5$—Ph |
| 120 | 4-Cl—Ph | CH(CH$_3$)—CH$_2$ | 4-OCH$_3$—Ph |
| 121 | 4-Cl—Ph | CH(CH$_3$)—CH$_2$ | 4-CF$_3$—Ph |
| 122 | 4-Cl—Ph | CH(CH$_3$)—CH$_2$ | 4-cycl-C$_5$H$_{11}$—Ph |
| 123 | 4-Cl—Ph | CH(CH$_3$)—CH$_2$ | 3-OCH$_3$-4-OPh—Ph |
| 124 | 4-Cl—Ph | CH(CH$_3$)—CH$_2$ | 3-OCH$_3$-4-SCH$_3$—Ph |
| 125 | 4-Cl—Ph | CH(CH$_3$)—CH$_2$ | 4-CH$_3$OOC—Ph |
| 126 | 4-Cl—Ph | CH(CH$_3$)—CH$_2$ | 3-NO$_2$—Ph |
| 127 | 4-Cl—Ph | CH(CH$_3$)—CH$_2$ | 4-CN—Ph |
| 128 | 4-Cl—Ph | CH(CH$_3$)—CH$_2$ | 4-(CH$_3$)$_2$N—Ph |
| 129 | 3,4-di—Cl—Ph | CH$_2$ | Ph |
| 130 | 3,4-di—Cl—Ph | CH$_2$ | 4-Cl—Ph |
| 131 | 3,4-di—Cl—Ph | CH$_2$ | 3,4-di—Cl—Ph |
| 132 | 3,4-di—Cl—Ph | CH$_2$ | 2,4-di—Cl—Ph |
| 133 | 3,4-di—Cl—Ph | CH$_2$ | 4-Br—Ph |
| 134 | 3,4-di—Cl—Ph | CH$_2$ | 4-CH$_3$—Ph |
| 135 | 3,4-di—Cl—Ph | CH$_2$ | 4-C$_2$H$_5$—Ph |
| 136 | 3,4-di—Cl—Ph | CH$_2$ | 4-OCH$_3$—Ph |
| 137 | 3,4-di—Cl—Ph | CH$_2$ | 4-CF$_3$—Ph |
| 138 | 3,4-di—Cl—Ph | CH$_2$ | 4-cycl-C$_5$H$_{11}$—Ph |
| 139 | 3,4-di—Cl—Ph | CH$_2$ | 3-OCH$_3$-4-OPh—Ph |
| 140 | 3,4-di—Cl—Ph | CH$_2$ | 3-OCH$_3$-4-SCH$_3$—Ph |
| 141 | 3,4-di—Cl—Ph | CH$_2$ | 4-CH$_3$OOC—Ph |
| 142 | 3,4-di—Cl—Ph | CH$_2$ | 3-NO$_2$—Ph |
| 143 | 3,4-di—Cl—Ph | CH$_2$ | 4-CN—Ph |
| 144 | 3,4-di—Cl—Ph | CH$_2$ | 4-(CH$_3$)$_2$N—Ph |
| 145 | 3,4-di—Cl—Ph | CH(CH$_3$) | Ph |
| 146 | 3,4-di—Cl—Ph | CH(CH$_3$) | 4-Cl—Ph |
| 147 | 3,4-di—Cl—Ph | CH(CH$_3$) | 3,4-di—Cl—Ph |
| 148 | 3,4-di—Cl—Ph | CH(CH$_3$) | 2,4-di—Cl—Ph |
| 149 | 3,4-di—Cl—Ph | CH(CH$_3$) | 4-Br—Ph |
| 150 | 3,4 di—Cl—Ph | CH(CH$_3$) | 4-CH$_3$—Ph |
| 151 | 3,4-di—Cl—Ph | CH(CH$_3$) | 4-C$_2$H$_5$—Ph |
| 152 | 3,4-di—Cl—Ph | CH(CH$_3$) | 4-OCH$_3$—Ph |
| 153 | 3,4-di—Cl—Ph | CH(CH$_3$) | 4-CF$_3$—Ph |
| 154 | 3,4-di—Cl—Ph | CH(CH$_3$) | 4-cycl-C$_5$H$_{11}$—Ph |
| 155 | 3,4-di—Cl—Ph | CH(CH$_3$) | 3-OCH$_3$-4-OPh—Ph |
| 156 | 3,4-di—Cl—Ph | CH(CH$_3$) | 3-OCH$_3$-4-SCH$_3$—Ph |
| 157 | 3,4-di—Cl—Ph | CH(CH$_3$) | 4-CH$_3$OOC—Ph |
| 158 | 3,4-di—Cl—Ph | CH(CH$_3$) | 3-NO$_2$—Ph |
| 159 | 3,4-di—Cl—Ph | CH(CH$_3$) | 4-CN—Ph |
| 160 | 3,4-di—Cl—Ph | CH(CH$_3$) | 4-(CH$_3$)$_2$N—Ph |
| 161 | 3,4-di—Cl—Ph | CH$_2$—CH$_2$ | Ph |
| 162 | 3,4-di—Cl—Ph | CH$_2$—CH$_2$ | 4-Cl—Ph |
| 163 | 3,4-di—Cl—Ph | CH$_2$—CH$_2$ | 3,4-di—Cl—Ph |
| 164 | 3,4-di—Cl—Ph | CH$_2$—CH$_2$ | 2,4-di—Cl—Ph |
| 165 | 3,4-di—Cl—Ph | CH$_2$—CH$_2$ | 4-Br—Ph |
| 166 | 3,4-di—Cl—Ph | CH$_2$—CH$_2$ | 4-CH$_3$—Ph |
| 167 | 3,4-di—Cl—Ph | CH$_2$—CH$_2$ | 4-C$_2$H$_5$—Ph |
| 168 | 3,4-di—Cl—Ph | CH$_2$—CH$_2$ | 4-OCH$_3$—Ph |
| 169 | 3,4-di—Cl—Ph | CH$_2$—CH$_2$ | 4-CF$_3$—Ph |
| 170 | 3,4-di—Cl—Ph | CH$_2$—CH$_2$ | 4-cycl-C$_5$H$_{11}$—Ph |
| 171 | 3,4-di—Cl—Ph | CH$_2$—CH$_2$ | 3-OCH$_3$-4-OPh—Ph |
| 172 | 3,4-di—Cl—Ph | CH$_2$—CH$_2$ | 3-OCH$_3$-4-SCH$_3$—Ph |
| 173 | 3,4-di—Cl—Ph | CH$_2$—CH$_2$ | 4-CH$_3$OOC—Ph |
| 174 | 3,4-di—Cl—Ph | CH$_2$—CH$_2$ | 3-NO$_2$—Ph |
| 175 | 3,4-di—Cl—Ph | CH$_2$—CH$_2$ | 4-CN—Ph |
| 176 | 3,4-di—Cl—Ph | CH$_2$—CH$_2$ | 4-(CH$_3$)$_2$N—Ph |
| 177 | 3,4-di—Cl—Ph | CH(CH$_3$)—CH$_2$ | Ph |
| 178 | 3,4-di—Cl—Ph | CH(CH$_3$)—CH$_2$ | 4-Cl—Ph |
| 179 | 3,4-di—Cl—Ph | CH(CH$_3$)—CH$_2$ | 3,4-di—Cl—Ph |
| 180 | 3,4-di—Cl—Ph | CH(CH$_3$)—CH$_2$ | 2,4-di—Cl—Ph |
| 181 | 3,4-di—Cl—Ph | CH(CH$_3$)—CH$_2$ | 4-Br—Ph |
| 182 | 3,4-di—Cl—Ph | CH(CH$_3$)—CH$_2$ | 4-CH$_3$—Ph |
| 183 | 3,4-di—Cl—Ph | CH(CH$_3$)—CH$_2$ | 4-C$_2$H$_5$—Ph |
| 184 | 3,4-di—Cl—Ph | CH(CH$_3$)—CH$_2$ | 4-OCH$_3$—Ph |
| 185 | 3,4-di—Cl—Ph | CH(CH$_3$)—CH$_2$ | 4-CF$_3$—Ph |
| 186 | 3,4-di—Cl—Ph | CH(CH$_3$)—CH$_2$ | 4-cycl-C$_5$H$_{11}$—Ph |
| 187 | 3,4-di—Cl—Ph | CH(CH$_3$)—CH$_2$ | 3-OCH$_3$-4-OPh—Ph |
| 188 | 3,4-di—Cl—Ph | CH(CH$_3$)—CH$_2$ | 3-OCH$_3$-4-SCH$_3$—Ph |
| 189 | 3,4-di—Cl—Ph | CH(CH$_3$)—CH$_2$ | 4-CH$_3$OOC—Ph |
| 190 | 3,4-di—Cl—Ph | CH(CH$_3$)—CH$_2$ | 3-NO$_2$—Ph |

TABLE A-continued

| | A | B | E |
|---|---|---|---|
| 191 | 3,4-di—Cl—Ph | CH(CH$_3$)—CH$_2$ | 4-CN—Ph |
| 192 | 3,4-di—Cl—Ph | CH(CH$_3$)—CH$_2$ | 4-(CH$_3$)$_2$N—Ph |
| 193 | 4-Br—Ph | CH$_2$—CH$_2$ | Ph |
| 194 | 4-Br—Ph | CH$_2$—CH$_2$ | 4-Cl—Ph |
| 195 | 4-Br—Ph | CH$_2$—CH$_2$ | 4-CH$_3$—Ph |
| 196 | 4-Br—Ph | CH$_2$—CH$_2$ | 4-C$_2$H$_5$—Ph |
| 197 | 4-Br—Ph | CH$_2$—CH$_2$ | 4-OCH$_3$—Ph |
| 198 | 4-Br—Ph | CH$_2$—CH$_2$ | 3-OCH$_3$-4-OPh—Ph |
| 199 | 4-Br—Ph | CH$_2$—CH$_2$ | 3-OCH$_3$-4-SCH$_3$—Ph |
| 200 | 4-Br—Ph | CH(CH$_3$)—CH$_2$ | Ph |
| 201 | 4-Br—Ph | CH(CH$_3$)—CH$_2$ | 4-Cl—Ph |
| 202 | 4-Br—Ph | CH(CH$_3$)—CH$_2$ | 4-CH$_3$—Ph |
| 203 | 4-Br—Ph | CH(CH$_3$)—CH$_2$ | 4-C$_2$H$_5$—Ph |
| 204 | 4-Br—Ph | CH(CH$_3$)—CH$_2$ | 4-OCH$_3$—Ph |
| 205 | 4-Br—Ph | CH(CH$_3$)—CH$_2$ | 3-OCH$_3$-4-OPh—Ph |
| 206 | 4-Br—Ph | CH(CH$_3$)—CH$_2$ | 3-OCH$_3$-4-SCH$_3$—Ph |
| 207 | 4-OCH$_3$—Ph | CH$_2$—CH$_2$ | Ph |
| 208 | 4-OCH$_3$—Ph | CH$_2$—CH$_2$ | 4-Cl—Ph |
| 209 | 4-OCH$_3$—Ph | CH$_2$—CH$_2$ | 4-CH$_3$—Ph |
| 210 | 4-OCH$_3$—Ph | CH$_2$—CH$_2$ | 4-C$_2$H$_5$—Ph |
| 211 | 4-OCH$_3$—Ph | CH$_2$—CH$_2$ | 4-OCH 3—Ph |
| 212 | 4-OCH$_3$—Ph | CH$_2$—CH$_2$ | 3-OCH$_3$-4-OPh—Ph |
| 213 | 4-OCH$_3$—Ph | CH$_2$—CH$_2$ | 3-OCH$_3$-4-SCH$_3$—Ph |
| 214 | 4-OCH$_3$—Ph | CH(CH$_3$)—CH$_2$ | Ph |
| 215 | 4-OCH$_3$—Ph | CH(CH$_3$)—CH$_2$ | 4-Cl—Ph |
| 216 | 4-OCH$_3$—Ph | CH(CH$_3$)—CH$_2$ | 4-CH$_3$—Ph |
| 217 | 4-OCH$_3$—Ph | CH(CH$_3$)—CH$_2$ | 4-C$_2$H$_5$—Ph |
| 218 | 4-OCH$_3$—Ph | CH(CH$_3$)—CH$_2$ | 4-OCH$_3$—Ph |
| 219 | 4-OCH$_3$—Ph | CH(CH$_3$)—CH$_2$ | 3-OCH$_3$-4-OPh—Ph |
| 220 | 4-OCH$_3$—Ph | CH(CH$_3$)—CH$_2$ | 3-OCH$_3$4-SCH$_3$—Ph |
| 221 | 4-CH$_3$—Ph | CH$_2$—CH$_2$ | Ph |
| 222 | 4-CH$_3$—Ph | CH$_2$—CH$_2$ | 4-Cl-Ph |
| 223 | 4-CH$_3$—Ph | CH$_2$—CH$_2$ | 4 CH$_3$—Ph |
| 224 | 4-CH$_3$—Ph | CH$_2$—CH$_2$ | 4-C$_2$H$_5$—Ph |
| 225 | 4-CH$_3$—Ph | CH$_2$—CH$_2$ | 4-OCH$_3$—Ph |
| 226 | 4-CH$_3$—Ph | CH$_2$—CH$_2$ | 3-OCH$_3$-4-OPh—Ph |
| 227 | 4-CH$_3$—Ph | CH$_2$—CH$_2$ | 3-OCH$_3$-4-SCH$_3$—Ph |
| 228 | 4-CH$_3$—Ph | CH(CH$_3$)—CH$_2$ | Ph |
| 229 | 4-CH$_3$—Ph | CH(CH$_3$)—CH$_2$ | 4-Cl—Ph |
| 230 | 4-CH$_3$—Ph | CH(CH$_3$)—CH$_2$ | 4-CH$_3$—Ph |
| 231 | 4-CH$_3$—Ph | CH(CH$_3$)—CH$_2$ | 4-C$_2$H$_5$—Ph |
| 232 | 4-CH$_3$—Ph | CH(CH$_3$)—CH$_2$ | 4-OCH$_3$—Ph |
| 233 | 4-CH$_3$—Ph | CH(CH$_3$)—CH$_2$ | 3-OCH$_3$-4-OPh—Ph |
| 234 | 4-CH$_3$—Ph | CH(CH$_3$)—CH$_2$ | 3-OCH$_3$-4-SCH$_3$—Ph |
| 235 | 4-F—Ph | CH$_2$—CH$_2$ | 4-Cl—Ph |
| 236 | 4-F—Ph | CH$_2$—CH$_2$ | 4-CH$_3$—Ph |
| 237 | 4-F—Ph | CH$_2$—CH$_2$ | 4-OCH$_3$—Ph |
| 238 | 4-F—Ph | CH(CH$_3$)—CH$_2$ | 4-Cl—Ph |
| 239 | 4-F—Ph | CH(CH$_3$)—CH$_2$ | 4-CH$_3$—Ph |
| 240 | 4-F—Ph | CH(CH$_3$)—CH$_2$ | 4-OCH$_3$—Ph |
| 241 | 3,4-OCH$_2$O—Ph | CH(CH$_3$)—CH$_2$ | 4-Cl—Ph |
| 242 | 3,4-OCH$_2$O—Ph | CH$_2$—Ch$_2$ | 4-CH$_3$—Ph |
| 243 | 3,4-OCH$_2$O—Ph | CH$_2$—CH$_2$ | 4-OCH$_3$—Ph |
| 244 | 3,4-OCH$_2$O—Ph | CH(CH$_3$)—CH$_2$ | 4-Cl—Ph |
| 245 | 3,4-OCH$_2$O—Ph | CH(CH$_3$)—CH$_2$ | 4-CH$_3$—Ph |
| 246 | 3,4-OCH$_2$O Ph | CH(CH$_3$)—CH$_2$ | 4-OCH$_3$—Ph |
| 247 | 3,4-di-OCH$_3$—Ph | CH$_2$—CH$_2$ | 4-Cl—Ph |
| 248 | 3,4-di-OCH$_3$—Ph | CH$_2$—CH$_2$ | 4-CH$_3$—Ph |
| 249 | 3,4-di-OCH$_3$—Ph | CH$_2$—CH$_2$ | 4-OCH$_3$—Ph |
| 250 | 3,4-di-OCH$_3$—Ph | CH(CH$_3$)—CH$_2$ | 4-Cl—Ph |
| 251 | 3,4-di-OCH$_3$—Ph | CH(CH$_3$—CH$_2$ | 4-CH$_3$—Ph |
| 252 | 3,4-di-OCH$_3$—Ph | CH(CH$_3$)—CH$_2$ | 4-OCH$_3$—Ph |
| 253 | 3,4-di-CH$_3$—Ph | CH$_2$—CH$_2$ | 4-Cl—Ph |
| 254 | 3,4-di-CH$_3$—Ph | CH$_2$—CH$_2$ | 4-CH$_3$—Ph |
| 255 | 3,4-di-CH$_3$—Ph | CH$_2$—CH$_2$ | 4-OCH$_3$—Ph |
| 256 | 3,4-di-CH$_3$—Ph | CH(CH$_3$)—CH$_2$ | 4-Cl—Ph |
| 257 | 3,4-di-CH$_3$—Ph | CH(CH$_3$)—CH$_2$ | 4-CH$_3$—Ph |
| 258 | 3,4-di-CH$_3$—Ph | CH(CH$_3$)—CH$_2$ | 4-OCH$_3$—Ph |
| 259 | 3,4-di-Cl—Ph | CH$_2$CH$_2$CH$_2$ | 3,4-di-OCH$_3$—Ph |
| 260 | 3,4-di-Cl—Ph | CH$_2$—CH$_2$ | 3-OCH$_3$-4-OC$_{12}$H$_{25}$—Ph |

TABLE B

| | R | A | B |
|---|---|---|---|
| 001 | CH$_3$ | 4-Cl—Ph | CH$_2$CH$_2$ |
| 002 | C$_2$H$_5$ | 4-Cl—Ph | CH$_2$CH$_2$ |
| 003 | C$_3$H$_7$-n | 4-Cl—Ph | CH$_2$CH$_2$ |
| 004 | C$_3$H$_7$-i | 4-Cl—Ph | CH$_2$CH$_2$ |
| 005 | C$_4$H$_9$-n | 4-Cl—Ph | CH$_2$CH$_2$ |
| 006 | CH$_3$ | 4-Cl—Ph | CH(CH$_3$)CH$_2$ |
| 007 | C$_2$H$_5$ | 4-Cl—Ph | CH(CH$_3$)CH$_2$ |
| 008 | C$_3$H$_7$-n | 4-Cl—Ph | CH(CH$_3$)CH$_2$ |
| 009 | C$_3$H$_7$-i | 4-Cl—Ph | CH(CH$_3$)CH$_2$ |
| 010 | C$_4$H$_9$-n | 4-Cl—Ph | CH(CH$_3$)CH$_2$ |
| 011 | CH$_3$ | 3,4-di-Cl—Ph | CH$_2$CH$_2$ |
| 012 | C$_2$H$_5$ | 3,4-di-Cl—Ph | CH$_2$CH$_2$ |
| 013 | C$_3$H$_7$-n | 3,4-di-Cl—Ph | CH$_2$CH$_2$ |
| 014 | C$_3$H$_7$-i | 3,4-di-Cl—Ph | CH$_2$CH$_2$ |
| 015 | C$_4$H$_9$-n | 3,4-di-Cl—Ph | CH$_2$CH$_2$ |
| 016 | CH$_3$ | 3,4-di-Cl—Ph | CH(CH$_3$)CH$_2$ |
| 017 | C$_2$H$_5$ | 3,4-di-Cl—Ph | CH(CH$_3$)CH$_2$ |
| 018 | C$_3$H$_7$-n | 3,4-di-Cl—Ph | CH(CH$_3$)CH$_2$ |
| 019 | C$_3$H$_7$-i | 3,4-di-Cl—Ph | CH(CH$_3$)CH$_2$ |
| 020 | C$_4$H$_9$-n | 3,4-di-Cl—Ph | CH(CH$_3$)CH$_2$ |
| 021 | CH$_3$ | Ph | CH$_2$CH$_2$ |
| 022 | C$_2$H$_5$ | Ph | CH$_2$CH$_2$ |
| 023 | C$_3$H$_7$-n | Ph | CH$_2$CH$_2$ |
| 024 | C$_3$H$_7$-i | Ph | CH$_2$CH$_2$ |
| 025 | C$_4$H$_9$-n | Ph | CH$_2$CH$_2$ |
| 026 | CH$_3$ | Ph | CH(CH$_3$)CH$_2$ |
| 027 | C$_2$H$_5$ | Ph | CH(CH$_3$)CH$_2$ |
| 028 | C$_3$H$_7$-n | Ph | CH(CH$_3$)CH$_2$ |
| 029 | C$_3$H$_7$-i | Ph | CH(CH$_3$)CH$_2$ |
| 030 | C$_4$H$_9$-n | Ph | CH(CH$_3$)CH$_2$ |
| 031 | CH$_3$ | 4-Br—Ph | CH$_2$CH$_2$ |
| 032 | C$_2$H$_5$ | 4-Br—Ph | CH$_2$CH$_2$ |
| 033 | C$_3$H$_7$-n | 4-Br—Ph | CH$_2$CH$_2$ |
| 034 | C$_3$H$_7$-i | 4-Br—Ph | CH$_2$CH$_2$ |
| 035 | C$_4$H$_9$-n | 4-Br—Ph | CH$_2$CH$_2$ |
| 036 | CH$_3$ | 4-Br—Ph | CH(CH$_3$)CH$_2$ |
| 037 | C$_2$H$_5$ | 4-Br—Ph | CH(CH$_3$)CH$_2$ |
| 038 | C$_3$H$_7$-n | 4-Br—Ph | CH(CH$_3$)CH$_2$ |
| 039 | C$_3$H$_7$-i | 4-Br—Ph | CH(CH$_3$)CH$_2$ |
| 040 | C$_4$H$_9$-n | 4-Br—Ph | CH(CH$_3$)CH$_2$ |
| 041 | CH$_3$ | 4-CH$_3$—Ph | CH$_2$CH$_2$ |
| 042 | C$_2$H$_5$ | 4-CH$_3$—Ph | CH$_2$CH$_2$ |
| 043 | C$_3$H$_7$-n | 4-CH$_3$—Ph | CH$_2$CH$_2$ |
| 044 | C$_3$H$_7$-i | 4-CH$_3$—Ph | CH$_2$CH$_2$ |
| 045 | C$_4$H$_9$-n | 4-CH$_3$—Ph | CH$_2$CH$_2$ |
| 046 | CH$_3$ | 4-CH$_3$—Ph | CH(CH$_3$)CH$_2$ |
| 047 | C$_2$H$_5$ | 4-CH$_3$—Ph | CH(CH$_3$)CH$_2$ |
| 048 | C$_3$H$_7$-n | 4-CH$_3$—Ph | CH(CH$_3$)CH$_2$ |
| 049 | C$_3$H$_7$-i | 4-CH$_3$—Ph | CH(CH$_3$)CH$_2$ |
| 050 | C$_4$H$_9$-n | 4-CH$_3$—Ph | CH(CH$_3$)CH$_2$ |
| 051 | CH$_3$ | 4-CH$_3$O—Ph | CH$_2$CH$_2$ |
| 052 | C$_2$H$_5$ | 4-CH$_3$O—Ph | CH$_2$CH$_2$ |
| 053 | C$_3$H$_7$-n | 4-CH$_3$O—Ph | CH$_2$CH$_2$ |
| 054 | C$_3$H$_7$-i | 4-CH$_3$O—Ph | CH$_2$CH$_2$ |
| 055 | C$_4$H$_9$-n | 4-CH$_3$O—Ph | CH$_2$CH$_2$ |
| 056 | CH$_3$ | 4-CH$_3$O—Ph | CH(CH$_3$)CH$_2$ |
| 057 | C$_2$H$_5$ | 4-CH$_3$O—Ph | CH(CH$_3$)CH$_2$ |
| 058 | C$_3$H$_7$-n | 4-CH$_3$O—Ph | CH(CH$_3$)CH$_2$ |
| 059 | C$_3$H$_7$-i | 4-CH$_3$O—Ph | CH(CH$_3$)CH$_2$ |
| 060 | C$_4$H$_9$-n | 4-CH$_3$O—Ph | CH(CH$_3$)CH$_2$ |
| 061 | CH$_3$ | 4-CF$_3$—Ph | CH$_2$CH$_2$ |
| 062 | C$_2$H$_5$ | 4-CF$_3$—Ph | CH$_2$CH$_2$ |
| 063 | C$_3$H$_7$-n | 4-CF$_3$—Ph | CH$_2$CH$_2$ |
| 064 | C$_3$H$_7$-i | 4-CF$_3$—Ph | CH$_2$CH$_2$ |
| 065 | C$_4$H$_9$-n | 4-CF$_3$—Ph | CH$_2$CH$_2$ |
| 066 | CH$_3$ | 4-CF$_3$—Ph | CH(CH$_3$)CH$_2$ |
| 067 | C$_2$H$_5$ | 4-CF$_3$—Ph | CH(CH$_3$)CH$_2$ |
| 068 | C$_3$H$_7$-n | 4-CF$_3$—Ph | CH(CH$_3$)CH$_2$ |
| 069 | C$_3$H$_7$-i | 4-CF$_3$—Ph | CH(CH$_3$)CH$_2$ |
| 070 | C$_4$H$_9$-n | 4-CF$_3$—Ph | CH(CH$_3$)CH$_2$ |
| 071 | CH$_3$ | 4-F—Ph | CH$_2$CH$_2$ |
| 072 | C$_2$H$_5$ | 4-F—Ph | CH$_2$CH$_2$ |
| 073 | C$_3$H$_7$-n | 4-F—Ph | CH$_2$CH$_2$ |
| 074 | C$_3$H$_7$-i | 4-F—Ph | CH$_2$CH$_2$ |
| 075 | C$_4$H$_9$-n | 4-F—Ph | CH$_2$CH$_2$ |
| 076 | CH$_3$ | 4-F—Ph | CH(CH$_3$)CH$_2$ |
| 077 | C$_2$H$_5$ | 4-F—Ph | CH(CH$_3$)CH$_2$ |

TABLE B-continued

| | R | A | B |
|---|---|---|---|
| 078 | C$_3$H$_7$-n | 4-F—Ph | CH(CH$_3$)CH$_2$ |
| 079 | C$_3$H$_7$-i | 4-F—Ph | CH(CH$_3$)CH$_2$ |
| 080 | C$_4$H$_9$-n | 4-F—Ph | CH(CH$_3$)CH$_2$ |
| 081 | CH$_3$ | 4-CF$_3$O—Ph | CH$_2$CH$_2$ |
| 082 | C$_2$H$_5$ | 4-CF$_3$O—Ph | CH$_2$CH$_2$ |
| 083 | C$_3$H$_7$-n | 4-CF$_3$O—Ph | CH$_2$CH$_2$ |
| 084 | C$_3$H$_7$-i | 4-CF$_3$O—Ph | CH$_2$CH$_2$ |
| 085 | C$_4$H$_9$-n | 4-CF$_3$O—Ph | CH$_2$CH$_2$ |
| 086 | CH$_3$ | 4-CF$_3$O—Ph | CH(CH$_3$)CH$_2$ |
| 087 | C$_2$H$_5$ | 4-CF$_3$O—Ph | CH(CH$_3$)CH$_2$ |
| 088 | C$_3$H$_7$-n | 4-CF$_3$O—Ph | CH(CH$_3$)CH$_2$ |
| 089 | C$_3$H$_7$-i | 4-CF$_3$O—Ph | CH(CH$_3$)CH$_2$ |
| 090 | C$_4$H$_9$-n | 4-CF$_3$O—Ph | CH(CH$_3$)CH$_2$ |
| 091 | CH$_3$ | 3,4-di-OCH$_3$—Ph | CH$_2$CH$_2$ |
| 092 | C$_2$H$_5$ | 3,4-di-OCH$_3$—Ph | CH$_2$CH$_2$ |
| 093 | C$_3$H$_7$-n | 3,4-di-OCH$_3$—Ph | CH$_2$CH$_2$ |
| 094 | C$_3$H$_7$-i | 3,4-di-OCH$_3$—Ph | CH$_2$CH$_2$ |
| 095 | C$_4$H$_9$-n | 3,4-di-OCH$_3$—Ph | CH$_2$CH$_2$ |
| 096 | CH$_3$ | 3,4-di-OCH$_3$—Ph | CH(CH$_3$)CH$_2$ |
| 097 | C$_2$H$_5$ | 3,4-di-OCH$_3$—Ph | CH(CH$_3$)CH$_2$ |
| 098 | C$_3$H$_7$-n | 3,4-di-OCH$_3$—Ph | CH(CH$_3$)CH$_2$ |
| 099 | C$_3$H$_7$-i | 3,4-di-OCH$_3$—Ph | CH(CH$_3$)CH$_2$ |
| 100 | C$_4$H$_9$-n | 3,4-di-OCH$_3$—Ph | CH(CH$_3$)CH$_2$ |
| 101 | CH$_3$ | 3,4-OCH$_2$—O—Ph | CH$_2$CH$_2$ |
| 102 | C$_2$H$_5$ | 3,4-OCH$_2$—O—Ph | CH$_2$CH$_2$ |
| 103 | C$_3$H$_7$-n | 3,4-OCH$_2$—O—Ph | CH$_2$CH$_2$ |
| 104 | C$_3$H$_7$-i | 3,4-OCH$_2$—O—Ph | CH$_2$CH$_2$ |
| 105 | C$_4$H$_9$-n | 3,4-OCH$_2$—O—Ph | CH$_2$CH$_2$ |
| 106 | CH$_3$ | 3,4-OCH$_2$—O—Ph | CH(CH$_3$)CH$_2$ |
| 107 | C$_2$H$_5$ | 3,4-OCH$_2$—O—Ph | CH(CH$_3$)CH$_2$ |
| 108 | C$_3$H$_7$-n | 3,4-OCH$_2$—O—Ph | CH(CH$_3$)CH$_2$ |
| 109 | C$_3$H$_7$-i | 3,4-OCH$_2$—O—Ph | CH(CH$_3$)CH$_2$ |
| 110 | C$_4$H$_9$-n | 3,4-OCH$_2$—O—Ph | CH(CH$_3$)CH$_2$ |
| 111 | CH$_3$ | 3,4-di-F—Ph | CH$_2$CH$_2$ |
| 112 | C$_2$H$_5$ | 3,4-di-F—Ph | CH$_2$CH$_2$ |
| 113 | C$_3$H$_7$-n | 3,4-di-F—Ph | CH$_2$CH$_2$ |
| 114 | C$_3$H$_7$-i | 3,4-di-F—Ph | CH$_2$CH$_2$ |
| 115 | C$_4$H$_9$-n | 3,4-di-F—Ph | CH$_2$CH$_2$ |
| 116 | CH$_3$ | 3,4-di-F—Ph | CH(CH$_3$)CH$_2$ |
| 117 | C$_2$H$_5$ | 3,4-di-F—Ph | CH(CH$_3$)CH$_2$ |
| 118 | C$_3$H$_7$-n | 3,4-di-F—Ph | CH(CH$_3$)CH$_2$ |
| 119 | C$_3$H$_7$-i | 3,4-di-F—Ph | CH(CH$_3$)CH$_2$ |
| 120 | C$_4$H$_9$-n | 3,4-di-F—Ph | CH(CH$_3$)CH$_2$ |
| 121 | CH$_3$ | 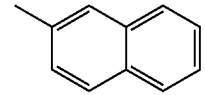 | CH$_2$CH$_2$ |
| 122 | C$_2$H$_5$ | 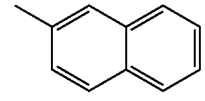 | CH$_2$CH$_2$ |
| 123 | C$_3$H$_7$-n | 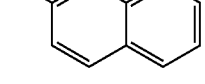 | CH$_2$CH$_2$ |
| 124 | C$_3$H$_7$-i | 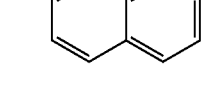 | CH$_2$CH$_2$ |
| 125 | C$_4$H$_9$-n | 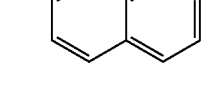 | CH$_2$CH$_2$ |
| 126 | CH$_3$ | 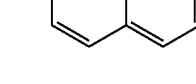 | CH(CH$_3$)CH$_2$ |
| 127 | C$_2$H$_5$ | 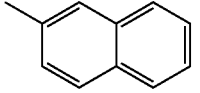 | CH(CH$_3$)CH$_2$ |
| 128 | C$_3$H$_7$-n | 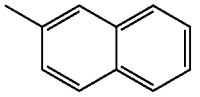 | CH(CH$_3$)CH$_2$ |
| 129 | C$_3$H$_7$-i | 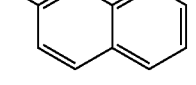 | CH(CH$_3$)CH$_2$ |
| 130 | C$_4$H$_9$-n | 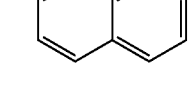 | CH(CH$_3$)CH$_2$ |
| 131 | CH$_3$ | 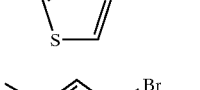 | CH$_2$CH$_2$ |
| 132 | C$_2$H$_5$ | 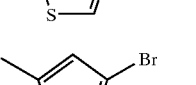 | CH$_2$CH$_2$ |
| 133 | C$_3$H$_7$-n | 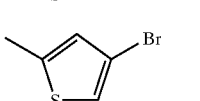 | CH$_2$CH$_2$ |
| 134 | C$_3$H$_7$-i | 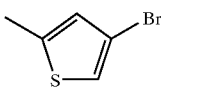 | CH$_2$CH$_2$ |
| 135 | C$_4$H$_9$-n | 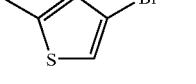 | CH$_2$CH$_2$ |
| 136 | CH$_3$ | 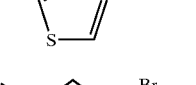 | CH(CH$_3$)CH$_2$ |
| 137 | C$_2$H$_5$ | 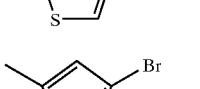 | CH(CH$_3$)CH$_2$ |
| 138 | C$_3$H$_7$-n | 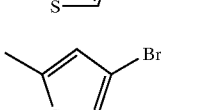 | CH(CH$_3$)CH$_2$ |
| 139 | C$_3$H$_7$-i | 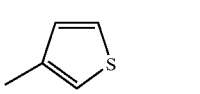 | CH(CH$_3$)CH$_2$ |
| 140 | C$_4$H$_9$-n |  | CH(CH$_3$)CH$_2$ |
| 141 | CH$_3$ |  | CH$_2$CH$_2$ |

TABLE B-continued

| | R | A | B |
|---|---|---|---|
| 142 | C$_2$H$_5$ | 3-methylthiophen-yl | CH$_2$CH$_2$ |
| 143 | C$_3$H$_7$-n | 3-methylthiophen-yl | CH$_2$CH$_2$ |
| 144 | C$_3$H$_7$-i | 3-methylthiophen-yl | CH$_2$CH$_2$ |
| 145 | C$_4$H$_9$-n | 3-methylthiophen-yl | CH$_2$CH$_2$ |
| 146 | CH$_3$ | 3-methylthiophen-yl | CH(CH$_3$)CH$_2$ |
| 147 | C$_2$H$_5$ | 3-methylthiophen-yl | CH(CH$_3$)CH$_2$ |
| 148 | C$_3$H$_7$-n | 3-methylthiophen-yl | CH(CH$_3$)CH$_2$ |
| 149 | C$_3$H$_7$-i | 3-methylthiophen-yl | CH(CH$_3$)CH$_2$ |
| 150 | C$_4$H$_9$-n | 3-methylthiophen-yl | CH(CH$_3$)CH$_2$ |
| 151 | CH$_3$ | 4-Ph—Ph | CH$_2$CH$_2$ |
| 152 | C$_2$H$_5$ | 4-Ph—Ph | CH$_2$CH$_2$ |
| 153 | C$_3$H$_7$-n | 4-Ph—Ph | CH$_2$CH$_2$ |
| 154 | C$_3$H$_7$-i | 4-Ph—Ph | CH$_2$CH$_2$ |
| 155 | C$_4$H$_9$-n | 4-Ph—Ph | CH$_2$CH$_2$ |
| 156 | CH$_3$ | 4-Ph—Ph | CH(CH$_3$)CH$_2$ |
| 157 | C$_2$H$_5$ | 4-Ph—Ph | CH(CH$_3$)CH$_2$ |
| 158 | C$_3$H$_7$-n | 4-Ph—Ph | CH(CH$_3$)CH$_2$ |
| 159 | C$_3$H$_7$-i | 4-Ph—Ph | CH(CH$_3$)CH$_2$ |
| 160 | C$_4$H$_9$-n | 4-Ph—Ph | CH(CH$_3$)CH$_2$ |
| 161 | CH$_3$ | 4'-Cl—Ph-4-Ph | CH$_2$CH$_2$ |
| 162 | C$_2$H$_5$ | 4'-Cl—Ph-4-Ph | CH$_2$CH$_2$ |
| 163 | C$_3$H$_7$-n | 4'-Cl—Ph-4-Ph | CH$_2$CH$_2$ |
| 164 | C$_3$H$_7$-i | 4'-Cl—Ph-4-Ph | CH$_2$CH$_2$ |
| 165 | C$_4$H$_9$-n | 4'-Cl—Ph-4-Ph | CH$_2$CH$_2$ |
| 166 | CH$_3$ | 4'-Cl—Ph-4-Ph | CH(CH$_3$)CH$_2$ |
| 167 | C$_2$H$_5$ | 4'-Cl—Ph-4-Ph | CH(CH$_3$)CH$_2$ |
| 168 | C$_3$H$_7$-n | 4'-Cl—Ph-4-Ph | CH(CH$_3$)CH$_2$ |
| 169 | C$_3$H$_7$-i | 4'-Cl—Ph-4-Ph | CH(CH$_3$)CH$_2$ |
| 170 | C$_4$H$_9$-n | 4'-Cl—Ph-4-Ph | CH(CH$_3$)CH$_2$ |
| 171 | CH$_3$ | 4'-CH$_3$—Ph-4-Ph | CH$_2$CH$_2$ |
| 172 | C$_2$H$_5$ | 4'-CH$_3$—Ph-4-Ph | CH$_2$CH$_2$ |
| 173 | C$_3$H$_7$-n | 4'-CH$_3$—Ph-4-Ph | CH$_2$CH$_2$ |
| 174 | C$_3$H$_7$-i | 4'-CH$_3$—Ph-4-Ph | CH$_2$CH$_2$ |
| 175 | C$_4$H$_9$-n | 4'-CH$_3$—Ph-4-Ph | CH$_2$CH$_2$ |
| 176 | CH$_3$ | 4'-CH$_3$—Ph-4-Ph | CH(CH$_3$)CH$_2$ |
| 177 | C$_2$H$_5$ | 4'-CH$_3$—Ph-4-Ph | CH(CH$_3$)CH$_2$ |
| 178 | C$_3$H$_7$-n | 4'-CH$_3$—Ph-4-Ph | CH(CH$_3$)CH$_2$ |
| 179 | C$_3$H$_7$-i | 4'-CH$_3$—Ph-4-Ph | CH(CH$_3$)CH$_2$ |
| 180 | C$_4$H$_9$-n | 4'-CH$_3$—Ph-4-Ph | CH(CH$_3$)CH$_2$ |
| 181 | CH$_3$ | 3,4-di-CH$_3$—Ph | CH$_2$CH$_2$ |
| 182 | C$_2$H$_5$ | 3,4-di-CH$_3$—Ph | CH$_2$CH$_2$ |
| 183 | C$_3$H$_7$-n | 3,4-di-CH$_3$—Ph | CH$_2$CH$_2$ |
| 184 | C$_3$H$_7$-i | 3,4-di-CH$_3$—Ph | CH$_2$CH$_2$ |
| 185 | C$_4$H$_9$-n | 3,4-di-CH$_3$—Ph | CH$_2$CH$_2$ |
| 186 | CH$_3$ | 3,4-di-CH$_3$—Ph | CH(CH$_3$)CH$_2$ |
| 187 | C$_2$H$_5$ | 3,4-di-CH$_3$—Ph | CH(CH$_3$)CH$_2$ |
| 188 | C$_3$H$_7$-n | 3,4-di-CH$_3$—Ph | CH(CH$_3$)CH$_2$ |
| 189 | C$_3$H$_7$-i | 3,4-di-CH$_3$—Ph | CH(CH$_3$)CH$_2$ |
| 190 | C$_4$H$_9$-n | 3,4-di-CH$_3$—Ph | CH(CH$_3$)CH$_2$ |
| 191 | CH$_3$ | 4-cycl-C$_6$H$_{11}$—Ph | CH$_2$CH$_2$ |
| 192 | C$_2$H$_5$ | 4-cycl-C$_6$H$_{11}$—Ph | CH$_2$CH$_2$ |
| 193 | C$_3$H$_7$-n | 4-cycl-C$_6$H$_{11}$—Ph | CH$_2$CH$_2$ |
| 194 | C$_3$H$_7$-i | 4-cycl-C$_6$H$_{11}$—Ph | CH$_2$CH$_2$ |
| 195 | C$_4$H$_9$-n | 4-cycl-C$_6$H$_{11}$—Ph | CH$_2$CH$_2$ |
| 196 | CH$_3$ | 4-cycl-C$_6$H$_{11}$—Ph | CH(CH$_3$)CH$_2$ |
| 197 | C$_2$H$_5$ | 4-cycl-C$_6$H$_{11}$—Ph | CH(CH$_3$)CH$_2$ |
| 198 | C$_3$H$_7$-n | 4-cycl-C$_6$H$_{11}$—Ph | CH(CH$_3$)CH$_2$ |
| 199 | C$_3$H$_7$-i | 4-cycl-C$_6$H$_{11}$—Ph | CH(CH$_3$)CH$_2$ |
| 200 | C$_4$H$_9$-n | 4-cycl-C$_6$H$_{11}$—Ph | CH(CH$_3$)CH$_2$ |
| 201 | CH$_3$ | 4-[N(CH$_3$)$_2$]—Ph | CH$_2$CH$_2$ |
| 202 | C$_2$H$_5$ | 4-[N(CH$_3$)$_2$]—Ph | CH$_2$CH$_2$ |
| 203 | C$_3$H$_7$-n | 4-[N(CH$_3$)$_2$]—Ph | CH$_2$CH$_2$ |
| 204 | C$_3$H$_7$-i | 4-[N(CH$_3$)$_2$]—Ph | CH$_2$CH$_2$ |
| 205 | C$_4$H$_9$-n | 4-[N(CH$_3$)$_2$]—Ph | CH$_2$CH$_2$ |
| 206 | CH$_3$ | 4-[N(CH$_3$)$_2$]—Ph | CH(CH$_3$)CH$_2$ |
| 207 | C$_2$H$_5$ | 4-[N(CH$_3$)$_2$]—Ph | CH(CH$_3$)CH$_2$ |
| 208 | C$_3$H$_7$-n | 4-[N(CH$_3$)$_2$]—Ph | CH(CH$_3$)CH$_2$ |
| 209 | C$_3$H$_7$-i | 4-[N(CH$_3$)$_2$]—Ph | CH(CH$_3$)CH$_2$ |
| 210 | C$_4$H$_9$-n | 4-[N(CH$_3$)$_2$]—Ph | CH(CH$_3$)CH$_2$ |
| 211 | CH$_3$ | 4-CN—Ph | CH$_2$CH$_2$ |
| 212 | C$_2$H$_5$ | 4-CN—Ph | CH$_2$CH$_2$ |
| 213 | C$_3$H$_7$-n | 4-CN—Ph | CH$_2$CH$_2$ |
| 214 | C$_3$H$_7$-i | 4-CN—Ph | CH$_2$CH$_2$ |
| 215 | C$_4$H$_9$-n | 4-CN—Ph | CH$_2$CH$_2$ |
| 216 | CH$_3$ | 4-CN—Ph | CH(CH$_3$)CH$_2$ |
| 217 | C$_2$H$_5$ | 4-CN—Ph | CH(CH$_3$)CH$_2$ |
| 218 | C$_3$H$_7$-n | 4-CN—Ph | CH(CH$_3$)CH$_2$ |
| 219 | C$_3$H$_7$-i | 4-CN—Ph | CH(CH$_3$)CH$_2$ |
| 220 | C$_4$H$_9$-n | 4-CN—Ph | CH(CH$_3$)CH$_2$ |
| 221 | CH$_3$ | 2-methylthiophen-yl | CH$_2$CH$_2$ |
| 222 | C$_2$H$_5$ | 2-methylthiophen-yl | CH$_2$CH$_2$ |
| 223 | C$_3$H$_7$-n | 2-methylthiophen-yl | CH$_2$CH$_2$ |
| 224 | C$_3$H$_7$-i | 2-methylthiophen-yl | CH$_2$CH$_2$ |
| 225 | C$_4$H$_9$-n | 2-methylthiophen-yl | CH$_2$CH$_2$ |
| 226 | CH$_3$ | 2-methylthiophen-yl | CH(CH$_3$)CH$_2$ |
| 227 | C$_2$H$_5$ | 2-methylthiophen-yl | CH(CH$_3$)CH$_2$ |
| 228 | C$_3$H$_7$-n | 2-methylthiophen-yl | CH(CH$_3$)CH$_2$ |

TABLE B-continued

| | R | A | B |
|---|---|---|---|
| 229 | C$_3$H$_7$-i | 2-methylthiophene | CH(CH$_3$)CH$_2$ |
| 230 | C$_4$H$_9$-n | 2-methylthiophene | CH(CH$_3$)CH$_2$ |
| 231 | CH$_3$ | 2-methylfuran | CH$_2$CH$_2$ |
| 232 | C$_2$H$_5$ | 2-methylfuran | CH$_2$CH$_2$ |
| 233 | C$_3$H$_7$-n | 2-methylfuran | CH$_2$CH$_2$ |
| 234 | C$_3$H$_7$-i | 2-methylfuran | CH$_2$CH$_2$ |
| 235 | C$_4$H$_9$-n | 2-methylfuran | CH$_2$CH$_2$ |
| 236 | CH$_3$ | 2-methylfuran | CH(CH$_3$)CH$_2$ |
| 237 | C$_2$H$_5$ | 2-methylfuran | CH(CH$_3$)CH$_2$ |
| 238 | C$_3$H$_7$-n | 2-methylfuran | CH(CH$_3$)CH$_2$ |
| 239 | C$_3$H$_7$-i | 2-methylfuran | CH(CH$_3$)CH$_2$ |
| 240 | C$_4$H$_9$-n | 2-methylfuran | CH(CH$_3$)CH$_2$ |
| 241 | CH$_3$ | 3-methylpyridine | CH$_2$CH$_2$ |
| 242 | C$_2$H$_5$ | 3-methylpyridine | CH$_2$CH$_2$ |
| 243 | C$_3$H$_7$-n | 3-methylpyridine | CH$_2$CH$_2$ |
| 244 | C$_3$H$_7$-i | 3-methylpyridine | CH$_2$CH$_2$ |
| 245 | C$_4$H$_9$-n | 3-methylpyridine | CH$_2$CH$_2$ |
| 246 | CH$_3$ | 3-methylpyridine | CH(CH$_3$)CH$_2$ |
| 247 | C$_2$H$_5$ | 3-methylpyridine | CH(CH$_3$)CH$_2$ |
| 248 | C$_3$H$_7$-n | 3-methylpyridine | CH(CH$_3$)CH$_2$ |
| 249 | C$_3$H$_7$-i | 3-methylpyridine | CH(CH$_3$)CH$_2$ |
| 250 | C$_4$H$_9$-n | 3-methylpyridine | CH(CH$_3$)CH$_2$ |
| 251 | CH$_3$ | 4-C$_3$H$_7$-i-Ph | CH$_2$CH$_2$ |
| 252 | C$_2$H$_5$ | 4-C$_3$H$_7$-i-Ph | CH$_2$CH$_2$ |
| 253 | C$_3$H$_7$-n | 4-C$_3$H$_7$-i-Ph | CH$_2$CH$_2$ |
| 254 | C$_3$H$_7$-i | 4-C$_3$H$_7$-i-Ph | CH$_2$CH$_2$ |
| 255 | C$_4$H$_9$-n | 4-C$_3$H$_7$-i-Ph | CH$_2$CH$_2$ |
| 256 | CH$_3$ | 4-C$_3$H$_7$-i-Ph | CH(CH$_3$)CH$_2$ |
| 257 | C$_2$H$_5$ | 4-C$_3$H$_7$-i-Ph | CH(CH$_3$)CH$_2$ |
| 258 | C$_3$H$_7$-n | 4-C$_3$H$_7$-i-Ph | CH(CH$_3$)CH$_2$ |
| 259 | C$_3$H$_7$-i | 4-C$_3$H$_7$-i-Ph | CH(CH$_3$)CH$_2$ |
| 260 | C$_4$H$_9$-n | 4-C$_3$H$_7$-i-Ph | CH(CH$_3$)CH$_2$ |
| 261 | CH$_3$ | 4-C$_4$H$_9$-t-Ph | CH$_2$CH$_2$ |
| 262 | C$_2$H$_5$ | 4-C$_4$H$_9$-t-Ph | CH$_2$CH$_2$ |
| 263 | C$_3$H$_7$-n | 4-C$_4$H$_9$-t-Ph | CH$_2$CH$_2$ |
| 264 | C$_3$H$_7$-i | 4-C$_4$H$_9$-t-Ph | CH$_2$CH$_2$ |
| 265 | C$_4$H$_9$-n | 4-C$_4$H$_9$-t-Ph | CH$_2$CH$_2$ |
| 266 | CH$_3$ | 4-C$_4$H$_9$-t-Ph | CH(CH$_3$)CH$_2$ |
| 267 | C$_2$H$_5$ | 4-C$_4$H$_9$-t-Ph | CH(CH$_3$)CH$_2$ |
| 268 | C$_3$H$_7$-n | 4-C$_4$H$_9$-t-Ph | CH(CH$_3$)CH$_2$ |
| 269 | C$_3$H$_7$-i | 4-C$_4$H$_9$-t-Ph | CH(CH$_3$)CH$_2$ |
| 270 | C$_4$H$_9$-n | 4-C$_4$H$_9$-t-Ph | CH(CH$_3$)CH$_2$ |
| 271 | CH$_3$ | 3-methyl-1H-pyrazole | CH$_2$CH$_2$ |
| 272 | C$_2$H$_5$ | 3-methyl-1H-pyrazole | CH$_2$CH$_2$ |
| 273 | C$_3$H$_7$-n | 3-methyl-1H-pyrazole | CH$_2$CH$_2$ |

TABLE B-continued

| | R | A | B |
|---|---|---|---|
| 274 | C₃H₇-i | 3-methyl-1H-pyrazol-5-yl | CH₂CH₂ |
| 275 | C₄H₉-n | 3-methyl-1H-pyrazol-5-yl | CH₂CH₂ |
| 276 | CH₃ | 3-methyl-1H-pyrazol-5-yl | CH(CH₃)CH₂ |
| 277 | C₂H₅ | 3-methyl-1H-pyrazol-5-yl | CH(CH₃)CH₂ |
| 278 | C₃H₇-n | 3-methyl-1H-pyrazol-5-yl | CH(CH₃)CH₂ |
| 279 | C₃H₇-i | 3-methyl-1H-pyrazol-5-yl | CH(CH₃)CH₂ |
| 280 | C₄H₉-n | 3-methyl-1H-pyrazol-5-yl | CH(CH₃)CH₂ |
| 281 | CH₃ | 2-methylthiazol-5-yl | CH₂CH₂ |
| 282 | C₂H₅ | 2-methylthiazol-5-yl | CH₂CH₂ |
| 283 | C₃H₇-n | 2-methylthiazol-5-yl | CH₂CH₂ |
| 284 | C₃H₇-i | 2-methylthiazol-5-yl | CH₂CH₂ |
| 285 | C₄H₉-n | 2-methylthiazol-5-yl | CH₂CH₂ |
| 286 | CH₃ | 2-methylthiazol-5-yl | CH(CH₃)CH₂ |
| 287 | C₂H₅ | 2-methylthiazol-5-yl | CH(CH₃)CH₂ |
| 288 | C₃H₇-n | 2-methylthiazol-5-yl | CH(CH₃)CH₂ |
| 289 | C₃H₇-i | 2-methylthiazol-5-yl | CH(CH₃)CH₂ |
| 290 | C₄H₉-n | 2-methylthiazol-5-yl | CH(CH₃)CH₂ |
| 291 | CH₃ | 2-methyl-1H-pyrrol-5-yl | CH₂CH₂ |
| 292 | C₂H₅ | 2-methyl-1H-pyrrol-5-yl | CH₂CH₂ |
| 293 | C₃H₇-n | 2-methyl-1H-pyrrol-5-yl | CH₂CH₂ |
| 294 | C₃H₇-i | 2-methyl-1H-pyrrol-5-yl | CH₂CH₂ |
| 295 | C₄H₉-n | 2-methyl-1H-pyrrol-5-yl | CH₂CH₂ |
| 296 | CH₃ | 2-methyl-1H-pyrrol-5-yl | CH(CH₃)CH₂ |
| 297 | C₂H₅ | 2-methyl-1H-pyrrol-5-yl | CH(CH₃)CH₂ |
| 298 | C₃H₇-n | 2-methyl-1H-pyrrol-5-yl | CH(CH₃)CH₂ |
| 299 | C₃H₇-i | 2-methyl-1H-pyrrol-5-yl | CH(CH₃)CH₂ |
| 300 | C₄H₉-n | 2-methyl-1H-pyrrol-5-yl | CH(CH₃)CH₂ |
| 301 | CH₃ | 2-methyl-1H-imidazol-5-yl | CH₂CH₂ |

TABLE B-continued

| | R | A | B |
|---|---|---|---|
| 302 | $C_2H_5$ | 2-methylimidazol-1-yl | $CH_2CH_2$ |
| 303 | $C_3H_7$-n | 2-methylimidazol-1-yl | $CH_2CH_2$ |
| 304 | $C_3H_7$-i | 2-methylimidazol-1-yl | $CH_2CH_2$ |
| 305 | $C_4H_9$-n | 2-methylimidazol-1-yl | $CH_2CH_2$ |
| 306 | $CH_3$ | 2-methylimidazol-1-yl | $CH(CH_3)CH_2$ |
| 307 | $C_2H_5$ | 2-methylimidazol-1-yl | $CH(CH_3)CH_2$ |
| 308 | $C_3H_7$-n | 2-methylimidazol-1-yl | $CH(CH_3)CH_2$ |
| 309 | $C_3H_7$-i | 2-methylimidazol-1-yl | $CH(CH_3)CH_2$ |
| 310 | $C_4H_9$-n | 2-methylimidazol-1-yl | $CH(CH_3)CH_2$ |
| 311 | $CH_3$ | 3-OCH$_3$-4-(OCH$_2$C≡CH)-phenyl | $CH_2CH_2$ |
| 312 | $C_2H_5$ | 3-OCH$_3$-4-(OCH$_2$C≡CH)-phenyl | $CH_2CH_2$ |
| 313 | $C_3H_7$-n | 3-OCH$_3$-4-(OCH$_2$C≡CH)-phenyl | $CH_2CH_2$ |
| 314 | $C_3H_7$-i | 3-OCH$_3$-4-(OCH$_2$C≡CH)-phenyl | $CH_2CH_2$ |
| 315 | $C_4H_9$-n | 3-OCH$_3$-4-(OCH$_2$C≡CH)-phenyl | $CH_2CH_2$ |
| 316 | $CH_3$ | 3-OCH$_3$-4-(OCH$_2$C≡CH)-phenyl | $CH(CH_3)CH_2$ |
| 317 | $C_2H_5$ | 3-OCH$_3$-4-(OCH$_2$C≡CH)-phenyl | $CH(CH_3)CH_2$ |
| 318 | $C_3H_7$-n | 3-OCH$_3$-4-(OCH$_2$C≡CH)-phenyl | $CH(CH_3)CH_2$ |
| 319 | $C_3H_7$-i | 3-OCH$_3$-4-(OCH$_2$C≡CH)-phenyl | $CH(CH_3)CH_2$ |
| 320 | $C_4H_9$-n | 3-OCH$_3$-4-(OCH$_2$C≡CH)-phenyl | $CH(CH_3)CH_2$ |
| 321 | $CH_3$ | 3',4'-Cl$_2$—Ph-4-Ph | $CH_2CH_2$ |
| 322 | $C_2H_5$ | 3',4'-Cl$_2$—Ph-4-Ph | $CH_2CH_2$ |
| 323 | $C_3H_7$-n | 3',4'-Cl$_2$—Ph-4-Ph | $CH_2CH_2$ |
| 324 | $C_3H_7$-i | 3',4'-Cl$_2$—Ph-4-Ph | $CH_2CH_2$ |
| 325 | $C_4H_9$-n | 3',4'-Cl$_2$—Ph-4-Ph | $CH_2CH_2$ |
| 326 | $CH_3$ | 3',4'-Cl$_2$—Ph-4-Ph | $CH(CH_3)CH_2$ |
| 327 | $C_2H_5$ | 3',4'-Cl$_2$—Ph-4-Ph | $CH(CH_3)CH_2$ |
| 328 | $C_3H_7$-n | 3',4'-Cl$_2$—Ph-4-Ph | $CH(CH_3)CH_2$ |
| 329 | $C_3H_7$-i | 3',4'-Cl$_2$—Ph-4-Ph | $CH(CH_3)CH_2$ |
| 330 | $C_4H_9$-n | 3',4'-Cl$_2$—Ph-4-Ph | $CH(CH_3)CH_2$ |
| 331 | $CH_3$ | 4'-CF$_3$—Ph-4-Ph | $CH_2CH_2$ |
| 332 | $C_2H_5$ | 4'-CF$_3$—Ph-4-Ph | $CH_2CH_2$ |
| 333 | $C_3H_7$-n | 4'-CF$_3$—Ph-4-Ph | $CH_2CH_2$ |
| 334 | $C_3H_7$-i | 4'-CF$_3$—Ph-4-Ph | $CH_2CH_2$ |
| 335 | $C_4H_9$-n | 4'-CF$_3$—Ph-4-Ph | $CH_2CH_2$ |
| 336 | $CH_3$ | 4'-CF$_3$—Ph-4-Ph | $CH(CH_3)CH_2$ |
| 337 | $C_2H_5$ | 4'-CF$_3$—Ph-4-Ph | $CH(CH_3)CH_2$ |
| 338 | $C_3H_7$-n | 4'-CF$_3$—Ph-4-Ph | $CH(CH_3)CH_2$ |
| 339 | $C_3H_7$-i | 4'-CF$_3$—Ph-4-Ph | $CH(CH_3)CH_2$ |
| 340 | $C_4H_9$-n | 4'-CF$_3$—Ph-4-Ph | $CH(CH_3)CH_2$ |
| 341 | $CH_3$ | 4'-CF$_3$—O—Ph-4-Ph | $CH_2CH_2$ |
| 342 | $C_2H_5$ | 4'-CF$_3$—O—Ph-4-Ph | $CH_2CH_2$ |
| 343 | $C_3H_7$-n | 4'-CF$_3$—O—Ph-4-Ph | $CH_2CH_2$ |
| 344 | $C_3H_7$-i | 4'-CF$_3$—O—Ph-4-Ph | $CH_2CH_2$ |
| 345 | $C_4H_9$-n | 4'-CF$_3$—O—Ph-4-Ph | $CH_2CH_2$ |
| 346 | $CH_3$ | 4'-CF$_3$—O—Ph-4-Ph | $CH(CH_3)CH_2$ |
| 347 | $C_2H_5$ | 4'-CF$_3$—O—Ph-4-Ph | $CH(CH_3)CH_2$ |
| 348 | $C_3H_7$-n | 4'-CF$_3$—O—Ph-4-Ph | $CH(CH_3)CH_2$ |
| 349 | $C_3H_7$-i | 4'-CF$_3$—O—Ph-4-Ph | $CH(CH_3)CH_2$ |
| 350 | $C_4H_9$-n | 4'-CF$_3$—O—Ph-4-Ph | $CH(CH_3)CH_2$ |
| 351 | $CH_3$ | 4'-C$_4$H$_9$-t-Ph-4-Ph | $CH_2CH_2$ |
| 352 | $C_2H_5$ | 4'-C$_4$H$_9$-t-Ph-4-Ph | $CH_2CH_2$ |
| 353 | $C_3H_7$-n | 4'-C$_4$H$_9$-t-Ph-4-Ph | $CH_2CH_2$ |
| 354 | $C_3H_7$-i | 4'-C$_4$H$_9$-t-Ph-4-Ph | $CH_2CH_2$ |
| 355 | $C_4H_9$-n | 4'-C$_4$H$_9$-t-Ph-4-Ph | $CH_2CH_2$ |
| 356 | $CH_3$ | 4'-C$_4$H$_9$-t-Ph-4-Ph | $CH(CH_3)CH_2$ |
| 357 | $C_2H_5$ | 4'-C$_4$H$_9$-t-Ph-4-Ph | $CH(CH_3)CH_2$ |
| 358 | $C_3H_7$-n | 4'-C$_4$H$_9$-t-Ph-4-Ph | $CH(CH_3)CH_2$ |
| 359 | $C_3H_7$-i | 4'-C$_4$H$_9$-t-Ph-4-Ph | $CH(CH_3)CH_2$ |
| 360 | $C_4H_9$-n | 4'-C$_4$H$_9$-t-Ph-4-Ph | $CH(CH_3)CH_2$ |
| 361 | $CH_3$ | 4'-F—Ph-4-Ph | $CH_2CH_2$ |
| 362 | $C_2H_5$ | 4'-F—Ph-4-Ph | $CH_2CH_2$ |
| 363 | $C_3H_7$-n | 4'-F—Ph-4-Ph | $CH_2CH_2$ |
| 364 | $C_3H_7$-i | 4'-F—Ph-4-Ph | $CH_2CH_2$ |
| 365 | $C_4H_9$-n | 4'-F—Ph-4-Ph | $CH_2CH_2$ |

TABLE B-continued

| | R | A | B |
|---|---|---|---|
| 366 | CH$_3$ | 4'-F—Ph-4-Ph | CH(CH$_3$)CH$_2$ |
| 367 | C$_2$H$_5$ | 4'-F—Ph-4-Ph | CH(CH$_3$)CH$_2$ |
| 368 | C$_3$H$_7$-n | 4'-F—Ph-4-Ph | CH(CH$_3$)CH$_2$ |
| 369 | C$_3$H$_7$-i | 4'-F—Ph-4-Ph | CH(CH$_3$)CH$_2$ |
| 370 | C$_4$H$_9$-n | 4'-F—Ph-4-Ph | CH(CH$_3$)CH$_2$ |
| 371 | CH$_3$ | 3'-CH$_3$—O—Ph-4-Ph | CH$_2$CH$_2$ |
| 372 | C$_2$H$_5$ | 3'-CH$_3$—O—Ph-4-Ph | CH$_2$CH$_2$ |
| 373 | C$_3$H$_7$-n | 3'-CH$_3$—O—Ph-4-Ph | CH$_2$CH$_2$ |
| 374 | C$_3$H$_7$-i | 3'-CH$_3$—O—Ph-4-Ph | CH$_2$CH$_2$ |
| 375 | C$_4$H$_9$-n | 3'-CH$_3$—O—Ph-4-Ph | CH$_2$CH$_2$ |
| 376 | CH$_3$ | 3'-CH$_3$—O—Ph-4-Ph | CH(CH$_3$)CH$_2$ |
| 377 | C$_2$H$_5$ | 3'-CH$_3$—O—Ph-4-Ph | CH(CH$_3$)CH$_2$ |
| 378 | C$_3$H$_7$-n | 3'-CH$_3$—O—Ph-4-Ph | CH(CH$_3$)CH$_2$ |
| 379 | C$_3$H$_7$-i | 3'-CH$_3$—O—Ph-4-Ph | CH(CH$_3$)CH$_2$ |
| 380 | C$_4$H$_9$-n | 3'-CH$_3$—O—Ph-4-Ph | CH(CH$_3$)CH$_2$ |

TABLE C

| | W | Z |
|---|---|---|
| 001 | O | Ph |
| 002 | O | 6-methyl-4-pyrimidinyloxy-phenyl-CN |
| 003 | CH$_2$O | 2-CH$_3$—Ph |
| 004 | CH$_2$O | 2,5-di-CH$_3$—Ph |
| 005 | CH$_2$O | 3-methyl-1-(4-Cl-phenyl)pyrazol-5-yl |
| 006 | CH$_2$O | 3-methyl-1-(4-CH$_3$-phenyl)pyrazol-5-yl |
| 007 | CH$_2$ON=C(CH$_3$) | Ph |
| 008 | CH$_2$ON=C(CH$_3$) | 4-Cl—Ph |
| 009 | CH$_2$ON=C(CH$_3$) | 4-CF$_3$—Ph |
| 010 | CH$_2$ON=C(CH$_3$) | 3-CF$_3$—Ph |
| 011 | CH$_2$ON=C(CH$_3$) | 3-CF$_3$O—Ph |
| 012 | CH$_2$ON=C-cycl-C$_3$H$_7$ | 4-Cl—Ph |
| 013 | CH$_2$ON=C-cycl-C$_3$H$_7$ | 4-F—Ph |
| 014 | CH$_2$ON=C-cycl-C$_3$H$_7$ | 3-CH$_3$-4-Cl—Ph |
| 015 | CH$_2$ON=C(CH$_3$)C=NOCH$_3$ | CH$_3$ |
| 016 | CH$_2$ON=C(CH$_3$)C=NOCH$_3$ | OCH(CH$_3$)$_2$ |
| 017 | CH$_2$ON=C(CH$_3$)C=NOCH$_3$ | Ph |
| 018 | CH$_2$ON=C(CH$_3$)C=NOCH$_3$ | 4-F—Ph |
| 019 | CH$_2$ON=C(CH$_3$)C=NOCH$_3$ | 4-Cl—Ph |
| 020 | CH$_2$ON=C(CH$_3$)C=NOCH$_3$ | 4-Br—Ph |
| 021 | CH$_2$ON=C(CH$_3$)C=NOCH$_3$ | 4-CH$_3$—Ph |
| 022 | CH$_2$ON=C(CH$_3$)C=NOCH$_3$ | 4-CH$_3$O—Ph |
| 023 | CH$_2$ON=C(CH$_3$)C=NOCH$_3$ | 4-CN—Ph |
| 024 | CH$_2$ON=C(CH$_3$)C=NOCH$_3$ | 3-CF$_3$—Ph |
| 025 | CH$_2$ON=C(CH$_3$)C=NOCH$_3$ | 2-Pyridyl |
| 026 | CH$_2$ON=C(CH$_3$)C=NOCH$_3$ | 4-Pyridyl |
| 027 | CH$_2$ON=C(CH$_3$)C=NOCH$_3$ | 2,4-di-F—Ph |
| 028 | CH=NOCH(CN) | 3-CF$_3$—Ph |
| 029 | CH=NOCH(CH$_3$) | Ph |
| 030 | CH=NOCH(CH$_3$) | 2-Cl—Ph |
| 031 | CH=NOCH(CH$_3$) | 3-Cl—Ph |
| 032 | CH=NOCH(CH$_3$) | 4-Cl—Ph |
| 033 | CH=NOCH(CH$_3$) | 2-CN—Ph |
| 034 | CH=NOCH(CH$_3$) | 3-CF$_3$—Ph |
| 035 | CH=NOCH(CH$_3$) | 4-CF$_3$—Ph |
| 036 | CH=NOCH(CH$_3$) | Ph |
| 037 | CH=NOCH(CH$_3$) | 4-Cl—Ph |
| 038 | CH=N—N=C(CH$_3$)C=NOCH$_3$ | CH$_3$ |
| 039 | CH=N—N=C(CH$_3$)C=NOCH$_3$ | OCH(CH$_3$)$_2$ |
| 040 | CH=N—N=C(CH$_3$)C=NOCH$_3$ | Ph |
| 041 | CH=N—N=C(CH$_3$)C=NOCH$_3$ | 4-F—Ph |
| 042 | CH=N—N=C(CH$_3$)C=NOCH$_3$ | 4-Cl—Ph |
| 043 | CH=N—N=C(CH$_3$)C=NOCH$_3$ | 4-Br—Ph |
| 044 | CH=N—N=C(CH$_3$)C=NOCH$_3$ | 4-CH$_3$—Ph |
| 045 | CH=N—N=C(CH$_3$)C=NOCH$_3$ | 4-OCH$_3$—Ph |
| 046 | CH=N—N=C(CH$_3$)C=NOCH$_3$ | 4-CN—Ph |
| 047 | CH=N—N=C(CH$_3$)C=NOCH$_3$ | 3-CF3—Ph |
| 048 | CH=N—N=C(CH$_3$)C=NOCH$_3$ | 2-Pyridyl |
| 050 | CH=N—N=C(CH$_3$)C=NOCH$_3$ | 4-Pyridyl |
| 051 | O | 5-fluoro-4-methyl-6-(2-chlorophenoxy)pyrimidinyl |
| 052 | CH$_2$O | 6-methyl-2-(trifluoromethyl)pyridinyl |
| 053 | CH$_2$ON=C(CH$_3$) | 3-CF$_3$—Ph |

TABLE D

| | R | A |
|---|---|---|
| 001 | CH$_3$ | 4-Cl—Ph |
| 002 | C$_2$H$_5$ | 4-Cl—Ph |
| 003 | C$_3$H$_7$-n | 4-Cl—Ph |
| 004 | C$_3$H$_7$-i | 4-Cl—Ph |
| 005 | C$_4$H$_9$-n | 4-Cl—Ph |
| 006 | CH$_3$ | 4-Cl—Ph |
| 007 | C$_2$H$_5$ | 4-Cl—Ph |
| 008 | C$_3$H$_7$-n | 4-Cl—Ph |
| 009 | C$_3$H$_7$-i | 4-Cl—Ph |
| 010 | C$_4$H$_9$-n | 4-Cl—Ph |
| 011 | CH$_3$ | 3,4-di-Cl—Ph |
| 012 | C$_2$H$_5$ | 3,4-di-Cl—Ph |
| 013 | C$_3$H$_7$-n | 3,4-di-Cl—Ph |
| 014 | C$_3$H$_7$-i | 3,4-di-Cl—Ph |
| 015 | C$_4$H$_9$-n | 3,4-di-Cl—Ph |
| 016 | CH$_3$ | 3,4-di-Cl—Ph |
| 017 | C$_2$H$_5$ | 3,4-di-Cl—Ph |
| 018 | C$_3$H$_7$-n | 3,4-di-Cl—Ph |
| 019 | C$_3$H$_7$-i | 3,4-di-Cl—Ph |
| 020 | C$_4$H$_9$-n | 3,4-di-Cl—Ph |
| 021 | CH$_3$ | Ph |
| 022 | C$_2$H$_5$ | Ph |
| 023 | C$_3$H$_7$-n | Ph |
| 024 | C$_3$H$_7$-i | Ph |
| 025 | C$_4$H$_9$-n | Ph |
| 026 | CH$_3$ | Ph |
| 027 | C$_2$H$_5$ | Ph |
| 028 | C$_3$H$_7$-n | Ph |
| 029 | C$_3$H$_7$-i | Ph |
| 030 | C$_4$H$_9$-n | Ph |
| 031 | CH$_3$ | 4-Br—Ph |
| 032 | C$_2$H$_5$ | 4-Br—Ph |
| 033 | C$_3$H$_7$-n | 4-Br—Ph |
| 034 | C$_3$H$_7$-i | 4-Br—Ph |
| 035 | C$_4$H$_9$-n | 4-Br—Ph |
| 036 | CH$_3$ | 4-Br—Ph |
| 037 | C$_2$H$_5$ | 4-Br—Ph |
| 038 | C$_3$H$_7$-n | 4-Br—Ph |

TABLE D-continued

| | R | A |
|---|---|---|
| 039 | C$_3$H$_7$-i | 4-Br—Ph |
| 040 | C$_4$H$_9$-n | 4-Br—Ph |
| 041 | CH$_3$ | 4-CH$_3$—Ph |
| 042 | C$_2$H$_5$ | 4-CH$_3$—Ph |
| 043 | C$_3$H$_7$-n | 4-CH$_3$—Ph |
| 044 | C$_3$H$_7$-i | 4-CH$_3$—Ph |
| 045 | C$_4$H$_9$-n | 4-CH$_3$—Ph |
| 046 | CH$_3$ | 4-CH$_3$—Ph |
| 047 | C$_2$H$_5$ | 4-CH$_3$—Ph |
| 048 | C$_3$H$_7$-n | 4-CH$_3$—Ph |
| 049 | C$_3$H$_7$-i | 4-CH$_3$—Ph |
| 050 | C$_4$H$_9$-n | 4-CH$_3$—Ph |
| 051 | CH$_3$ | 4-CH$_3$O—Ph |
| 052 | C$_2$H$_5$ | 4-CH$_3$O—Ph |
| 053 | C$_3$H$_7$-n | 4-CH$_3$O—Ph |
| 054 | C$_3$H$_7$-i | 4-CH$_3$O—Ph |
| 055 | C$_4$H$_9$-n | 4-CH$_3$O—Ph |
| 056 | CH$_3$ | 4-CH$_3$O—Ph |
| 057 | C$_2$H$_5$ | 4-CH$_3$O—Ph |
| 058 | C$_3$H$_7$-n | 4-CH$_3$O—Ph |
| 059 | C$_3$H$_7$-i | 4-CH$_3$O—Ph |
| 060 | C$_4$H$_9$-n | 4-CH$_3$O—Ph |
| 061 | CH$_3$ | 4-CF$_3$—Ph |
| 062 | C$_2$H$_5$ | 4-CF$_3$—Ph |
| 063 | C$_3$H$_7$-n | 4-CF$_3$—Ph |
| 064 | C$_3$H$_7$-i | 4-CF$_3$—Ph |
| 065 | C$_4$H$_9$-n | 4-CF$_3$—Ph |
| 066 | CH$_3$ | 4-CF$_3$—Ph |
| 067 | C$_2$H$_5$ | 4-CF$_3$—Ph |
| 068 | C$_3$H$_7$-n | 4-CF$_3$—Ph |
| 069 | C$_3$H$_7$-i | 4-CF$_3$—Ph |
| 070 | C$_4$H$_9$-n | 4-CF$_3$—Ph |
| 071 | CH$_3$ | 4-F—Ph |
| 072 | C$_2$H$_5$ | 4-F—Ph |
| 073 | C$_3$H$_7$-n | 4-F—Ph |
| 074 | C$_3$H$_7$-i | 4-F—Ph |
| 075 | C$_4$H$_9$-n | 4-F—Ph |
| 076 | CH$_3$ | 4-F—Ph |
| 077 | C$_2$H$_5$ | 4-F—Ph |
| 078 | C$_3$H$_7$-n | 4-F—Ph |
| 079 | C$_3$H$_7$-i | 4-F—Ph |
| 080 | C$_4$H$_9$-n | 4-F—Ph |
| 081 | CH$_3$ | 4-CF$_3$O—Ph |
| 082 | C$_2$H$_5$ | 4-CF$_3$O—Ph |
| 083 | C$_3$H$_7$-n | 4-CF$_3$O—Ph |
| 084 | C$_3$H$_7$-i | 4-CF$_3$O—Ph |
| 085 | C$_4$H$_9$-n | 4-CF$_3$O—Ph |
| 086 | CH$_3$ | 4-CF$_3$O—Ph |
| 087 | C$_2$H$_5$ | 4-CF$_3$O—Ph |
| 088 | C$_3$H$_7$-n | 4-CF$_3$O—Ph |
| 089 | C$_3$H$_7$-i | 4-CF$_3$O—Ph |
| 090 | C$_4$H$_9$-n | 4-CF$_3$O—Ph |
| 091 | CH$_3$ | 3,4-di-OCH$_3$—Ph |
| 092 | C$_2$H$_5$ | 3,4-di-OCH$_3$—Ph |
| 093 | C$_3$H$_7$-n | 3,4-di-OCH$_3$—Ph |
| 094 | C$_3$H$_7$-i | 3,4-di-OCH$_3$—Ph |
| 095 | C$_4$H$_9$-n | 3,4-di-OCH$_3$—Ph |
| 096 | CH$_3$ | 3,4-di-OCH$_3$—Ph |
| 097 | C$_2$H$_5$ | 3,4-di-OCH$_3$—Ph |
| 098 | C$_3$H$_7$-n | 3,4-di-OCH$_3$—Ph |
| 099 | C$_3$H$_7$-i | 3,4-di-OCH$_3$—Ph |
| 100 | C$_4$H$_9$-n | 3,4-di-OCH$_3$—Ph |
| 101 | CH$_3$ | 3,4-OCH$_2$—O—Ph |
| 102 | C$_2$H$_5$ | 3,4-OCH$_2$—O—Ph |
| 103 | C$_3$H$_7$-n | 3,4-OCH$_2$—O—Ph |
| 104 | C$_3$H$_7$-i | 3,4-OCH$_2$—O—Ph |
| 105 | C$_4$H$_9$-n | 3,4-OCH$_2$—O—Ph |
| 106 | CH$_3$ | 3,4-OCH$_2$—O—Ph |
| 107 | C$_2$H$_5$ | 3,4-OCH$_2$—O—Ph |
| 108 | C$_3$H$_7$-n | 3,4-OCH$_2$—O—Ph |
| 109 | C$_3$H$_7$-i | 3,4-OCH$_2$—O—Ph |
| 110 | C$_4$H$_9$-n | 3,4-OCH$_2$—O—Ph |
| 111 | CH$_3$ | 3,4-di-F—Ph |
| 112 | C$_2$H$_5$ | 3,4-di-F—Ph |
| 113 | C$_3$H$_7$-n | 3,4-di-F—Ph |
| 114 | C$_3$H$_7$-i | 3,4-di-F—Ph |
| 115 | C$_4$H$_9$-n | 3,4-di-F—Ph |
| 116 | CH$_3$ | 3,4-di-F—Ph |
| 117 | C$_2$H$_5$ | 3,4-di-F—Ph |
| 118 | C$_3$H$_7$-n | 3,4-di-F—Ph |
| 119 | C$_3$H$_7$-i | 3,4-di-F—Ph |
| 120 | C$_4$H$_9$-n | 3,4-di-F—Ph |

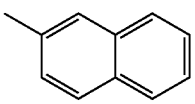

| | R | A |
|---|---|---|
| 121 | CH$_3$ | (2-naphthyl) |
| 122 | C$_2$H$_5$ | (2-naphthyl) |
| 123 | C$_3$H$_7$-n | (2-naphthyl) |
| 124 | C$_3$H$_7$-i | (2-naphthyl) |
| 125 | C$_4$H$_9$-n | (2-naphthyl) |
| 126 | CH$_3$ | (2-naphthyl) |
| 127 | C$_2$H$_5$ | (2-naphthyl) |
| 128 | C$_3$H$_7$-n | (2-naphthyl) |
| 129 | C$_3$H$_7$-i | (2-naphthyl) |
| 130 | C$_4$H$_9$-n | (2-naphthyl) |
| 131 | CH$_3$ | (4-bromo-2-thienyl) |
| 132 | C$_2$H$_5$ | (4-bromo-2-thienyl) |
| 133 | C$_3$H$_7$-n | (4-bromo-2-thienyl) |

TABLE D-continued

| | R | A |
|---|---|---|
| 134 | C₃H₇-i | 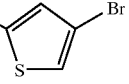 |
| 135 | C₄H₉-n | 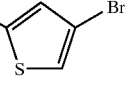 |
| 136 | CH₃ | 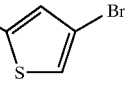 |
| 137 | C₂H₅ | 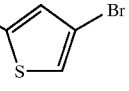 |
| 138 | C₃H₇-n | 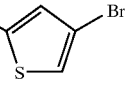 |
| 139 | C₃H₇-i | 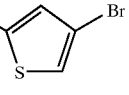 |
| 140 | C₄H₉-n | 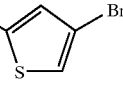 |
| 141 | CH₃ | 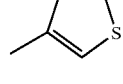 |
| 142 | C₂H₅ | 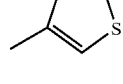 |
| 143 | C₃H₇-n | 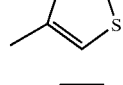 |
| 144 | C₃H₇-i | 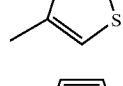 |
| 145 | C₄H₉-n | 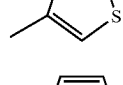 |
| 146 | CH₃ | 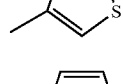 |
| 147 | C₂H₅ | 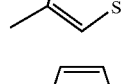 |
| 148 | C₃H₇-n | 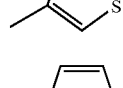 |
| 149 | C₃H₇-i | 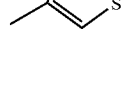 |

TABLE D-continued

| | R | A |
|---|---|---|
| 150 | C₄H₉-n | 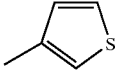 |
| 151 | CH₃ | 4-Ph—Ph |
| 152 | C₂H₅ | 4-Ph—Ph |
| 153 | C₃H₇-n | 4-Ph—Ph |
| 154 | C₃H₇-i | 4-Ph—Ph |
| 155 | C₄H₉-n | 4-Ph—Ph |
| 156 | CH₃ | 4-Ph—Ph |
| 157 | C₂H₅ | 4-Ph—Ph |
| 158 | C₃H₇-n | 4-Ph—Ph |
| 159 | C₃H₇-i | 4-Ph—Ph |
| 160 | C₄H₉-n | 4-Ph—Ph |
| 161 | CH₃ | 4'-Cl-Ph-4-Ph |
| 162 | C₂H₅ | 4'-Cl-Ph-4-Ph |
| 163 | C₃H₇-n | 4'-Cl-Ph-4-Ph |
| 164 | C₃H₇-i | 4'-Cl-Ph-4-Ph |
| 165 | C₄H₉-n | 4'-Cl-Ph-4-Ph |
| 166 | CH₃ | 4'-Cl-Ph-4-Ph |
| 167 | C₂H₅ | 4'-Cl-Ph-4-Ph |
| 168 | C₃H₇-n | 4'-Cl-Ph-4-Ph |
| 169 | C₃H₇-i | 4'-Cl-Ph-4-Ph |
| 170 | C₄H₉-n | 4'-Cl-Ph-4-Ph |
| 171 | CH₃ | 4'-CH₃-Ph-4-Ph |
| 172 | C₂H₅ | 4'-CH₃-Ph-4-Ph |
| 173 | C₃H₇-n | 4'-CH₃-Ph-4-Ph |
| 174 | C₃H₇-i | 4'-CH₃-Ph-4-Ph |
| 175 | C₄H₉-n | 4'-CH₃-Ph-4-Ph |
| 176 | CH₃ | 4'-CH₃-Ph-4-Ph |
| 177 | C₂H₅ | 4'-CH₃-Ph-4-Ph |
| 178 | C₃H₇-n | 4'-CH₃-Ph-4-Ph |
| 179 | C₃H₇-i | 4'-CH₃-Ph-4-Ph |
| 180 | C₄H₉-n | 4'-CH₃-Ph-4-Ph |
| 181 | CH₃ | 3,4-di-CH₃—Ph |
| 182 | C₂H₅ | 3,4-di-CH₃—Ph |
| 183 | C₃H₇-n | 3,4-di-CH₃—Ph |
| 184 | C₃H₇-i | 3,4-di-CH₃—Ph |
| 185 | C₄H₉-n | 3,4-di-CH₃—Ph |
| 186 | CH₃ | 3,4-di-CH₃—Ph |
| 187 | C₂H₅ | 3,4-di-CH₃—Ph |
| 188 | C₃H₇-n | 3,4-di-CH₃—Ph |
| 189 | C₃H₇-i | 3,4-di-CH₃—Ph |
| 190 | C₄H₉-n | 3,4-di-CH₃—Ph |
| 191 | CH₃ | 4-cycl-C₆H₁₁—Ph |
| 192 | C₂H₅ | 4-cycl-C₆H₁₁—Ph |
| 193 | C₃H₇-n | 4-cycl-C₆H₁₁—Ph |
| 194 | C₃H₇-i | 4-cycl-C₆H₁₁—Ph |
| 195 | C₄H₉-n | 4-cycl-C₆H₁₁—Ph |
| 196 | CH₃ | 4-cycl-C₆H₁₁—Ph |
| 197 | C₂H₅ | 4-cycl-C₆H₁₁—Ph |
| 198 | C₃H₇-n | 4-cycl-C₆H₁₁—Ph |
| 199 | C₃H₇-i | 4-cycl-C₆H₁₁—Ph |
| 200 | C₄H₉-n | 4-cycl-C₆H₁₁—Ph |
| 201 | CH₃ | 4-[N(CH₃)₂]—Ph |
| 202 | C₂H₅ | 4-[N(CH₃)₂]—Ph |
| 203 | C₃H₇-n | 4-[N(CH₃)₂]—Ph |
| 204 | C₃H₇-i | 4-[N(CH₃)₂]—Ph |
| 205 | C₄H₉-n | 4-[N(CH₃)₂]—Ph |
| 206 | CH₃ | 4-[N(CH₃)₂]—Ph |
| 207 | C₂H₅ | 4-[N(CH₃)₂]—Ph |
| 208 | C₃H₇-n | 4-[N(CH₃)₂]—Ph |
| 209 | C₃H₇-i | 4-[N(CH₃)₂]—Ph |
| 210 | C₄H₉-n | 4-[N(CH₃)₂]—Ph |
| 211 | CH₃ | 4-CN—Ph |
| 212 | C₂H₅ | 4-CN—Ph |
| 213 | C₃H₇-n | 4-CN—Ph |
| 214 | C₃H₇-i | 4-CN—Ph |
| 215 | C₄H₉-n | 4-CN—Ph |
| 216 | CH₃ | 4-CN—Ph |
| 217 | C₂H₅ | 4-CN—Ph |
| 218 | C₃H₇-n | 4-CN—Ph |
| 219 | C₃H₇-i | 4-CN—Ph |
| 220 | C₄H₉-n | 4-CN—Ph |

TABLE D-continued
| | R | A | |
|---|---|---|---|
| 221 | CH₃ | 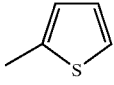 | |
| 222 | C₂H₅ | 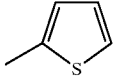 | |
| 223 | C₃H₇-n | 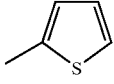 | |
| 224 | C₃H₇-i | 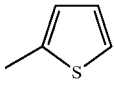 | |
| 225 | C₄H₉-n | 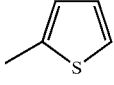 | |
| 226 | CH₃ | 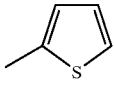 | |
| 227 | C₂H₅ | 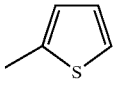 | |
| 228 | C₃H₇-n | 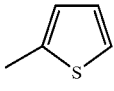 | |
| 229 | C₃H₇-i | 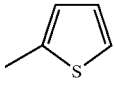 | |
| 230 | C₄H₉-n | 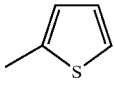 | |
| 231 | CH₃ | 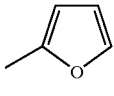 | |
| 232 | C₂H₅ | 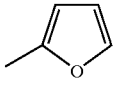 | |
| 233 | C₃H₇-n | 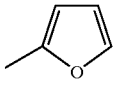 | |
| 234 | C₃H₇-i | 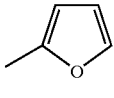 | |
| 235 | C₄H₉-n | 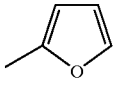 | |
TABLE D-continued
| | R | A | |
|---|---|---|---|
| 236 | CH₃ | 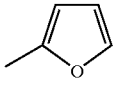 | |
| 237 | C₂H₅ | 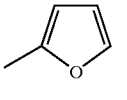 | |
| 238 | C₃H₇-n | 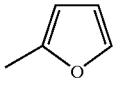 | |
| 239 | C₃H₇-i | 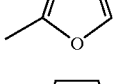 | |
| 240 | C₄H₉-n | 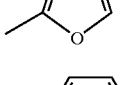 | |
| 241 | CH₃ | 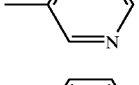 | |
| 242 | C₂H₅ | 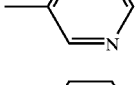 | |
| 243 | C₃H₇-n | 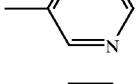 | |
| 244 | C₃H₇-i | 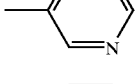 | |
| 245 | C₄H₉-n | 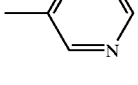 | |
| 246 | CH₃ | 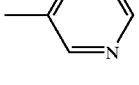 | |
| 247 | C₂H₅ | 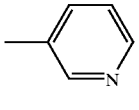 | |
| 248 | C₃H₇-n | 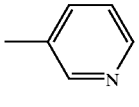 | |
| 249 | C₃H₇-i | 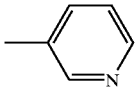 | |
| 250 | C₄H₉-n | 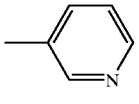 | |

TABLE D-continued

| | R | A |
|---|---|---|
| 251 | CH₃ | 4-C₃H₇-i-Ph |
| 252 | C₂H₅ | 4-C₃H₇-i-Ph |
| 253 | C₃H₇-n | 4-C₃H₇-i-Ph |
| 254 | C₃H₇-i | 4-C₃H₇-i-Ph |
| 255 | C₄H₉-n | 4-C₃H₇-i-Ph |
| 256 | CH₃ | 4-C₃H₇-i-Ph |
| 257 | C₂H₅ | 4-C₃H₇-i-Ph |
| 258 | C₃H₇-n | 4-C₃H₇-i-Ph |
| 259 | C₃H₇-i | 4-C₃H₇-i-Ph |
| 260 | C₄H₉-n | 4-C₃H₇-i-Ph |
| 261 | CH₃ | 4-C₄H₉-t-Ph |
| 262 | C₂H₅ | 4-C₄H₉-t-Ph |
| 263 | C₃H₇-n | 4-C₄H₉-t-Ph |
| 264 | C₃H₇-i | 4-C₄H₉-t-Ph |
| 265 | C₄H₉-n | 4-C₄H₉-t-Ph |
| 266 | CH₃ | 4-C₄H₉-t-Ph |
| 267 | C₂H₅ | 4-C₄H₉-t-Ph |
| 268 | C₃H₇-n | 4-C₄H₉-t-Ph |
| 269 | C₃H₇-i | 4-C₄H₉-t-Ph |
| 270 | C₄H₉-n | 4-C₄H₉-t-Ph |
| 271 | CH₃ | 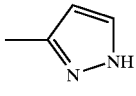 |
| 272 | C₂H₅ | 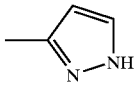 |
| 273 | C₃H₇-n | 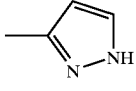 |
| 274 | C₃H₇-i | 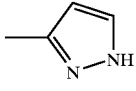 |
| 275 | C₄H₉-n | 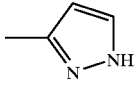 |
| 276 | CH₃ | 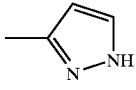 |
| 277 | C₂H₅ | 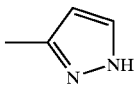 |
| 278 | C₃H₇-n | 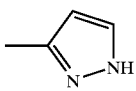 |
| 279 | C₃H₇-i | 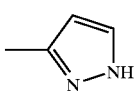 |
| 280 | C₄H₉-n | 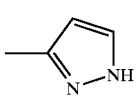 |
| 281 | CH₃ | 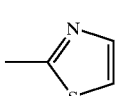 |
| 282 | C₂H₅ | 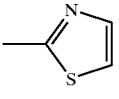 |
| 283 | C₃H₇-n | 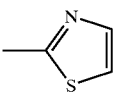 |
| 284 | C₃H₇-i | 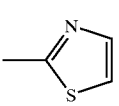 |
| 285 | C₄H₉-n | 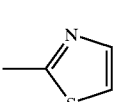 |
| 286 | CH₃ | 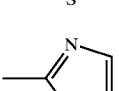 |
| 287 | C₂H₅ | 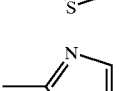 |
| 288 | C₃H₇-n | 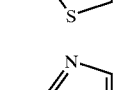 |
| 289 | C₃H₇-i | 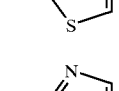 |
| 290 | C₄H₉-n | 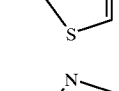 |
| 291 | CH₃ | 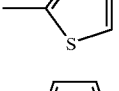 |
| 292 | C₂H₅ | 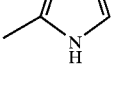 |
| 293 | C₃H₇-n | 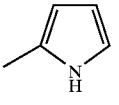 |
| 294 | C₃H₇-i | 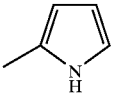 |
| 295 | C₄H₉-n | 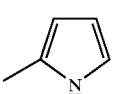 |

TABLE D-continued
| | R | A |
|---|---|---|
| 296 | CH$_3$ | 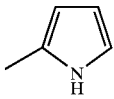 |
| 297 | C$_2$H$_5$ | 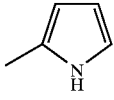 |
| 298 | C$_3$H$_7$-n | 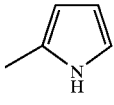 |
| 299 | C$_3$H$_7$-i | 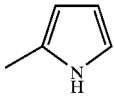 |
| 300 | C$_4$H$_9$-n | 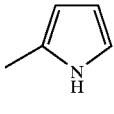 |
| 301 | CH$_3$ | 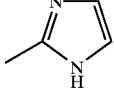 |
| 302 | C$_2$H$_5$ | 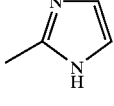 |
| 303 | C$_3$H$_7$-n | 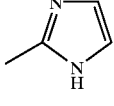 |
| 304 | C$_3$H$_7$-i | 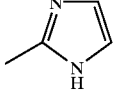 |
| 305 | C$_4$H$_9$-n | 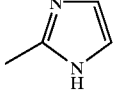 |
| 306 | CH$_3$ | 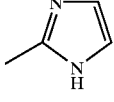 |
| 307 | C$_2$H$_5$ | 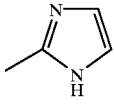 |
| 308 | C$_3$H$_7$-n | 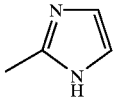 |
TABLE D-continued
| | R | A |
|---|---|---|
| 309 | C$_3$H$_7$-i | 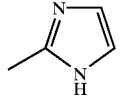 |
| 310 | C$_4$H$_9$-n | 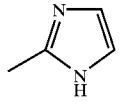 |
| 311 | CH$_3$ | 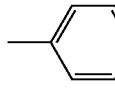 |
| 312 | C$_2$H$_5$ | 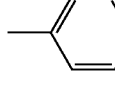 |
| 313 | C$_3$H$_7$-n | 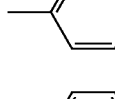 |
| 314 | C$_3$H$_7$-i | 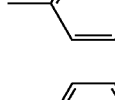 |
| 315 | C$_4$H$_9$-n | 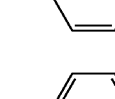 |
| 316 | CH$_3$ | 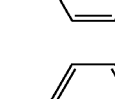 |
| 317 | C$_2$H$_5$ | 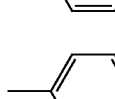 |
| 318 | C$_3$H$_7$-n | 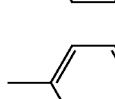 |
| 319 | C$_3$H$_7$-i | 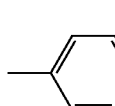 |
| 320 | C$_4$H$_9$-n | 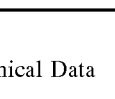 |
Selected Physico-chemical Data
| Compound No. | Melting Point, $^1$H-NMR, or Molpeak (ESMS) |
|---|---|
| 01.259 | 485 (M + HCOO)$^-$ |
| 01.260 | 625 (M + HCOO)$^-$ |

-continued

| Compound No. | Melting Point, $^1$H-NMR, or Molpeak (ESMS) |
|---|---|
| 11.151 | oil |
| 11.161 | oil |
| 11.171 | mp: 40–47° C. |
| 11.321 | oil |
| 11.331 | oil |
| 11.341 | oil |
| 11.351 | mp: 45–52° C. |
| 11.361 | oil |
| 11.371 | oil |
| 12.131 | 457/459 (M+ 1)$^+$ |
| 12.141 | 379 (M + 1)$^+$ |
| 13.011 | 451 (M − 1)$^-$ |
| 14.001 | 415 (M − 1)$^-$ |
| 14.002 | 431 (M + 1)$^+$ |
| 14.011 | 449 (M − 1)$^-$ |
| 14.012 | 509 (M + HCOO)$^-$ |
| 14.031 | 459/461 (M − 1)$^-$ |
| 14.041 | 397 (M + 1)$^+$ |
| 14.042 | 411 (M + 1)$^+$ |
| 14.051 | 413 (M + 1)$^+$ |
| 14.071 | 401 (M + 1)$^+$ |
| 14.091 | 443 (M + 1)$^+$ |
| 14.101 | 427 (M + 1)$^+$ |
| 14.111 | 417 (M − 1)$^-$ |
| 14.121 | 433 (M + 1)$^+$ |
| 14.131 | 465 (M − 1)$^-$ |
| 14.311 | 467 (M + 1)$^+$ |
| 17.011 | 477 (M − 1)$^-$ |
| 22.011 | 561 (M + 1)$^+$ |
| 22.041 | 507 (M + 1)$^+$ |
| 26.011 | 615 (M + HCOO)$^-$ |
| 30.008 | d ($^1$H-NMR,CDCl$_3$): 2.7 ppm (SMe) |
| 30.010 | mp:118–119° C. |

Formulations may be prepared analogously to those described in, for example, WO 95/30651.

Biological Examples

D-1: Action against *Plasmopara viticola* on Vines a) Residual-protective Action Vine seedlings are sprayed at the 4- to 5-leaf stage with a spray mixture (0.02% active ingredient) prepared from a wettable powder formulation of the test compound. After 24 hours, the treated plants are infected with a sporangia suspension of the fungus. Fungus infestation is evaluated after incubation for 6 days at 95–100% relative humidity and 20° C.

b) Residual-curative Action

Vine seedlings are infected at the 4- to 5-leaf stage with a sporangia suspension of the fungus. After incubation for 24 hours in a humidity chamber at 95–100% relative humidity and 20° C., the infected plants are dried and sprayed with a spray mixture (0.02% active ingredient) prepared from a wettable powder formulation of the test compound. After the spray coating has dried, the treated plants are placed in the humidity chamber again. Fungus infestation is evaluated 6 days after infection.

Compounds of Tables 1 to 40 exhibit a good fungicidal action against *Plasmopara viticola* on vines. Compounds 11.171, 11.351, 12.001, 13.011, 14.001, 14.011, 14.031, 14.041, 14.042, 14.051, 14.071, 14.121, 17.011, 30.008 and 30.010 completely inhibit fungal infestation in this test.

D-2: Action Against Phytophthora on Tomato Plants a) Residual-protective Action

After a cultivation period of 3 weeks, tomato plants are sprayed with a spray mixture (0.02% active ingredient) prepared from a wettable powder formulation of the test compound. After 48 hours, the treated plants are infected with a sporangia suspension of the fungus. Fungus infestation is evaluated after incubation of the infected plants for 5 days at 90–100% relative humidity and 20° C.

b) Systemic Action

After a cultivation period of 3 weeks, tomato plants are watered with a spray mixture (0.02% active ingredient based on the volume of the soil) prepared from a wettable powder formulation of the test compound. Care is taken that the spray mixture does not come into contact with the parts of the plants that are above the ground. After 96 hours, the treated plants are infected with a sporangia suspension of the fungus. Fungus infestation is evaluated after incubation of the infected plants for 4 days at 90–100% relative humidity and 20° C. Compounds of Tables 1 to 40 exhibit a long-lasting effect against fungus infestation. Compounds 13.011, 14.001, 14.011, 14.031, 14.041, 14.042, 17.011 and 30.008 completely inhibit fungal infestation in this test.

D-3: Action Against Phytophthora on Potato Plants a) Residual-protective Action

2–3 week old potato plants (Bintje variety) are sprayed with a spray mixture (0.02% active ingredient) prepared from a wettable powder formulation of the test compound. After 48 hours, the treated plants are infected with a sporangia suspension of the fungus. Fungus infestation is evaluated after incubation of the infected plants for 4 days at 90–100% relative humidity and 20° C.

b) Systemic Action

2–3 week old potato plants (Bintje variety) are watered with a spray mixture (0.02% active ingredient based on the volume of the soil) prepared from a wettable powder formulation of the test compound. Care is taken that the spray mixture does not come into contact with the parts of the plants that are above the ground. After 48 hours, the treated plants are infected with a sporangia suspension of the fungus. Fungus infestation is evaluated after incubation of the infected plants for 4 days at 90–100% relative humidity and 20° C.

Compounds of Tables 1 to 40 exhibit a good fungicidal action against Phytophthora on potatoes. Compounds 14.001, 14.011, 14.041 and 30.008 completely inhibit fungal infestation in this test.

What is claimed is:

1. A α-sulfenimino acid derivative of formula I

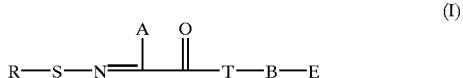

(I)

Including the optical isomers thereof and mixtures of such isomers, wherein

A is cycloalkyl, cycloalkenyl or aryl, each optionally substituted,

B is a direct bond or optionally substituted alkylene,

E is optionally substituted aryl,

R is hydrogen, alkyl, alkenyl, alkynyl, cycloalkyl, cycloalkylalkyl, aryl or arylalkyl, each optionally substituted, and T is NH.

2. A compound according to claim 1 wherein

A is phenyl, naphthyl, cycloalkyl or cycloalkenyl, wherein each of the cycles is optionally mono- or poly-substituted by substituents selected from the group comprising $C_{1-8}$-alkyl, $C_{2-8}$-alkenyl, $C_{2-8}$-alkynyl, $C_{3-8}$-cycloalkyl, $C_{3-8}$-cycloalkyl-$C_{1-6}$-alkyl, $C_{1-8}$-alkoxy, $C_{3-8}$-alkenyloxy, $C_{3-8}$-alkynyloxy, $C_{3-8}$cycloalkyloxy, $C_{1-8}$-alkylthio, $C_{1-8}$-alkylsulfonyl, $C_{1-8}$-alkanoyl, $C_{1-8}$-alkanoyloxy, $C_{1-8}$-alkoxycarbonyl, $C_{3-8}$-alkenyloxycarbonyl, $C_{3-8}$-alkynyloxycarbonyl, $C_{1-8}$-dialkylamino, $C_{1-8}$-alkylamino, $C_{1-8}$-hydroximinoalkyl and $C_{1-8}$-alkoximinoalkyl wherein each of the alkyl, alkenyl, alkynyl moieties are straight-chain or branched and may in turn be optionally halogenated; halogen; nitro; cyano; hydroxy; amino; formyl; carboxyl; carbamoyl and thiocarbamoyl; or from the group comprising aryl, aryloxy, arylthio, aryl-$C_{1-4}$-alkyl, aryl-$C_{1-4}$-alkyloxy or aryl-$C_{1-4}$-alkylthio, wherein each of the groups may be substituted with halogen, cyano, $C_{1-4}$-alkyl, $C_{1-4}$-alkoxy or $C_{1-4}$-alkylthio; or from the group comprising aryloxyalkyl, arylalkyliminoxyalkyl, aryloxyiminoalkyl, arylalkyloxylminoalkyl, aryloxyiminoalkyleniminoxyalkyl and aryl-alkyloxyiminoalkyleniminoxyalkyl wherein each alkyl or alkylene may be straight-chain or branched and each aryl may in turn be substituted with halogen, cyano, $C_{1-4}$-alkyl, $C_{1-4}$-alkoxy or $C_{1-4}$-calkylthio; and B is a direct bond or $C_{1-4}$-alkylene which is optionally substituted with substituents selected from the group comprising halogen, linear or branched $C_{1-6}$-alkyl, $C_{2-8}$-alkenyl or $C_{2-8}$-alkynyl and $C_{5-7}$-cycloalkyl, each in turn optionally substituted with 1–4 halogen atoms; and E is phenyl optionally mono- or poly-substituted with substituents selected from the group comprising $C_{1-8}$-alkyl, $C_{2-8}$-alkenyl, $C_{2-8}$-alkynyl, $C_{3-8}$-cycloalkyl, $C_{3-8}$-cycloalkyl-$C_{1-6}$-alkyl, $C_{1-8}$-alkoxy, $C_{3-8}$-alkenyloxy, $C_{3-8}$-alkynyloxy, $C_{3-8}$-cycloalkyloxy, $C_{8-10}$-aryloxy, $C_{8-10}$-aryl-$C_{1-8}$-alkyloxy, $C_{6-10}$-aryl-$C_{3-8}$-alkenyloxy, $C_{8-10}$-aryl-$C_{3-6}$-alkynyloxy, $C_{1-8}$-alkanoyloxy, $C_{3-8}$-cycloalkyl-$C_{3-6}$-alkynyloxy, $C_{1-8}$-alkylthio, $C_{1-8}$-alkylsulfonyl, $C_{1-8}$-alkanoyl, $C_{1-8}$-alkoxycarbonyl, $C_{3-8}$-alklyloxycarbonyl and $C_{3-8}$-alkinyloxycarbonyl wherein in each of the preceding groups the alkyl, alkenyl, alkynyl or cycloalkyl part may be partially or fully halogenated and wherein the aryl groups may be optionally mono- or poly-substituted with substituents selected from the group comprising $C_{1-8}$-alkyl, $C_{2-8}$-alkenyl, $C_{3-8}$-cycloalkyl, $C_{1-8}$-alkoxy, $C_{1-8}$-alkylthio, $C_{1-8}$-alkoxycarbonyl, $C_{1-8}$-haloalkyl, $C_{1-8}$-haloalkoxy, $C_{1-8}$-haloalkylthio, halogen, nitro and cyano; halogen, nitro, cyano, hydroxy, amino, di $C_{1-8}$-alkylamino and $C_{1-8}$-alkylamino; and R is hydrogen or $C_{1-10}$-alkyl, $C_{2-10}$-alkenyl, $C_{2-10}$-alkynyl, $C_{3-8}$-cycloalkyl, $C_{3-8}$-cycloalkyl-$C_{1-8}$-alkyl, $C_{6-10}$-aryl or $C_{6-10}$-aryl-$C_{1-8}$-alkyl, wherein each of the preceding groups may be optionally mono- or poly-substituted with substituents selected from the group comprising $C_{1-8}$-alkyl, $C_{2-8}$-alkenyl, $C_{2-8}$-alkynyl, $C_{3-8}$-cycloalkyl, $C_{3-8}$-cycloalkyl-$C_{1-6}$-alkyl, $C_{1-8}$-alkoxy, $C_{3-8}$-alkenyloxy, $C_{3-8}$-alkynyloxy, $C_{1-8}$-alkylthio, $C_{1-8}$-alkylsulfonyl, $C_{1-8}$-alkanoyl, $C_{1-8}$-alkoxycarbonyl, $C_{3-8}$-alkenyloxycarbonyl and $C_{3-8}$-alkyl-nyloxycarbonyl wherein each of the alkyl, alkenyl, alkynyl or cycloalkyl parts of the preceding substituents may be partially or fully halogenated; halogen, nitro and cyano.

3. A compound of formula I according to claim 1 wherein A is phenyl or naphthyl, each optionally-substituted by 1 to 3 substituents selected from the group comprising $C_{1-8}$-alkyl, $C_{2-8}$-alkenyl, $C_{3-8}$-cycloalkyl, $C_{1-8}$-alkoxy, $C_{1-8}$-alkylthio, $C_{1-8}$-alkoxycarbonyl, $C_{1-8}$-haloalkyl, $C_{1-8}$-haloalkoxy, $C_{1-8}$-haloalkylthio, halogen, nitro and cyano; or from the group comprising aryl, aryloxy, arylthio, aryl-$C_{1-4}$-alkyl, aryl-$C_{1-4}$-alkyloxy or aryl-$C_{1-4}$-alkylthio, wherein each of the groups may be substituted with halogen, cyano, $C_{1-4}$-alkyl, $C_{1-4}$-alkoxy or $C_{1-4}$-alkylthio; or from the group comprising phenoxy-$C_{1-4}$-alkyl, phenyl-$C_{1-4}$-alkyliminoxy-$C_{1-4}$-alkyl and phenyl-alkoxyimino-$C_{2-4}$-alkyleniminoxy-$C_{1-4}$-alkyl wherein each alkyl or alkylene may be straight-chain or branched and each phenyl or phenoxy may in turn be substituted with halogen, cyano, $C_{1-4}$-alkyl, $C_{1-4}$-alkoxy or $C_{1-4}$-alkylthio; and B is a direct bond or $C_{1-4}$-alkylene which is optionally substituted with substituents selected from the group comprising F, Cl, Br, linear or branched $C_{1-4}$-alkyl, $C_{1-4}$-alkenyl or, $C_{2-4}$-alkynyl and $C_{5-7}$-cycloalkyl, each in turn optionally substituted with 1–4 halogen atoms; and E is phenyl optionally mono- to tri-substituted with substituents selected from the group comprising $C_{1-8}$-alkyl, $C_{1-8}$-alkoxy, $C_{3-8}$-alkenyloxy, $C_{3-8}$-alkynyloxy, phenyl-$C_{1-8}$-alkyloxy, phenyl-$C_{3-8}$-alkenyloxy, phenyl-$C_{3-8}$-alkynyloxy, $C_{3-8}$-cycloalkyl-$C_{3-6}$alkynyloxy, $C_{1-8}$-alkylthio, $C_{1-8}$-alkoxycarbonyl, $C_{1-8}$-haloalkoxy, $C_{3-8}$-haloalkenyloxy, halogen and cyano, wherein the phenyl groups may be optionally mono- to tri-substituted with substituents selected from the group comprising $C_{1-4}$-alkyl, $C_{1-4}$-alkoxy, $C_{1-4}$-alkylthio, $C_{1-4}$-haloalkyl, $C_{1-4}$-haloalkoxy, $C_{1-4}$-haloalkylthio, halogen and cyano; and R is $C_{1-10}$-alkyl, $C_{2-10}$-alkenyl or $C_{1-4}$-cycloalkyl, wherein each of the preceding groups may be optionally mono- or poly-substituted with substituents selected from the group comprising $C_{1-8}$-alkyl, $C_{1-8}$-alkoxy, $C_{1-8}$-alkylthio, $C_{1-8}$-alkanoyl, $C_{1-8}$-alkoxycarbonyl, $C_{1-8}$-haloalkyl, $C_{1-8}$-haloalkoxy, $C_{1-8}$-haloalkylthio, halogen, nitro and cyano.

4. A compound of formula I according to claim 1 wherein A is phenyl or naphthyl, each optionally-substituted by 1 to 3 substituents selected from the group comprising $C_{1-8}$-alkyl, $C_{2-8}$-alkenyl, $C_{3-8}$-cycloalkyl, $C_{1-8}$-alkoxy, $C_{1-8}$-alkylthio, $C_{1-8}$-alkoxycarbonyl, $C_{1-8}$-haloalkyl, $C_{1-8}$-haloalkoxy, $C_{1-8}$-haloalkylthio, halogen, nitro and cyano; or from the group comprising aryl, aryloxy or arylthio, wherein each of the groups may be substituted with halogen, cyano, $C_{1-4}$-alkyl, $C_{1-4}$-alkoxy or $C_{1-4}$-alkylthio; or from a group comprising phenoxy-$C_{1-4}$-alkyl, phenyl-$C_{1-4}$-alkyliminoxy-$C_{1-4}$-alkyl and phenyl-alkoxylmino-$C_{2-4}$-alkyleniminoxy-$C_{1-4}$-alkyl wherein each alkyl or alkylene may be straight-chain or branched and each phenyl or phenoxy may in turn be substituted with halogen, cyano, $C_{1-4}$-alkyl, $C_{1-4}$-alkoxy or $C_{1-4}$-alkylthio; and B is a direct bond or $C_{1-4}$-alkylene which is optionally substituted with substituents selected from the group comprising F, Cl, Br, linear or branched $C_{1-2}$-alkyl, $C_{2-3}$-alkenyl or, $C_{2-3}$-alkynyl and $C_{5-7}$-cycloalkyl, each in turn optionally substituted with 1–4 halogen atoms; and E is phenyl optionally di- to tri-substituted with substituents selected from the group comprising $C_{1-8}$-alkyl, $C_{1-8}$-alkoxy, $C_{3-8}$-alkenyloxy, $C_{3-8}$-alkynyloxy, phenyl-$C_{1-6}$-alkyloxy, phenyl-$C_{3-6}$-alkenyloxy, phenyl-$C_{3-8}$-alkynyloxy, $C_{3-8}$-cycloalkyl-$C_{3-6}$-alkynyloxy, $C_{1-8}$-alkylthio, $C_{1-8}$-alkoxycarbonyl, $C_{1-8}$-haloalkoxy, $C_{3-8}$-haloalkenyloxy, halogen and cyano, wherein the phenyl groups may be optionally mono- to tri-substituted with substituents selected from the group comprising $C_{1-4}$-alkyl, $C_{1-4}$-alkoxy, $C_{1-4}$-alkylthio, $C_{1-4}$-haloalkyl, $C_{1-4}$-haloalkoxy, $C_{1-4}$-haloalkylthio, halogen and cyano; and R is $C_{1-6}$-alkyl, $C_{2-6}$-alkenyl or $C_{5-6}$-cycloalkyl, wherein each of the preceding groups may be optionally mono- or poly-substituted with substituents selected from the group comprising $C_{1-4}$-alkyl, $C_{1-4}$-alkoxy, $C_{1-4}$-alkoxycarbonyl, $C_{1-4}$haloalkyl, halogen and cyano.

5. A compound of formula I according to claim 1 wherein A is phenyl or naphthyl, each optionally-substituted by 1 to 3 substituents selected from the group comprising $C_{1-4}$-alkyl, $C_{2-6}$-alkenyl, $C_{3-6}$-cycloalkyl, $C_{1-4}$-alkoxy, $C_{1-4}$-alkylthio, $C_{1-4}$-alkoxycarbonyl, $C_{1-4}$-haloalkyl, $C_{1-4}$-haloalkoxy, $C_{1-4}$-haloalkylthio, halogen, nitro and cyano; or from the group comprising aryl, aryloxy or arylthio, wherein each of the groups may be substituted with halogen, cyano, $C_{1-4}$-alkyl, $C_{1-4}$-alkoxy or $C_{1-4}$-alkylthio; and B is a direct bond, methylene, 1,1-ethylene, 1,2-ethylene, 1,1-propylene, 1,2-propylene, 1,3-propylene or 2,2-propylene; and E is a group

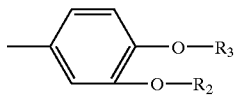

wherein $R_2$ is $C_{1-4}$-alkyl, and $R_3$ is $C_{1-8}$-alkyl, $C_{3-8}$-alkenyl, $C_{3-8}$-alkynyl, phenyl-$C_{1-6}$-alkyl, phenyl-$C_{3-6}$-alkenyl, phenyl-$C_{3-0}$-alkynyl, $C_{3-8}$-cycloalkyl-$C_{3-8}$-alkynyl, $C_{1-8}$-halogenalkyl or $C_{3-8}$-halogenalkenyl wherein in each of the preceding radicals the phenyl groups may be optionally substituted with 1 to 3 substituents selected from the group comprising $C_{1-4}$-alkyl, $C_{1-4}$-alkoxy, $C_{1-4}$-alkylthio, $C_{1-4}$-haloalkyl, $C_{1-4}$-haloalkoxy, $C_{1-4}$-haloalkylthio, halogen and cyano; and R is straight-chain or branched $C_{1-4}$-alkyl, $C_{2-6}$-alkenyl or $C_{5-6}$-cycloalkyl, wherein each of the preceding groups may be optionally mono- or poly-substituted with F, Cl or Br; and T is NH.

6. A composition for controlling and protecting against phytopathogenic microorganisms, comprising a compound of formula I according to claim 1 as active ingredient together with a suitable carrier.

7. A method of controlling and preventing an infestation of crop plants by phytopathogenic microorganisms, which comprises the application of a compound of formula I according to claim 1 as active ingredient to the plant, to parts of plants or to the locus thereof.

8. A method according to claim 7, wherein the phytopathogenic microorganisms are fungal organisms.

9. A compound according to claim 1 selected from the group consisting of 2-(3,4-dichloro-phenyl)-N-[2-(4-ethoxy-3-methoxy-phenyl)-ethyl]-2-methylthiolmino-acetamide, 2-(3,4-dichloro-phenyl)-N-[2-(3-methoxy-4-prop-2-ynyloxy-phenyl)-ethyl]-2-methylthiolmino-acetamide;

2-(3,4-dichloro-phenyl)-N-[2-(3-methoxy-4-pent-2-ynyloxy-phenyl)-ethyl]-2-methylthiolmino-acetamide;

N-[2-(4-allyloxy-3-methoxy-phenyl)-ethyl]-2-(3,4-dichloro-phenyl)-2-methylthiolmino-acetamide;

N-[2-(3-methoxy-4-prop-ynyloxy-phenyl)-ethyl]-2-methylthiolmino-2-(4-tolyl )-acetamide;

2-C4-bromo-phenyl)-N-2-(3-methoxy-4-prop-2-ynyloxy-phenyl)-ethyl]-2-methylthiolmino-acetamide;

2(4-chloro-phenyl)-N-[2-(3-methoxy-4-prop-2-ynyloxy-phenyl)-ethyl]-2-methylthioimino-acetamide;

N-[2-(3-methoxy-4-prop-ynyloxy-phenyl)-ethyl]-2-naphthalen-2-yl-2-methylthioimino-2-acetamide;

2-(4-fluoro-phenyl)-N-[2-(3-methoxy-4-prop-2-ynyloxy-phenyl)-ethyl]-2-methylthiolmino-acetamide;

2-(4-methoxy-phenyl)-N-[2-(3-methoxy-4-prop-2-ynyloxy-phenyl)-ethyl]-2-methylthioimino-acetamide;

N-[2-(3-methoxy-4-prop-ynyloxy-phenyl)-ethyl]-2-(3,4-dichloro-phenyl)-2-ethylthioimino-2-(4-tolyl)-acetamide;

2-[4-(4-methyl-phenyl)-phenyl]-N-[2-(3,4-di-methoxy-phenyl)-ethyl]-2-methylthiolmino-acetamide;

2-[4-(3,4-dichloro-phenyl)-phenyl]-N-[2-(3,4-di-methoxy-phenyl)-ethyl]-2-methylthiolmino-acetamide;

2-[4-(4-chloro-phenyl)-phenyl]-N-[2-(3,4-di-methoxy-phenyl)-ethyl]-2-methylthioimino-acetamide;

2-[4-(4-trifluoromethyl-phenyl)-phenyl]-N-[2-(3,4-di-methoxy-phenyl)-ethyl]-2-methylthiolmino-acetamide;

2-[4-(4-trifluoromethoxy-phenyl)-phenyl]-N-[2-(3,4-di-methoxy-phenyl)-ethyl]-2-methylthiolmino-acetamide;

2-[4-(4-tert.-butyl-phenyl)-phenyl]-N-[2-(3,4-di-methoxyphenyl)-ethyl]-2-methylthiolmino-acetamide; and 2-(4-biphenylyl)-N-[2-(3,4-di-methoxy-phenyl)-ethyl]-2-methylthiolmino-acetamide.

* * * * *